US012734360B1

(12) United States Patent
Romero-Ortega et al.

(10) Patent No.: US 12,734,360 B1
(45) Date of Patent: Sep. 15, 2026

(54) SYSTEMS AND METHODS FOR SELECTIVE PERIPHERAL NERVE REGENERATION AND REMYELINATION

(71) Applicant: Regenerative Bioelectronics Inc., Worcester, MA (US)

(72) Inventors: Mario Romero-Ortega, Coppell, TX (US); David Constantine, Sudbury, MA (US); Jayme Coates, Worcester, MA (US); Gregory Martin, Worcester, MA (US)

(73) Assignee: Regenerative Bioelectronics Inc.

( * ) Notice: Subject to any disclaimer, the term of this patent is extended or adjusted under 35 U.S.C. 154(b) by 0 days.

(21) Appl. No.: 19/408,297

(22) Filed: Dec. 3, 2025

(51) Int. Cl.
*A61N 1/36* (2006.01)
*A61N 1/05* (2006.01)

(52) U.S. Cl.
CPC ....... *A61N 1/36103* (2013.01); *A61N 1/0521* (2013.01); *A61N 1/0556* (2013.01); *A61N 1/0558* (2013.01); *A61N 1/36003* (2013.01); *A61N 1/36007* (2013.01); *A61N 1/36139* (2013.01); *A61N 1/36157* (2013.01);
(Continued)

(58) Field of Classification Search
CPC .............. A61N 1/36103; A61N 1/0521; A61N 1/0556; A61N 1/0558; A61N 1/26003; A61N 1/36007; A61N 1/36139; A61N 1/36157; A61N 1/36171; A61N 1/36175; A61N 1/36178
See application file for complete search history.

(56) References Cited

U.S. PATENT DOCUMENTS 11,771,902 B2 10/2023 Craig
12,226,636 B2 2/2025 Carmena et al.
(Continued)

FOREIGN PATENT DOCUMENTS

AU 2012202408 B2 1/2014
WO 2020231440 A1 11/2020
WO 2024086209 A2 4/2024

OTHER PUBLICATIONS

Romero-Ortega, M., et al., "Neuromodulation of Pelvic Nerves Increases Nerve Regeneration After Injury," PowerPoint Presentation, American Urological Association (AUA) Annual Meeting, Apr. 2025, 12 pages.
(Continued)

*Primary Examiner* — Scott Luan
(74) *Attorney, Agent, or Firm* — Nutter McClennen & Fish LLP

(57) ABSTRACT

A method promotes axonal regeneration and remyelination repair of a peripheral nerve. The method stimulates a target peripheral nerve or target distal branch thereof with a stimulator having a direct-contact electrode configured to couple to a nerve having a diameter of between 1 mm and 25 mm. Each pulse train includes pulses having a frequency between about 20 Hz and 100 Hz, and a pulse width between about 150 microseconds and 500 microseconds. The pulse trains have a train duration between about 3 seconds and 60 seconds and are separated by rest intervals between about 0.5 minute and 5 minutes. The stimulation amplitude is titrated relative to a threshold. The pulse trains are delivered in 1 to 8 pulse trains per session. Accordingly, the method initiates axonal regeneration and/or promotes remyelination repair in the target nerve.

25 Claims, 23 Drawing Sheets

(52) U.S. Cl.
CPC ..... *A61N 1/36171* (2013.01); *A61N 1/36175* (2013.01); *A61N 1/36178* (2013.01)

(56) References Cited

U.S. PATENT DOCUMENTS

| | | | | |
|---|---|---|---|---|
| 12,343,535 | B2 | 7/2025 | Levine et al. | |
| 2022/0061741 | A1* | 3/2022 | Robison ............... | A61B 5/4082 |
| 2024/0181256 | A1 | 6/2024 | Gibson et al. | |

OTHER PUBLICATIONS

Romero-Ortega, M., et al., "Pelvic Neuromodulation Improves Urethral Pressure in Aging Multiparous Sheep," PowerPoint Presentation, American Urological Association (AUA) Annual Meeting, Apr. 2025, 13 pages.
Romero-Ortega, M., et al., "PD39-05 Neuromodulation of Pelvic Nerves Increases Nerve Regeneration After Injury," Journal of Urology, vol. 213, No. 5S, Apr. 29, 2025, 1 page.
Romero-Ortega, M., et al., "PD39-04 Pelvic Neuromodulation Improves Urethral Pressure in Aging Multiparous Sheep", Journal of Urology, vol. 213, No. 5S, Apr. 29, 2025, 1 page.
Benson, K., et al., One-year outcomes of the ARTISAN-SNM study with the Axonics System for the treatment of urinary urgency incontinence. Neurourol Urodyn. Jun. 2020; 39(5):1482-1488.
Blok, B., et al., Three month clinical results with a rechargeable sacral neuromodulation system for the treatment of overactive bladder. Neurourol Urodyn. Feb. 2018;37(S2):S9-S16.
Brink, T., et al., A Chronic, Conscious Large Animal Platform to Quantify Therapeutic Effects of Sacral Neuromodulation on Bladder Function. J Urol. Jul. 2015; 194(1):252-8.
Chartier-Kastler, E., et al., Sacral Neuromodulation with the InterStimTM System for Intractable Lower Urinary Tract Dysfunctions (SOUNDS): Results of Clinical Effectiveness, Quality of Life, Patient-Reported Outcomes and Safety in a French Multicenter Observational Study. Eur Urol Focus. Nov. 2021; 7(6):1430-1437.
Chen, A., et al., Initial experience using the Axonics sacral neuromodulation system in patients with multiple sclerosis. Neurourol Urodyn. Aug. 2022;41(6):1373-1379.
Hetzer, F., et al., Quality of life and morbidity after permanent sacral nerve stimulation for fecal incontinence. Arch Surg. Jan. 2007; 142(1):8-13.
Hull, T., et al. Long-term durability of sacral nerve stimulation therapy for chronic fecal incontinence. Dis Colon Rectum. Feb. 2013;56(2):234-45.
International Search Report and Written Opinion for International Application No. PCT/US2025/057980, mailed on Mar. 27, 2026, 17 pages.
Jottard, K., et al., Treatment of Fecal Incontinence With a Rechargeable Sacral Neuromodulation System: Efficacy, Clinical Outcome, and Ease of Use-Six-Month Follow-Up. Neuromodulation. Oct. 2021; 24(7):1284-1288.
Kohli, N., et al., InterStim Therapy: A Contemporary Approach to Overactive Bladder. Rev Obstet Gynecol. 2009 Winter;2(1):18-27.
Li, X., et al., Effects of Acute Sacral Neuromodulation at Different Frequencies on Bladder Overactivity in Pigs. Int Neurourol J. Jun. 2, 20171;21(2):102-108.
Mccrery, R., et al., Treatment of Urinary Urgency Incontinence Using a Rechargeable SNM System: 6-Month Results of the ARTISAN-SNM Study. J Urol. Jan. 2020;203(1):185-192.
Meng, L., et al., Sacral neuromodulation for overactive bladder using the InterStim and BetterStim systems. Sci Rep. Dec. 2, 20224; 12(1):22299.
Pezzella, A., et al., Two-year outcomes of the ARTISAN-SNM study for the treatment of urinary urgency incontinence using the Axonics rechargeable sacral neuromodulation system. Neurourol Urodyn. Feb. 2021; 40(2):714-721.
Poole, R.L., et al., Axonics Sacral Neuromodulation System for Treating Refractory Overactive Bladder: A Nice Medical Technologies Guidance. Appl Health Econ Health Policy. May 2022;20(3):305-313.
Romero-Ortega, M., et al., "Acute Pelvic Neuromodulation Increases Maximum Urethral Pressure in Female Sheep," SUFU 2024 Winter Meeting Digital Program Book, 2024, p. 204.
Romero-Ortega, M., et al., "Acute Pelvic Neuromodulation Increases Maximum Urethral Pressure in Female Sheep," Poster Board Presentation, Society of Urodynamics, Female Pelvic Medicine & Urogenital Reconstruction (SUFU) 2024 Winter Meeting, Feb. 2024, 1 page.
Romero-Ortega, M., et al., "Acute Pelvic Neuromodulation Increases Maximum Urethral Pressure in Female Sheep," PowerPoint Presentation, Society of Urodynamics, Female Pelvic Medicine & Urogenital Reconstruction (SUFU) 2024 Winter Meeting, Feb. 2024, 6 pages.
Siegel, S., et al., Five-year follow-up results of a prospective, multicenter study of patients with overactive bladder treated with sacral neuromodulation. The Journal of Urology. 2018; vol. 199(1), 229-236.
Siegel, S., et al., Results of a prospective, randomized, multicenterstudy evaluating sacral neuromodulation with InterStimTM therapy compared tostandard medical therapy at 6-months in subjects with mild symptoms of overactivebladder. Neurourol Urodyn. 2015;34(3):224-230.
Wexner, S.D., et al., Sacral nerve stimulation for fecal incontinence: results of a 120-patient prospective multicenter study. Ann Surg. 2010Mar;251(3): 441-449.

* cited by examiner

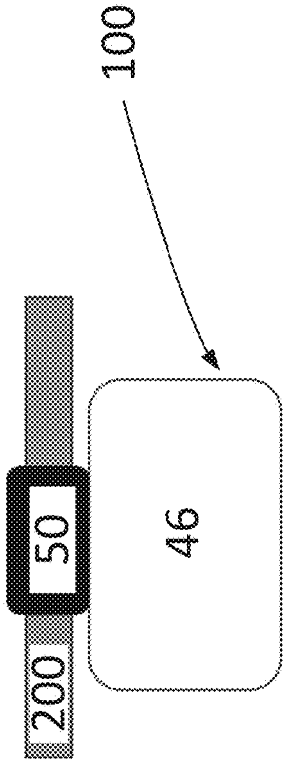
FIG. 3B
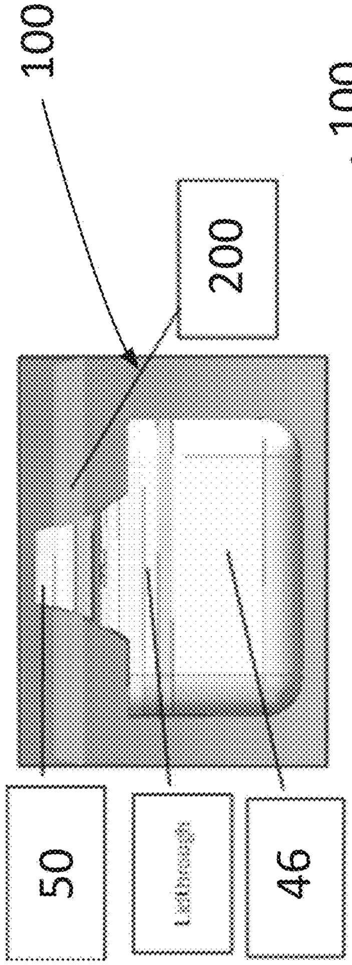
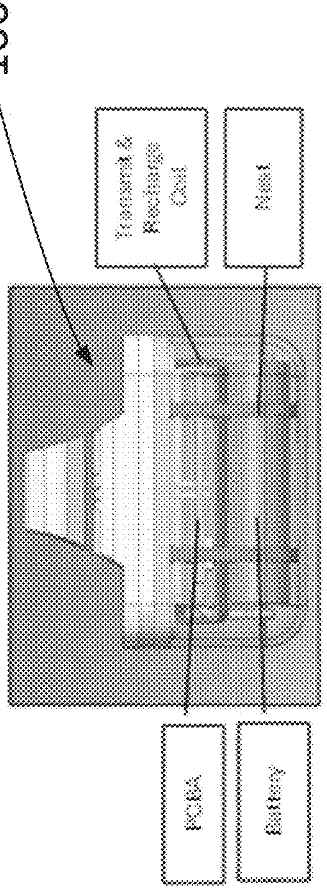
FIG. 3C

Burst
Rest
Burst
Intrasession rest
Session duration
Intersession rest
Intersession rest Pulse train envelope / pulse burst
Pulse train envelope
Stimulation pulse period (msec)
Intrasession Rest Time between stimulation pulse trains (msec)
Session duration
Intersession rest
Session duration

Regeneration MOA: Crush Hemisection Injury Model in Young Nulliparous Female Rabbits Methods:
n=3 No Injury Control (Healthy)
n=3 Crush Nerve Injury with SHAM Implant (Injured)
n=5 Crush Nerve Injury with NeuroClip Stimulation (Treatment)

Nerve exposed, cryo-crush injury performed and wireless NeuroClip implanted

Regenerative Mechanism Evident in Histology Data
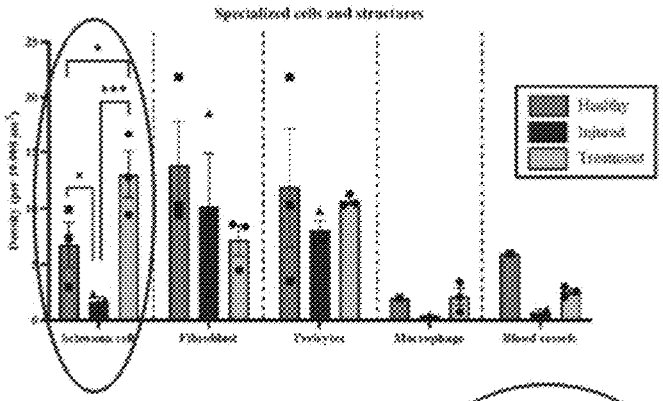
- Increase in Schwann cell density consistent with neuro-regenerative mechanisms.
- Axon growth indicates regenerative mechanism present
  - 61.65% frequency of myelinated axons in normal range
  - 47.19% of unmyelinated axons with normal diameter
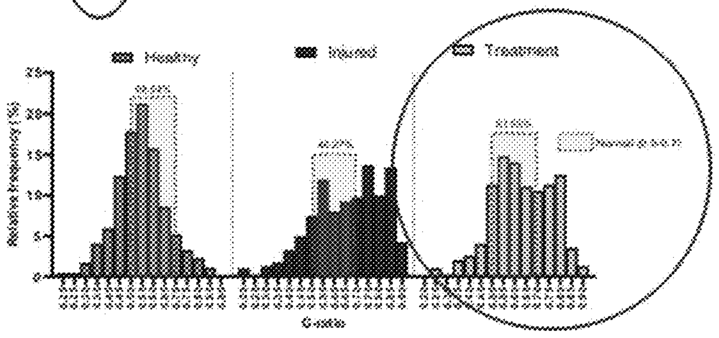
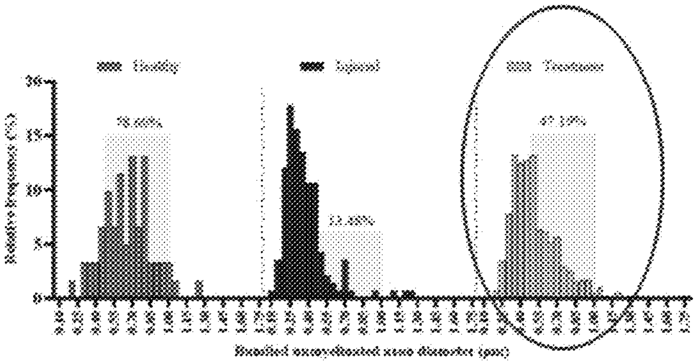
*FIG. 7*

SYSTEMS AND METHODS FOR SELECTIVE PERIPHERAL NERVE REGENERATION AND REMYELINATION

FIELD OF THE INVENTION

Illustrative embodiments of the invention generally relate to nerve stimulation and, more particularly, various embodiments of the invention relate to selectively stimulating peripheral nerves using parameterized pulse trains to promote axonal regeneration and remyelination repair.

BACKGROUND OF THE INVENTION

Peripheral nerve injuries and dysfunctions, including those affecting pelvic floor control, often result in impaired conduction and loss of muscle function. Pelvic floor disorders, including urinary incontinence (UI), fecal incontinence (FI), and pelvic organ prolapse (POP), are prevalent conditions that significantly impact the quality of life, particularly for a substantial portion of the adult female population. These disorders often arise from injuries to pelvic nerves and muscles, which may occur during pregnancy, vaginal delivery, or as a result of surgical or obstetrical procedures involving the pelvic or perineal regions. Current treatment options for nerve injuries are frequently limited in efficacy.

SUMMARY OF VARIOUS EMBODIMENTS

In accordance with an embodiment, a stimulation system includes a neuromodulation device configured to couple with a stimulation target having a diameter between about 0.5 mm and about 3.0 mm. The neuromodulation device includes a target coupling portion having at least one movable portion that define a channel leading to a stimulation chamber configured to receive the stimulation target. The stimulation target is a nerve having a diameter of between about 0.5 mm and about 3.0 mm. The device has a plurality of electrodes including at least one active electrode and at least one return electrode. The active and return electrodes have an interelectrode spacing between about 2.5 mm and about 3.5 mm. Each electrode has a width between about 0.4 mm and about 0.6 mm. The system also includes a controller operatively coupled to the neuromodulation device. The controller is configured to generate a stimulation session having no more than 8 stimulation pulse bursts. The stimulation session is less than 1 hour. Each of the pulse bursts configured to have stimulation pulses having a frequency between 20 Hz and 100 Hz, a current controlled amplitude of between 0.1 mA and 3 mA, and a pulse width between 150 microseconds and 500 microseconds.

In accordance with another embodiment, a method promotes axonal regeneration and remyelination repair of a peripheral nerve. The method stimulates a target peripheral nerve or target distal branch thereof with a stimulator having a direct-contact electrode. The stimulator is configured to couple to a nerve having a diameter of between 1 mm and 25 mm. The method delivers one or more pulse trains to the target nerve. Each pulse train includes pulses having a frequency between about 20 Hz and 100 Hz, and a pulse width between about 150 microseconds and 500 microseconds. The pulse trains have a train duration between about 3 seconds and 60 seconds and are separated by rest intervals between about 0.5 minute and 5 minutes. The stimulation amplitude is titrated relative to a threshold appropriate for the nerve type, including, at or above contraction threshold for a motor nerve, at or below sensation threshold for a sensory nerve, or at/above a physiological threshold for an autonomic nerve. The pulse trains are delivered in 1 to 8 pulse trains per session. Accordingly, the method initiates axonal regeneration and/or promotes remyelination repair in the target nerve.

In accordance with yet another embodiment, a method promotes axonal regeneration and remyelination repair of a peripheral nerve. The method directly contacts a target peripheral nerve or target distal branch thereof with a direct-contact electrode that is insulated to confine current to the target nerve. The direct-contact electrode is configured to couple to a nerve having a diameter of between 1 mm and 25 mm. Pulse trains are delivered to the target nerve. Each pulse train has pulses having a frequency between about 20 Hz and 100 Hz and a pulse width between 150 microseconds and 500 microseconds. The pulse trains have a train duration between about 3 seconds and 60 seconds and are separated by rest intervals between about 0.5 minute and 5 minutes. The stimulation amplitude is titrated relative to a threshold appropriate for the nerve type, comprising at or above contraction threshold for a motor nerve, at or above sensation threshold for a sensory nerve, or at or above a physiological threshold for an autonomic nerve. The pulse trains are delivered in 1 to 8 pulse trains per session, in at least one session per day, on 3 to 7 days per week, for at least 2 weeks up to 20 weeks. Accordingly, the method initiates axonal regeneration and/or promotes remyelination repair in the target nerve.

In accordance with yet another embodiment, a method for promoting axonal regeneration and remyelination repair of a peripheral nerve includes directly contacting a target peripheral nerve with a stimulation electrode, where the nerve has a diameter between about 1 mm and about 25 mm. The method involves selectively delivering biphasic electrical stimulation to the nerve using pulse trains while the electrode remains in direct contact. The stimulation is applied at or above a contraction threshold sufficient to activate motor units of the target nerve. Each individual pulse within a pulse train has an amplitude between about 0.1 mA and about 10 mA, a pulse width between about 150 microseconds and about 500 microseconds, and an interphase interval between about 25 microseconds and about 100 microseconds. The pulses within each train are delivered at a frequency between about 20 Hz and about 100 Hz, and each pulse train lasts between about 3 seconds and about 60 seconds. At least one pulse train is delivered per therapy session, with successive trains separated by a rest interval of about 0.5 minutes to about 5 minutes. Between about 1 and about 10 therapy sessions are performed per day, on between about 1 and about 7 days per week.

In various embodiments, the method further includes delivering electrical stimulation in a manner that initiates axonal regeneration and/or promotes remyelination repair of the peripheral nerve, while improving at least one functional outcome such as increased urethral closure pressure, reduced urinary leak count, improved fecal continence, or enhanced organ-specific physiological metrics. Selectivity of stimulation is demonstrated by the absence of off-target activation, for example, no external anal sphincter activation when targeting the perineal nerve, no urethral closure activation when targeting the inferior rectal nerve, and no diffuse pelvic contractions indicative of pudendal trunk activation.

In some embodiments, the target nerve is a motor nerve, and the stimulation amplitude is set at or above the contraction threshold, defined as the minimum intensity that produces a visible or palpable contraction of the muscle innervated by the target nerve. In other embodiments, the target nerve is a sensory nerve, and the amplitude is set at or above the sensation threshold. For autonomic nerves, the amplitude is set at or above a physiological threshold, defined by a minimal measurable change in an organ-specific marker such as heart rate, blood pressure, regional blood flow, or respiratory rate. If contraction threshold cannot be determined, the stimulation amplitude is set at or above an electromyographic (EMG) threshold, defined as the minimum intensity that elicits a detectable EMG signal in the target muscle. The method may also include progressively adjusting stimulation amplitude over the course of therapy as thresholds change due to nerve regeneration or remyelination, while maintaining stimulation within safe limits below a pain threshold. In certain embodiments, the amplitude remains less than 10% above the applicable threshold.

The methods may further include using a direct-contact electrode configured to couple with a nerve having a diameter smaller than 1 mm, optionally between about 0.2 mm and 1 mm, with stimulation amplitude adjusted toward the lower end of a safe range to achieve threshold activation without exceeding charge density limits. In some embodiments, the electrode is positioned in proximity to, but not in direct physical contact with, the target nerve, such proximity being within about 0.5 mm to 5 mm or within about 50% of the nerve diameter, enabling selective depolarization of the target nerve at a stimulation amplitude within a clinically acceptable safety window and without activating adjacent nerves. The proximity may be expressed as a ratio relative to nerve diameter, optionally less than or equal to 100% of the nerve diameter and may be less than or equal to 50%. In certain configurations, the electrode array includes multiple contacts arranged to enable spatial current steering and selective activation of the target nerve while avoiding activation of adjacent nerves under the same stimulation conditions.

The method may also include applying parameter guardrails such as amplitude limits, pulse width constraints, and duty cycle restrictions to reduce off-target activation and maintain safety margins. Additionally, the controller may dynamically adjust electrode selection and stimulation amplitude based on sensed signals indicative of nerve activation or off-target recruitment. Stimulation amplitude may be scaled to nerve diameter, such that nerves smaller than 1 mm are stimulated at about 0.1 mA and nerves up to 25 mm at about 3 mA. For direct-contact configurations, stimulation amplitude remains within a range of about 0.1 mA to 3 mA to maintain effective depolarization while minimizing charge density and energy consumption.

Various embodiments deliver stimulation in structured sessions with no more than eight pulse trains per session, each train lasting between about 3 seconds and 60 seconds, and total session duration maintained below one hour to reduce fatigue and conserve device power. The stimulation waveform consists of biphasic pulses designed to maintain charge balance and minimize electrode polarization, with the biphasic waveform optionally including a recovery phase configured to achieve a charge injection safety index below about 1.8. In certain embodiments, the stimulation device is positioned on a distal branch of a pelvic nerve, such as the perineal nerve, inferior rectal nerve, or levator ani motor branch, to selectively activate motor fibers responsible for continence or pelvic support. The electrode housing may include an insulating body that shields adjacent nerve branches and confines current to targeted fascicles, reducing off-target activation. Parameter guardrails may be applied to limit amplitude, frequency, and pulse train architecture to levels sufficient for on-target activation but insufficient to activate adjacent branches under therapeutic conditions.

Among other ways, on-target activation can be confirmed by physiological markers such as visible or palpable muscle contraction, electromyographic activity in the target muscle, or organ-specific functional responses, while off-target absence is verified by confirming no activation of adjacent nerves through lack of secondary muscle contractions or physiological changes in non-target organs. Objective outcomes of therapy may include improved urethral closure pressure, increased anal squeeze pressure, reduced stress urinary incontinence episodes, reduced fecal incontinence episodes, or improved pelvic organ prolapse scores. In some embodiments, the target nerve is an autonomic nerve such as the renal nerve, cavernous nerve, or vagus nerve, with stimulation amplitude titrated to a physiological threshold defined by measurable organ-specific responses including changes in blood flow, urine output, or heart rate. Stimulation amplitude may also be scaled according to nerve diameter and patient-specific threshold feedback, such that smaller nerves of about 1-3 mm are stimulated at amplitudes of about 0.6-1.0 mA and larger nerves up to 25 mm at amplitudes up to about 3 mA.

Illustrative embodiments may adjust stimulation amplitude downward after implantation as thresholds decrease due to tissue stabilization and fibrotic encapsulation, maintaining effective activation while minimizing fatigue and energy consumption. Stimulation may comprise pulse bursts lasting about 3-60 seconds at a frequency of 20-100 Hz and a pulse width of 150-500 μs, with rest intervals of about 0.5-5 minutes between bursts and no more than eight bursts per session to keep total session duration under one hour. When threshold determination is impractical, stimulation parameters may be applied within a default safe range of amplitude between about 0.1 mA and 10 mA, frequency between about 20 Hz and 100 Hz, and pulse width between about 150 μs and 500 μs, with adjustments based on patient feedback indicating discomfort or fatigue. Patient feedback may include subjective reports of pain or exhaustion and/or objective indicators of muscle fatigue, prompting reductions in amplitude, frequency, or duty cycle while maintaining safety limits. In some embodiments, stimulation is delivered using a non-direct contact electrode positioned near the target nerve or a neurovascular bundle, such that stimulation occurs through intervening tissue while maintaining selectivity.

The electrode may be positioned so that the shortest tissue path between the stimulating pole and the target nerve is less than about 1.5 mm and shorter than the path to any adjacent non-target nerve. Nerve-specific thresholds may be confirmed by observing physiological markers such as visible or palpable muscle contraction, patient-reported sensation, or organ-specific functional changes. When patient feedback is unavailable, fallback thresholding may be applied by delivering stimulation at a predetermined amplitude derived from intraoperative measurements or device-specific lookup values for nerve size and configuration.

Various embodiments may further periodically reassess activation thresholds during a multi-week therapy regimen and adjusting stimulation amplitude upward or downward based on changes in nerve excitability or tissue impedance. Threshold reassessment may occur at defined intervals or upon detection of threshold drift, with dynamic titration to remain at or slightly above the functional threshold while maintaining safety limits. Dynamic adjustment may involve reducing amplitude as nerve conduction improves during regeneration or remyelination and increasing amplitude when impedance rises due to fibrosis or scar tissue formation. The controller may automatically modify stimulation parameters-including amplitude, train duration, and train count, e.g., based on sensed biomarkers indicative of threshold change, fatigue, or functional recovery. In some embodiments, the neuromodulation device is configured for long-term implantation to deliver chronic stimulation over months or years following initial nerve repair, with schedules adaptively adjusted based on patient response and disease progression. The therapy may also be applied to mitigate recurrent demyelination associated with autoimmune disorders such as multiple sclerosis by promoting remyelination and preserving nerve conduction in intact neurons. Finally, the implanted device may limit cumulative stimulation time per day and per week to extend device longevity and reduce recharge frequency while maintaining therapeutic efficacy.

In some embodiments, modifying the stimulation parameters includes adjusting one or more parameters across multiple therapy sessions in response to longitudinal changes in the biosignals. These stimulation parameters may include amplitude, frequency, pulse duration, train duration, the number of stimulation trains per session, or the frequency of therapy sessions.

The stimulation may be configured for a maximum of eight pulse trains per session and maintaining session duration under one hour during chronic use. Stimulation may be delivered to achieve selective activation of a single physiological target, such as one muscle, one sensory dermatome, or one autonomic organ, or semi-selective activation of two or three related targets within a functional region. In some embodiments, stimulation achieves myoselective activation of a single muscle or a physiologically meaningful subset of its fibers, dermatoselective activation of a single sensory dermatome or sub-region, or visceroselective activation of a single autonomic organ or defined sub-portion without activating additional systems.

Selectivity may be enhanced by positioning the stimulation device at a distal branch of the target nerve to reduce fascicular complexity and minimize off-target activation compared to proximal placements. Stimulation amplitude for selective activation using direct-contact electrodes may be maintained within about 0.1 mA to 3 mA, with frequency between 40 Hz and 80 Hz and pulse width between 150 and 300 microseconds. Amplitude may range from ≥0.1 mA to ≤2 mA and, for motor nerves, remain above the contraction threshold. Each pulse train may last between 10 and 20 seconds, with rest intervals of 2 to 4 minutes, and total stimulation duration per session between 15 and 60 seconds. Therapy may include 1 to 2 sessions per day, performed 5 to 7 days per week, for at least 4 weeks and up to 12 weeks. The pulse waveform may be biphasic and charge-balanced with a recovery ratio of 1:1 or 1:2, and each train may begin with a ramping envelope comprising a gradual amplitude increase over 0.2 to 3 seconds. Pulses may use square, triangular, sawtooth, or sinusoidal waveforms.

In various embodiments, fatigue is avoided by separating trains with rest intervals and maintaining amplitude below pain and tolerability thresholds. A progressive regimen may increase train duration, number of trains per session, or frequency within the disclosed ranges over a multi-week course while maintaining amplitude relative to threshold. Selectivity may be confirmed by absence of specified off-target responses, such as no external anal sphincter contraction when targeting a perineal nerve or no urethral closure pressure rise when targeting an inferior rectal nerve. The peripheral nerve may have a diameter between about 1 mm and 3.5 mm, and the method may apply to injury grades from neurapraxia (Grade 1) to axonotmesis (Grade 2) and higher, initiating axonal regrowth and promoting Schwann-cell remyelination.

In accordance with another embodiment, a neurostimulation system is configured to promote axonal regeneration and remyelination repair of a peripheral nerve. The system includes an electrode sized to couple to a peripheral nerve or its distal branch, defining a target nerve with a diameter between about 1 mm and 25 mm. The electrode may incorporate insulation configured to confine current to the target nerve. The system further includes a controller programmed to deliver charge-balanced biphasic pulse trains with a frequency between about 20 Hz and 100 Hz, a pulse width between about 150 microseconds and 500 microseconds, an interphase interval between about 25 microseconds and 100 microseconds, and a train duration between about 3 seconds and 60 seconds, separated by rest intervals of about 0.5 minutes to 5 minutes. Stimulation is delivered in one or more pulse trains per session, at least one session per day, on 1 to 7 days per week, for a duration of at least 2 weeks and up to 20 weeks. The controller is further configured to set amplitude relative to a threshold appropriate for the nerve type, including at or above contraction threshold for a motor nerve, below or near sensation threshold for a sensory nerve, or at a physiological threshold for an autonomic nerve.

The neurostimulation system may provide stimulation with a recovery ratio of 1:1 or 1:2 while maintaining charge balance. The controller can apply a ramping envelope at the start of one or more pulse trains to gradually increase amplitude. The system may include a user interface configured to display or record threshold determinations such as contraction threshold, sensation threshold, and physiological threshold. The electrode may be implemented as a clip or cuff and include a conformal insulating body to reduce volume conduction to off-target nerves. The system may also include sensing circuitry capable of detecting electromyographic activity associated with the target muscle without implementing closed-loop control.

In some embodiments, the method treats fecal incontinence by targeting the inferior rectal nerve, delivering stimulation that increases anal squeeze pressure and reduces fecal incontinence episodes, with off-target absence confirmed by no urethral closure pressure rise at therapeutic amplitudes. Another embodiment initiates axonal regeneration by directly contacting the nerve with a direct-contact electrode and delivering one or more pulse trains totaling less than one minute of on-time, each train comprising pulses at 20-100 Hz and 150-500 microseconds, at an amplitude at or above contraction threshold for a motor nerve. A further embodiment modulates an autonomic nerve—such as vagus, cardiac, renal, cavernous, or hepatic—by delivering charge-balanced biphasic pulse trains while titrating amplitude to a physiological threshold indicated by minimal, reproducible changes in organ-specific metrics like heart rate, blood pressure, regional blood flow, or respiratory rate, without exceeding pain or tolerability limits.

The method or system may scale amplitude according to nerve diameter ranges such as 1-2 mm, 1.5-3.5 mm, 2-3 mm, or 2.7-4.7 mm. Waveform shapes may include square pulses or alternatives such as triangular, sawtooth, or sinusoidal. The controller enforces charge density or current density limits normalized to electrode contact area. Outcome validation may involve periodic measurement of urethral closure pressure, leak point pressure, fecal continence scores, voiding efficiency, or organ-specific physiological metrics, with parameter adjustments responsive to outcomes while maintaining amplitude relative to threshold. When primary threshold markers are unavailable, amplitude may initially be set by default scaling based on nerve diameter and type, within the disclosed ranges, and later refined by objective outcomes. The user interface may record clinician-observed contractions, patient-reported sensations, and physiological markers, and store telemetry such as train durations, rest intervals, amplitudes, and session counts. Finally, initiating axonal regeneration and/or promoting remyelination repair in the target nerves improves functional outcomes such as increased urethral closure pressure, reduced leaks, improved voiding efficiency, reduced fecal incontinence episodes, and enhanced organ-specific physiological metrics.

The recorded biosignals may include electromyographic (EMG) or electroneurographic (ENG) signals, and the adjustments to stimulation may be based on signal characteristics such as response latency, signal amplitude, or signal stability.

In further embodiments, the method includes independently modifying stimulation to a first pelvic nerve relative to a second pelvic nerve based on differences in muscle activation or recovery. For example, stimulation delivered to the second nerve may be increased while stimulation to the first nerve is reduced in response to detected signs of fatigue or overstimulation in the first nerve's corresponding muscle.

The stimulation pattern may also be progressively intensified if the recorded biosignals indicate improved muscle recruitment or activation. This may be demonstrated through improvements such as reduced response latency, increased amplitude of biosignals, or increased strain response.

In some implementations, the method includes adjusting the timing or intensity of therapy delivery to prevent or minimize muscle fatigue, overstimulation, or neuromuscular imbalance.

A method of treating a pelvic health disorder includes electrically coupling a neuromodulation device to a nerve target that directly or reflexively innervates a target muscle, and stimulating the nerve target using the neuromodulation device. In some embodiments, stimulating the nerve includes delivering a probe stimulation to the nerve target, detecting a physiological response evoked by that probe stimulation, and using the evoked response as closed-loop feedback to adjust stimulation parameters for future therapy.

Coupling the neuromodulation device may involve positioning the device along the last quarter or last third of the length of the target nerve. In some embodiments, the device is coupled to a portion of the nerve having between one and three fascicles. The neuromodulation device may include a multi-input, single-output (MISO) proportional-integral-derivative (PID) controller.

The neuromodulation device may include a hermetically sealed housing containing electronics, surrounded by a buffer layer, and include an elastomeric arm that defines a nerve channel along a longitudinal axis. The system may include a nerve stimulation chamber defined in part by the arm, and the chamber may retain a nerve in contact with an internal electrode.

In some embodiments, the method includes reducing the maximum cross-sectional dimension of a nerve to create a stretched, narrowed nerve; advancing the stretched nerve through the channel where wall pressure remains below 6.7 kPa at any point; positioning the nerve in the stimulation chamber; allowing it to expand; and maintaining at least 20% of the nerve's perimeter in contact with the electrode.

In accordance with yet another embodiment, a nerve stimulation device may include a clip-like nerve engagement structure sized to partially surround a peripheral nerve with an average diameter between about 1.0 mm and 3.0 mm. First and second electrodes are disposed on the inner surface of the structure and electrically isolated from each other by an insulating body, with the electrodes coupled to a pulse generator through hermetic feedthroughs. The interelectrode distance is between about 2.5 mm and 3.5 mm. The device is configured for active-return biphasic stimulation, where current flows between the first and second electrodes through adjacent nerve tissue, and the total device width measured laterally across the electrodes and outboard insulation is less than or equal to about 6 mm.

A method of promoting nerve regeneration in a patient includes positioning a nerve stimulation device adjacent to a peripheral nerve and delivering electrical stimulation in the form of pulse bursts, each burst lasting between about 3 and 60 seconds. The number of pulse bursts per therapeutic session is limited to fewer than eight, and the total stimulation time per session is maintained below one hour. Sessions are repeated at a frequency of one or fewer per day for a period of at least two weeks. The stimulation is configured to maintain amplitudes within safety limits and avoid continuous or event-driven activation, thereby reducing muscle fatigue and conserving device energy while promoting nerve repair.

In some embodiments, promoting nerve regeneration includes positioning a nerve stimulation device in direct contact with a distal branch of a peripheral nerve so that the device engages a single physiological target or a physiologically meaningful sub-portion thereof. The physiological target may comprise one anatomically recognized muscle or a defined group of myofibers within that muscle, a single sensory dermatome or a sub-region of that dermatome, or a single autonomic organ or a defined sub-portion of that organ. Electrical stimulation is delivered through at least one electrode of the device using biphasic pulses at a frequency of about 20-100 Hz, a pulse width of about 100-500 microseconds, and a pulse burst duration of about 3-60 seconds. Said pulse bursts are repeated in a quantity of fewer than eight per therapeutic session, with rest intervals of about 0.5-5 minutes between bursts, such that the total session duration remains less than one hour. Stimulation amplitude is titrated to a threshold sufficient to depolarize the target without activating additional physiological targets, thereby achieving selective stimulation while minimizing off-target activation and preserving safety limits.

The method of treating stress urinary incontinence may involve selectively stimulating the perineal nerve at a precise position to activate an efferent motor pathway associated with a single pelvic floor muscle or a defined subset of its myofibers. Similarly, a method of treating overactive bladder may selectively stimulate the perineal nerve to activate an afferent sensory pathway associated with a single proprioceptive sensory territory or sub-region. For fecal incontinence, selective stimulation may target the inferior rectal nerve to activate an efferent pathway associated with the external anal sphincter or a defined subset of its fibers. In each case, stimulation is delivered as a burst of monophasic or biphasic pulses at a frequency of about 20-100 Hz, a pulse width of about 150-500 microseconds, and a burst duration of about 3-60 seconds, with activation limited to a single physiological target.

Semi-selective stimulation methods may activate no more than two or three physiological targets within a related anatomical region, such as multiple pelvic floor muscles for stress urinary incontinence, two or three sensory territories for overactive bladder, or two or three anorectal muscular targets for fecal incontinence. These methods use similar stimulation parameters but ensure activation does not exceed three physiological targets. Stimulation may be delivered through an electrode in direct conductive contact with the nerve or via a non-contact electrode transmitting energy across tissue. Pulse bursts are separated by rest intervals of about 0.5-5 minutes, with total session duration less than one hour.

A neuromodulation device for treating pelvic health disorders may include a stimulation electrode configured for direct contact with a target peripheral nerve or distal branch to achieve selective activation of a single physiological target, such as a pelvic floor muscle, sensory dermatome, or autonomic organ. The controller delivers biphasic pulses with a pulse width of about 150-500 microseconds, a frequency of about 20-100 Hz, and pulse bursts lasting about 3-60 seconds, separated by rest intervals of about 0.5-5 minutes. Amplitude is current-controlled between about 0.1 mA and 10 mA, scaled to nerve size and titrated relative to threshold, with no more than eight bursts per session and total session duration under one hour.

Device-specific features may include multiple electrodes with an interelectrode distance of about 2.5-3.5 mm, each electrode having a width of about 0.4-0.6 mm and an exposed length of up to about 6.5 mm. Outboard insulation may extend laterally beyond each electrode by at least 0.5 mm, or about 1.0 mm, to limit current leakage. Electrodes may comprise platinum-iridium alloy (preferably 90-10 Pt—Ir) or gold, and the insulating body may be silicone or polyimide. The device is configured to deliver biphasic, charge-balanced stimulation with a per-phase charge density of $\leq 20\ \mu C \cdot cm^{-2} \cdot ph^{-1}$ at up to 2 mA and 250 microseconds per phase, maintaining a Shannon k parameter$\leq 0.90$. The ratio of interelectrode distance to nerve diameter may range from about 1.0 to 2.5, preferably 1.3 to 2.0. Feedthrough electrodes may provide both mechanical anchoring and electrical continuity to a hermetically sealed electronics enclosure.

Outcome validation may include periodic measurement of urethral closure pressure, leak point pressure, fecal continence scores, voiding efficiency, or organ-specific physiological metrics, with parameter adjustments responsive to outcomes while maintaining safety limits. When primary threshold markers are unavailable, amplitude may be initially scaled by nerve diameter and type, then refined by objective outcomes. The user interface may record clinician-observed contractions, patient-reported sensations, and physiological markers, along with session telemetry such as train durations, rest intervals, amplitudes, and session counts.

The device may include electrodes providing a contact surface area of about 2.5 $mm^2$ to 4 $mm^2$. The nerve-engagement structure may be configured to cover at least 50% of the nerve circumference, and preferably at least 80% and up to 100%. The device may further comprise a hermetic enclosure housing pulse-generation circuitry, power management electronics, and a rechargeable power source, with the enclosure connected to the nerve-engagement structure via an implanted lead. The device may include an inductive recharge coil designed to receive transcutaneous energy from an external transmitter and relay it to the internal power source. In some embodiments, the nerve-engagement structure is configured as a clip or cuff adapted for implantation at anatomically constrained sites, including nerves with diameters between about 1 mm and 5 mm. The electrodes may be formed as conductive feedthrough structures extending from the hermetic enclosure to provide both structural anchoring and electrical continuity.

Illustrative embodiments applicable to the field of nerve stimulation and nerve recording and are applicable to sensory, motor and autonomic nerves within humans and animals.

Illustrative embodiments of the invention are implemented as a computer program product having a computer usable medium with computer readable program code thereon. The computer readable code may be read and utilized by a computer system in accordance with conventional processes.

BRIEF DESCRIPTION OF THE DRAWINGS

Those skilled in the art should more fully appreciate advantages of various embodiments of the invention from the following "Description of Illustrative Embodiments," discussed with reference to the drawings summarized immediately below.

FIGS. 3A-3M schematically show details of various embodiments of neuromodulation devices in accordance with illustrative embodiments.

FIGS. 3N-3O schematically show a system for neuromodulation in accordance with illustrative embodiments.

FIG. 7 shows quantitative histological analyses demonstrating cellular and axonal changes in nerves subjected to chronic stimulation following a crush injury in accordance with illustrative embodiments.

Figure 1A:
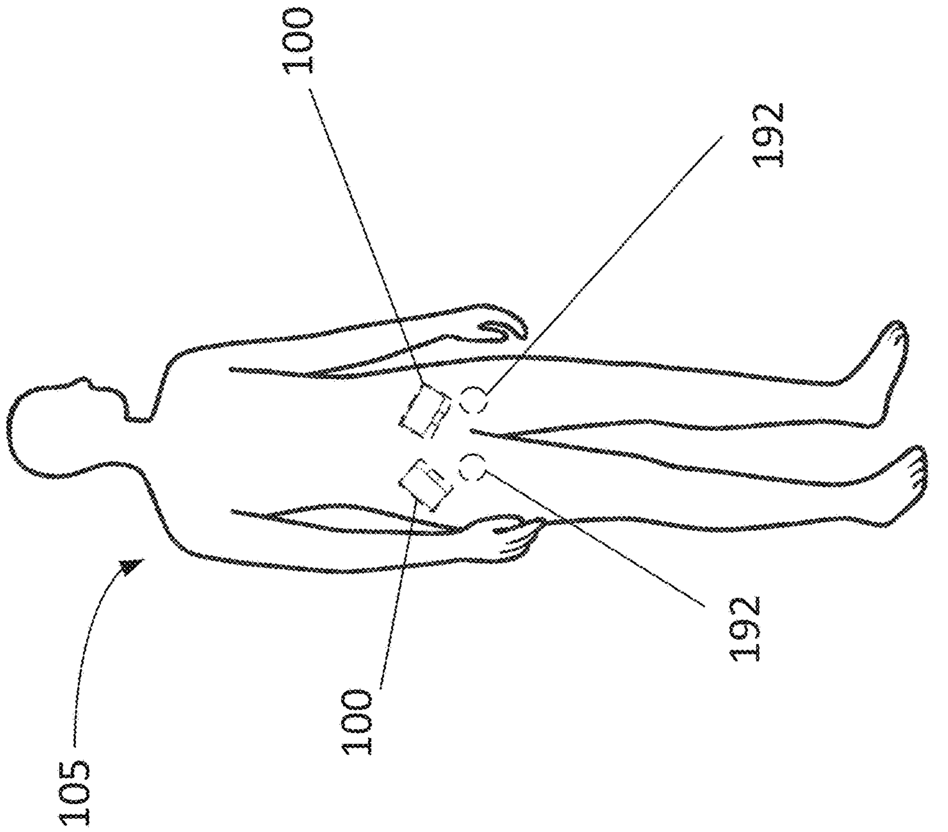
FIG. 1A schematically shows a patient in accordance with illustrative embodiments.

It should be noted that the foregoing figures and the elements depicted therein are not necessarily drawn to consistent scale or to any scale. Unless the context otherwise suggests, like elements are indicated by like numerals. The drawings are primarily for illustrative purposes and are not intended to limit the scope of the inventive subject matter described herein.

DESCRIPTION OF ILLUSTRATIVE EMBODIMENTS

In illustrative embodiments, peripheral nerves are regenerated and/or remyelinated through selective electrical stimulation delivered via electrodes (e.g., direct contact electrodes). Illustrative embodiments advantageously address limitations of conventional approaches that rely on prolonged continuous stimulation or non-selective transcutaneous methods, which are clinically impractical and lack precision. By applying multiple sessions of short-duration, above-threshold pulse trains, illustrative embodiments initiate axonal regrowth and support Schwann cell-mediated remyelination, restoring nerve conduction and improving associated physiological functions. Furthermore, applying selective stimulation using direct-contact electrodes directs stimulation energy toward the target nerve and minimizes unintended activation of off-target nerves or surrounding tissue. This focused approach enhances therapeutic precision, reduces side effects, and improves overall efficiency compared to remote or stimulation schemes that are not direct-on-nerve (paddle electrode arrays, electrode arrays along the length of the lead, or similar).

Illustrative embodiments provide stimulation protocols tailored to nerve type and size, including motor, sensory, and autonomic nerves. For motor nerves, stimulation is delivered at or above contraction threshold; for sensory nerves, at or above sensation threshold; and for autonomic nerves, at a physiological threshold determined by organ function markers. These parameters are optimized for peripheral nerves such as the pudendal, perineal, inferior rectal, and levator ani nerves, as well as broader applications to limb and autonomic nerves. Illustrative embodiments further encompass embodiments for treating conditions such as stress urinary incontinence, overactive bladder, fecal incontinence, pelvic organ prolapse, sexual dysfunction, and autonomic dysfunctions.

Various embodiments employ stimulation frequencies between approximately 20 Hz and 100 Hz, pulse widths of 100-400 microseconds, and amplitudes above threshold but within safe limits. Pulse trains of 5-30 seconds are repeated with rest intervals of 1-5 minutes, in sessions delivered multiple times per week over a period of weeks. Alternative embodiments include single-session intraoperative stimulation to initiate regeneration, chronic therapy for enhanced remyelination and functional recovery, and optional configurations using biodegradable or temporary transcutaneous electrodes. Illustrative embodiments support waveform flexibility, including biphasic pulses with adjustable recovery ratios to maintain charge balance. Details of illustrative embodiments are discussed below.

FIG. 1A schematically illustrates a patient 105 in accordance with illustrative embodiments. The patient 105 has undergone a minimally invasive surgical procedure to implant one or more neuromodulation devices 100 and, optionally, one or more sensors 192. In various embodiments, the neuromodulation devices 100 are configured to stimulate one or more nerves within the patient's body. Nerves serve as natural conduits, analogous to electrical wires, that transmit electrochemical signals between the central nervous system (CNS) and peripheral structures such as organs, glands, and muscles. These signals may be autonomic (unconsciously controlled) or somatic (consciously controlled), and they enable both sensory perception and motor function.

Over time, the integrity of these neural communication pathways can degrade due to injury, disease, or aging. For example, damage may occur to the nerve itself (as in demyelinating or inflammatory diseases such as multiple sclerosis, acute-disseminated encephalomyelitis, neuromyelitis optica spectrum disorder, Guillain-Barre syndrome, mechanical damage such as compression or stretch injury, or other nerve injury), to the neuromuscular junction, or to the effector tissue (e.g., a muscle or organ) innervated by the nerve. Such damage may impair the propagation or interpretation of nerve signals, resulting in reduced or erratic neural conductance. Clinical manifestations can include loss of muscle control, diminished sensitivity, tingling, or chronic pain. Illustrative embodiments address these issues through implantation of one or more nerve stimulation devices 100 configured to improve nerve activity.

In some embodiments, each neuromodulation device 100 receives stimulation instructions from a controller. The controller can be implemented as an on-device processor integrated within the implanted stimulator, or alternatively, as part of an external computing device, such as a clinician programmer or tablet located in a doctor's office. In some embodiments, one controller may control one more of the devices 100 (e.g., in a satellite arrangement). The stimulator 100 can be programmed or reprogrammed to tailor stimulation parameters to the individual's physiological response and therapeutic goals.

The neuromodulation device 100 may be implanted following a short surgical procedure. As will be discussed further below, a variety of different stimulators may be used depending on the target nerve, anatomical access, and treatment indication. Each stimulator may include a direct contact electrode configured to physically engage the target nerve, allowing for highly specific delivery of stimulation energy. In various embodiments, the stimulator is designed as a miniaturized clip that can mechanically couple to peripheral nerves as small as 1 millimeter in diameter. By directly coupling to the nerve, the system achieves precise stimulation with minimal or no detectable off-target activation of adjacent nerves or tissues.

As used herein, the term "diameter" does not require the nerve or nerve target to have a circular cross-section. Rather, "diameter" refers to a characteristic dimension of the nerve, such as a maximum cross-sectional dimension in an undeformed state. Accordingly, "diameter" provides a size measure without necessarily requiring any particular shape, geometry, or continuity of the cross-section. The term "diameter" may be used interchangeably with "maximum cross-sectional dimension in an undeformed state."

In various embodiments, the device may be configured to selectively stimulate nerves with diameters smaller than 1 mm, including nerves as small as 0.5 mm or even 0.2 mm, for example, in veterinary or specialized applications. This capability is enabled by the clip-like engagement structure and direct-contact electrode design, which can be scaled to maintain precise electrode positioning and insulation margins even at micro-scale dimensions. By reducing the overall device footprint and optimizing electrode spacing and width, the system ensures effective stimulation without off-target activation.

The stimulation parameters described herein remain applicable for these smaller nerves, with amplitudes adjusted toward the lower end of the safe range (e.g., ≥0.1 mA) to achieve threshold activation without exceeding charge density limits. Empirical evidence and engineering analysis indicate that regenerative effects such as axon repair and remyelination can 'be achieved at these reduced amplitudes, provided that stimulation is delivered in structured bursts with appropriate train-and-rest intervals. Illustrative embodiments thus are able to address a broader range of anatomical targets, including fine peripheral nerves in both human and veterinary contexts.

In some embodiments, the stimulation device 100 may not be in direct physical contact with the target nerve, but may be positioned in proximity sufficient to achieve selective depolarization of the intended nerve fibers without activating adjacent nerves.

For peripheral nerves with diameters typically ranging from 1 mm to 5 mm, the electrode may be positioned within a range of 0.5 mm to 5 mm from the outer epineurium of the target nerve. This range ensures that the electric field remains localized and efficient while avoiding excessive current requirements that could compromise safety. In some embodiments, the distance is expressed as a ratio relative to nerve diameter, such as ≤100% of the nerve diameter, and ≤50% of the nerve diameter.

In addition to physical proximity, the electrode placement is characterized by its ability to achieve threshold depolarization of the target nerve at a stimulation amplitude within a clinically acceptable safety window. For example, the electrode should enable activation of the target nerve at currents that do not exceed the charge injection safety index (e.g., channel safety index<1.8) and remain within the electrode's charge injection capacity. This functional criterion ensures that the electrode is "near" in a practical sense, such that it is close enough to stimulate the nerve effectively without requiring unsafe levels of current. Additionally, the non-contact electrode can stimulate selectively, such that it avoids triggering an action potential or reaching threshold in any adjacent off-target nerve under the same stimulation conditions. This ensures that the electric field is sufficiently focused to target only the intended nerve fibers.

The sensors 192, shown positioned near the lower extremities, may be configured to detect physiological parameters such as muscle activity, motion, or bioelectrical signals associated with neural activity. The data acquired from sensors 192 can be transmitted to the controller, which in turn adjusts stimulation parameters in real time, enabling closed-loop neuromodulation.

Collectively, the system shown in FIG. 1A represents a patient-implant configuration that enables targeted, programmable, and adaptive neuromodulation therapy for repairing or modulating nerve function.

Figure 1B:
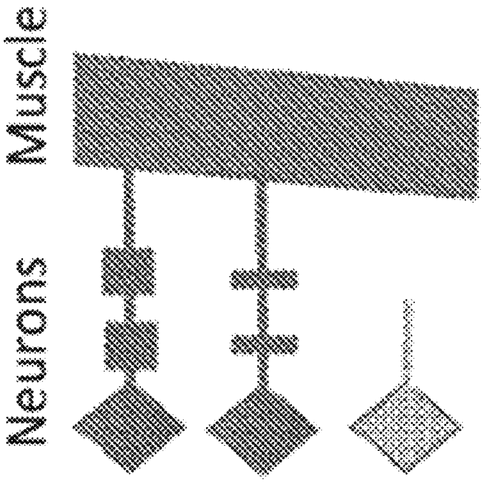
FIG. 1B schematically shows various stages of peripheral nerves in accordance with illustrative embodiments.
Figure 1C:
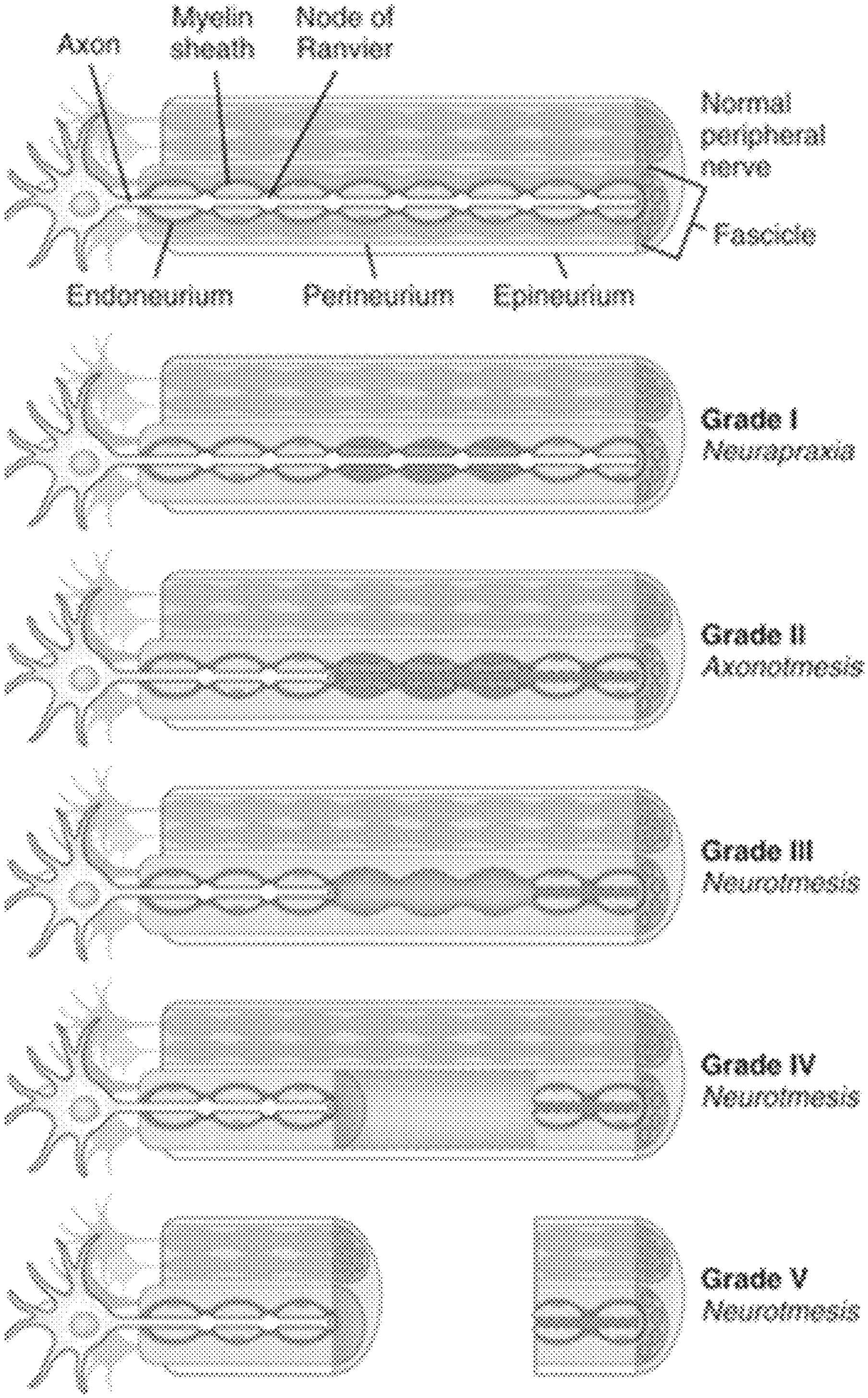
FIG. 1C illustrates the various grades of peripheral nerve injury that may be treated using illustrative embodiments.

FIG. 1B-1C schematically shows various stages of peripheral nerve injuries in accordance with illustrative embodiments. Peripheral nerves can be damaged by traction or stretch during childbirth or surgery, compression or ischemia, laceration and transection, or inflammatory and demyelinating conditions. From a structural standpoint, injuries range from neurapraxia (conduction block without axonal discontinuity) through axonotmesis (axonal loss with intact connective tissues) to neurotmesis (complete transection with connective tissue disruption). After axonal interruption, the distal segment undergoes Wallerian degeneration, Schwann cells lose axonal contact, transition to a repair phenotype, proliferate, and form longitudinal bands that guide new axonal sprouts. Where myelin is primarily affected (demyelination), conduction slows or fails despite axonal continuity.

Functionally, these injuries can manifest as reduced or absent motor activation of target musculature (e.g., diminished urethral closure pressure in *SUI*) or aberrant sensory/organ control (e.g., urgency symptoms, fecal leakage). Without targeted intervention, recovery is often incomplete or protracted, and muscle secondary changes (atrophy or maladaptive remodeling) can limit functional restitution even when axonal continuity is eventually re-established.

As used herein, regeneration refers to axonal regrowth that restores continuity of injured neurons across an injury zone (e.g., after axonotmesis or partial fascicular disruption). Remyelination repair refers to Schwann cell-mediated restoration of myelin, improving conduction along intact or newly regenerated axons (e.g., after neurapraxia or following successful axonal regrowth). The term repair may be used as an umbrella encompassing both axonal regeneration and remyelination; however, where precision is desired, axonal regeneration is distinguished from remyelination repair as coordinated but separable processes. For example, a particular neuron may be regenerated to restore axon growth, and then the regenerated axon may be remyelinated.

Injury grades can be mapped to these processes: demyelinating injuries (e.g., neurapraxia) primarily require remyelination repair, whereas axonal injuries (e.g., axonotmesis and higher grades) require axonal regeneration followed by remyelination. Electrical activity is a common driver for both, promoting neuronal regeneration and recruiting Schwann cells to remyelinate newly re-established axons.

Illustrative embodiments advantageously repair a target nerve. Among other ways, repair can be determined from objective changes in target function. For urinary indications, metrics include urethral closure pressure, leak point pressure, voiding efficiency/capacity, frequency of leaks, and validated patient-reported outcomes (voiding diaries, symptom questionnaires). For fecal indications, fecal incontinence episodes and continence scales are applicable. For autonomic targets (e.g., vagus/cardiac/renal/cavernous), organ-specific physiologic markers (heart rate modulation, blood pressure, blood flow, respiration rate, temperature, gastrointestinal functional indices, sexual function indices) serve as thresholds and outcome measures.

For motor nerves, contraction threshold (visible or palpable muscle contraction) indicates that stimulation is at or above the functional recruitment level for motor units; EMG thresholds may occur below visible contraction and can be used in sedated settings or when contractions are weak or not observable. In sensory nerves, sensation threshold (non-pain perception) is relevant; in autonomic nerves, a physiological threshold is defined by organ response (e.g., heart rate change).

Tissue analyses can also demonstrate increased axonal density, the presence of newly myelinated fibers (often exhibiting thinner myelin characteristic of early remyelination), elevated Schwann cell counts, and improved fascicular organization-features consistent with axonal regeneration and remyelination. These histological findings complement functional assessments and electrophysiologic endpoints. In various embodiments, nerve conduction studies (NCS) or analogous electrophysiologic measurements may be used to evaluate recovery of the nerve fiber, including assessments of conduction velocity, latency, amplitude, or signal propagation across the repair site. Together, these structural and functional measures substantiate the biological basis of nerve healing and support the observed improvements in physiologic function.

Illustrative embodiments repair a target nerve by providing selective, direct-contact stimulation of peripheral nerves using short-duration, above-threshold pulse trains with defined rest intervals, repeated over days to weeks. In various embodiments for motor nerves, stimulation is delivered at or above contraction threshold. For sensory targets, stimulation is delivered at or above sensation threshold. For autonomic targets, stimulation is delivered at a physiological threshold tied to organ function. Typical parameter windows include frequencies of about 20-100 Hz, pulse widths of about 100-500 μs, train durations of about 3-60 seconds, pulse trains of between 1-8, rest intervals of about 0.5-5 min between trains, ≥1 session per day, 3-7 days per week, for ≥2-20 weeks. Amplitudes are above threshold yet maintained within comfort/safety limits (e.g., ≤0.1 mA lower bound to cover small distal nerves, ≤~2 mA upper bound in many pelvic applications, and could be higher than 5 mA for the largest motor nerves).

The device may be configured for long-term implantation to support chronic stimulation protocols extending beyond the initial nerve repair period. While many applications achieve functional recovery within weeks of therapy, the inventors believe that some clinical scenarios may benefit from months or even years of ongoing stimulation. For example, patients with autoimmune-mediated demyelination disorders, such as multiple sclerosis (MS), acute-disseminated encephalomyelitis, neuromyelitis optica spectrum disorder, Guillain-Barre syndrome, or sarcopenia may require repeated or sustained stimulation to counteract recurrent degeneration and maintain nerve function. In these cases, the device can remain implanted to deliver therapy as desired, providing flexibility for adaptive treatment schedules based on disease progression and patient response. Additionally, natural aging, ongoing nerve injuries, spinal cord injury or any other degrading or damaging mechanism to the myelin or nervous tissue over the time of the chronic implant stimulation can counteract the degradation.

Illustrative embodiments also contemplate use in conditions where nerve integrity is compromised by systemic or localized disease processes, including autoimmune disorders that attack myelin sheaths. Although current data primarily supports stimulation for traumatic or surgical nerve injury, it is anticipated that electrical stimulation may help preserve neuronal viability and promote remyelination during early stages of demyelinating diseases, provided the neurons remain intact. In such embodiments, stimulation may target larger nerve branches (e.g., the phrenic nerve for respiratory function) or multiple sites to address systemic involvement.

In some embodiments, higher amplitudes or additional pulse trains may be applied to attempt greater recruitment; however, such increases often yield diminishing therapeutic returns and can accelerate muscle fatigue. Excessive stimulation may also waste battery power, reducing device longevity and increasing recharge frequency. Overstimulation can exacerbate fatigue-related effects or even weaken targeted muscles over time, potentially worsening conditions such as urinary incontinence rather than improving them. Accordingly, stimulation parameters are selected to balance efficacy, comfort, and energy efficiency while minimizing adverse outcomes.

Selectivity is achieved primarily by mechanical targeting, e.g., a direct-contact electrode (e.g., a clip or cuff) coupled to a distal branch and insulated to confine current to the target fascicles. The parameter guardrails described herein are sufficient for the target effect but insufficient to activate off-target branches. Various embodiments support charge-balanced biphasic waveforms (e.g., 1:1 recovery ratio) and permit recovery ratio adjustments (e.g., 1:2 with half-amplitude/double-duration recovery) so long as charge balance is maintained, providing flexibility for safety and device implementation.

In additional embodiments, a close-proximity electrode array positioned near the target nerve may also be used to deliver stimulation with some degree of spatial selectivity. Although such arrays can approximate the effects of mechanical targeting, they may carry a greater risk of off-target activation or reduced selectivity due to the absence of direct nerve engagement. In these configurations, careful electrode selection, current steering, and parameter guardrails may be employed to minimize unintended activation and maintain therapeutic efficacy.

While direct-contact configurations maximize efficiency and minimize off-target activation, near-contact arrangements can still achieve effective nerve depolarization provided that sufficient current is delivered to reach the activation threshold for a majority of nerve fibers. The trade-off in such configurations involves balancing increased current requirements against potential off-target stimulation and tissue impedance, particularly in cases where intervening fat or connective tissue may attenuate the electric field. Nevertheless, once the applied stimulation achieves the necessary threshold to elicit action potentials within the target nerve, regenerative outcomes such as axonal repair and remyelination are expected to be comparable to those achieved with direct-contact electrodes. This flexibility allows the system to adapt to anatomical constraints while maintaining therapeutic efficacy.

FIG. 1F schematically shows an anatomical drawing of nerves that neuromodulation devices may couple to in accordance with illustrative embodiments. A nerve branches from the central nervous system (CNS) towards a muscle by first exiting the spinal cord through spinal roots. These roots converge to form peripheral nerves that traverse the body. As the nerve reaches the target muscle, it divides into smaller branches, ultimately connecting at neuromuscular junctions. This branching allows the nerve to transmit motor signals from the CNS, facilitating muscle contraction and controlling voluntary movements.

The anatomy of a nerve extending from the central nervous system (CNS) to a target muscle is a complex process that involves several distinct stages. Once outside the spinal column, the spinal nerves branch out and may combine with axons from other spinal nerves to form networks called plexuses (e.g., brachial plexus for the arms, lumbar plexus for the legs). From these plexuses, numerous peripheral nerves emerge, directed towards specific areas of the body.

As the peripheral nerves approach their target muscles (towards a distal end of the nerve), they branch into smaller motor nerves. These motor nerves carry the impulses necessary for muscle contraction. At the target muscle, the nerve fibers terminate in specialized structures called neuromuscular junctions. Here, the axon terminal of a motor neuron releases neurotransmitters (mainly acetylcholine) across a small gap, the synaptic cleft, which binds to receptors on the muscle fiber's membrane (sarcolemma).

What is not shown well in many anatomical drawings in the art are the various sub-branches towards the distal end of the nerve (i.e., near the neuromuscular junction). This is because the number of branches a nerve can have varies widely depending on the specific nerve and its function. Nerves can branch off into many smaller nerves as they extend from the central nervous system (CNS) to their target organs or tissues. It is difficult to illustrate all of the anatomical nerve structures when including sub-branches, which have largely been ignored by the prior art as a source of treatment.

Advantageously, various embodiments couple one or more neuromodulation devices to the small distal nerve branches that innervate the target muscles discussed herein. However, illustrative embodiments may additionally or alternatively couple one or more neuromodulation devices anywhere along a given nerve (e.g., not just at or near the distal nerve branch).

When a large nerve branches, each branch may carry a different number of fascicles. For instance, when the sciatic nerve divides into the common peroneal and tibial nerves, each branch carries a subset of the fascicles from the main nerve. The division isn't necessarily equal, and the number of fascicles in each branch depends on the specific functions and size of the area each branch innervates. As these branches subdivide further to innervate specific muscles or skin areas, the number of fascicles in each smaller branch continues to decrease. Various embodiments couple one or more neuromodulation devices to a distal nerve branch that innervates a pelvic floor muscle, where the distal nerve branch has as few as 1-3 fascicles. In some embodiments, the distal nerve branch may be a terminal nerve branch. However, as mentioned above, illustrative embodiments may couple one or more neuromodulation devices to a larger portion of the nerve.

In addition to, or alternatively to, identifying distal nerve branches by their fascicle count, it is also possible to define the distal nerve branches by their location along the nerve. A nerve originates at a soma and has an axon extending from the soma to an axon terminal. The distal nerve branch that innervates a pelvic floor muscle may be at the last ⅓ or last ¼ of the length of the nerve (e.g., near the distal end closest to the muscle.). Various embodiments couple one or more neuromodulation devices to a distal nerve branch at a point that is along the last ⅓rd or ¼th of the length of the nerve.

Distal nerve branches are generally not shown in anatomical drawings due to the large number, and do not have well defined anatomical names. In the past, the inventors have referred to the distal nerve branches by the anatomical name of the major nerve from which they branch. However, to provide further clarity, illustrative embodiments may refer to the distal nerve branch by the name of the nerve from which it branches and also the muscle which it innervates. However, it is understood that one or more particular distal nerve branches from a larger nerve may innervate a particular muscle. Furthermore, various embodiments stimulate with nerves approaching from the right and left sides of the body such that stimulation of a nerve and its contralateral nerve may achieve a desired clinical effect. In various embodiments, one or more of the identified distal nerve branches may be stimulated. The distal nerve branches (including terminal branches) are shown.

It should be understood that any anatomical drawings, schematics, or depictions of neural structures provided herein are presented solely for purposes of illustration. Although certain figures show pelvic nerves, distal branches, and terminal portions that innervate target musculature, such drawings are not necessarily to scale, and the relative positioning, branching patterns, diameters, and lengths of individual nerves may vary among human subjects. At very distal termini, anatomical variation is common, and the number, trajectory, and precise location of branches can differ between individuals.

Various embodiments described herein are intended to be representative of only one possible anatomical configuration. Similar nerve distributions are generally present across patients. However, no limitation should be inferred from the particular form, proportions, or arrangement of the nerve structures depicted in the figures. The methods, systems, and devices disclosed herein are configured to operate effectively across a wide range of anatomical presentations, including variations in nerve position, branching pattern, orientation, or topology. Accordingly, the scope of various embodiments is not restricted to the specific anatomical examples shown, but encompasses all physiologically relevant variations consistent with the claims.

Figure 1D:
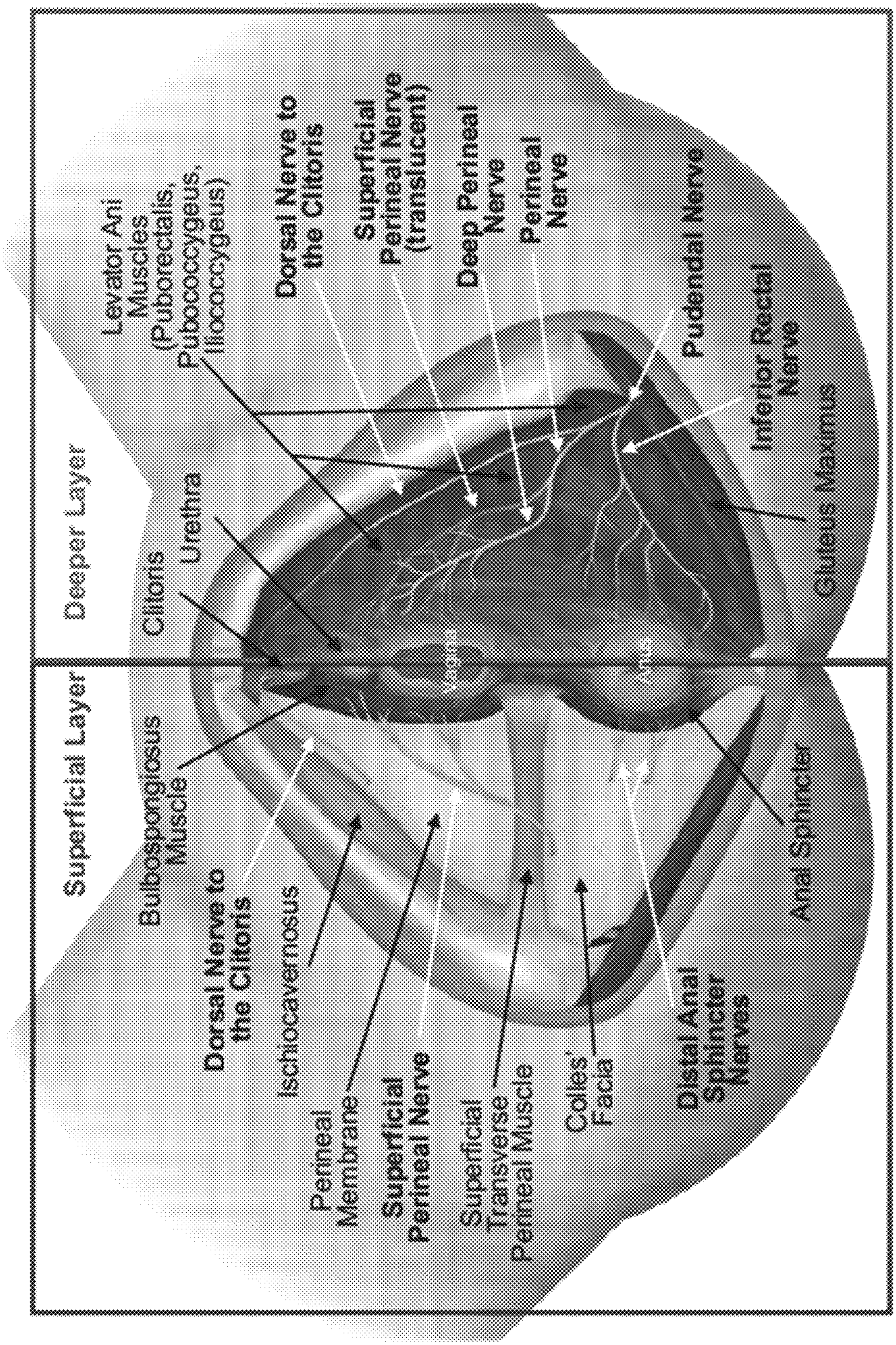
FIG. 1D illustrates an example of the neuroanatomy of the pelvic floor from a caudal view, divided into two layers for clarity in accordance with illustrative embodiments.
Figure 1E:
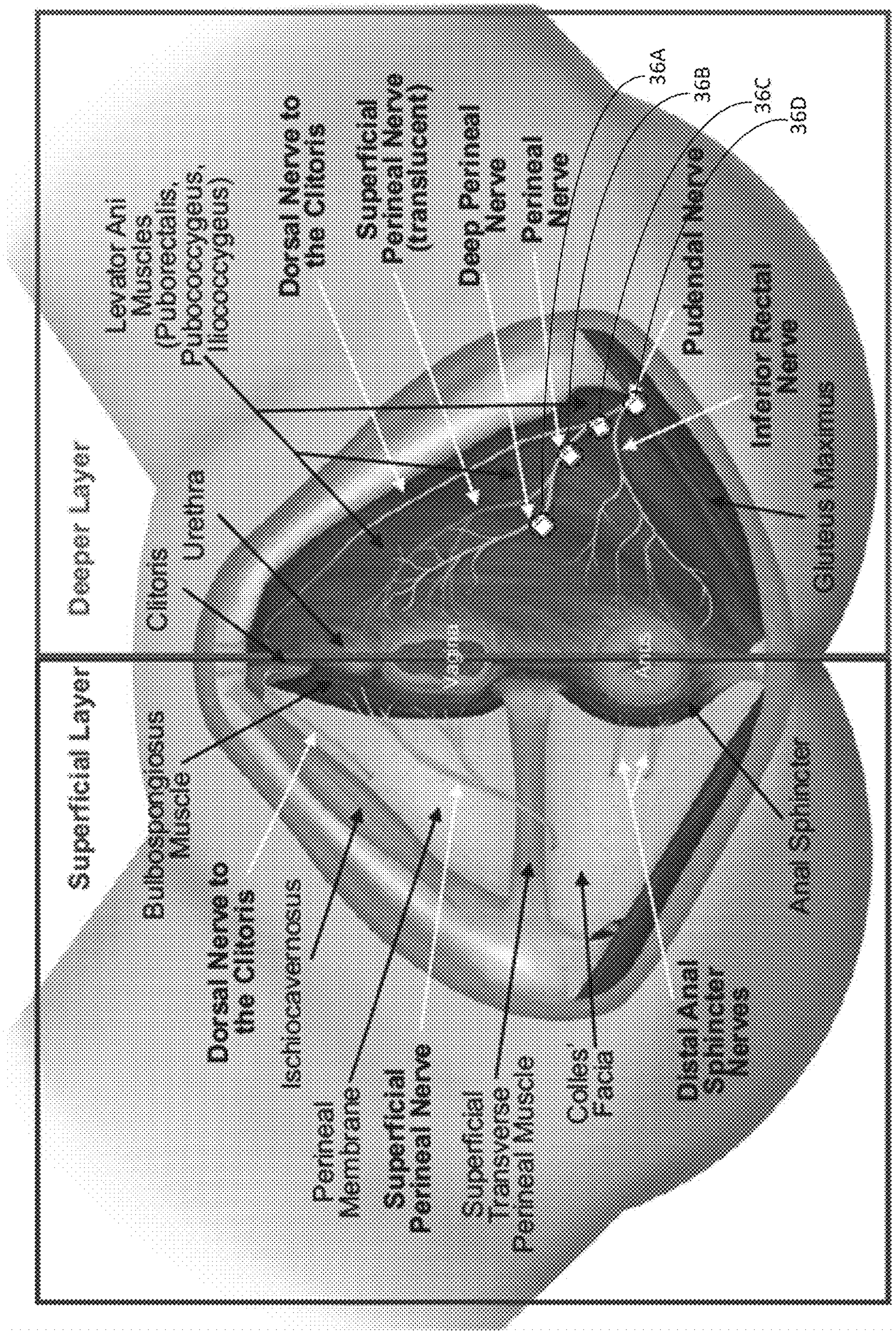
FIG. 1E schematically shows candidate direct-contact electrode placements along branches of the pudendal and perineal nerve complex in a caudal view of the pelvic floor shown in FIG. 1D in accordance with illustrative embodiments.

FIG. 1E schematically shows candidate direct-contact electrode placements along branches of the pudendal and perineal nerve complex in a caudal view of the pelvic floor shown in FIG. 1D. The figure highlights preferred distal positions (first position and second position) and less-desirable proximal positions (third position and fourth position), based on functional selectivity and off-target activation risk. In this example, the desired target is the pubococcygeus muscle, and variations of muscle fibers of the levator ani.

Selective stimulation refers to the activation of a single physiological target or a portion of that target, where a physiological target is defined as a single anatomically recognized muscle or a sub-portion of that muscle's myofibers, a single sensory dermatome or a sub-region of that dermatome, or a single autonomic organ or a defined subportion of that organ. Activation may involve the entire target or a physiologically meaningful subset, such as a defined group of myofibers within one muscle, but selective stimulation does not extend beyond that individual anatomical structure. In short, selective stimulation corresponds to activation of one physiological target, whether a muscle, dermatome, or organ, or a portion thereof.

Semi-selective stimulation refers to activation of more than one but not more than three physiological targets within a related anatomical region. Semi-selective stimulation therefore encompasses activation of two or three muscles that share regional function, such as pelvic floor muscles; two or three dermatomes within a related sensory territory, such as S2 through S4; or two or three organs. This category reflects that certain therapeutic goals may require activation of closely adjacent or functionally linked structures, and that some distal nerve branches naturally innervate small clusters of targets. In short, semi-selective stimulation corresponds to activation of two to three physiological targets. In various embodiments, semi-selective stimulation does not include negative off-target effects. Thus, when the intended objective is modulation of urinary outlet structures, semi-selective stimulation expressly excludes inadvertent activation of sensory branches such as the dorsal nerve of the clitoris.

Non-selective stimulation, by contrast, refers to activation of more than three physiological targets. Examples include broad activation of numerous pelvic floor muscles; sensory activation across wide dermatomal regions; or stimulation of multiple organs downstream of a large mixed-fascicle nerve trunk, such as the pudendal or vagal trunk. Non-selective stimulation typically arises from stimulation delivered at higher-order or proximal nerves that distribute to many downstream structures and represents the least targeted form of neuromodulation. In short, non-selective stimulation involves four or more physiological targets.

These definitions are illustrated by several examples. With respect to muscle targeting, stimulation of the deep perineal nerve at Position 1 activates only the pubococcygeus muscle and is therefore selective. Stimulation at Position 2 activates the pubococcygeus and the bulbospongiosus muscles (two muscles) and is therefore semi-selective.

Stimulation at the pudendal trunk activates more than ten muscles, including the levator ani, external urethral sphincter, bulbospongiosus, external anal sphincter, inferior rectal muscles, and others, and is therefore non-selective. These examples demonstrate the one-target, two-to-three-target, and greater-than-three-target framework described above. In the sensory domain, because peripheral sensory nerves map to dermatomes, selectivity is defined by the specific area of skin affected. Activation of a single sacral dermatome, such as S3, or a sub-region of that dermatome is selective; activation of dermatomes S2 through S4 is semi-selective; and activation of widespread thoracic or sacral dermatomal territories is non-selective. This approach aligns with standard neuroanatomical mapping. In the autonomic domain, although autonomic nerves often branch into plexuses, distal branches still correspond to specific organs or organ subunits. For example, stimulation of a renal nerve branch that modulates only the left kidney is selective; stimulation of a branch that modulates both the kidney and ureter is semi-selective; and stimulation of the vagus nerve or proximal pelvic plexus, which influences multiple abdominal organs, is non-selective. These examples maintain objective anatomical boundaries and illustrate the application of the selectivity definitions across muscular, sensory, and autonomic systems.

In certain embodiments, selectivity may be described with greater specificity according to the type of physiological target being activated. For muscular targets, the stimulation may be referred to as myoselective, meaning that the stimulation is confined to a single muscle or a physiologically meaningful portion of that muscle's myofibers, consistent with the definition of selective stimulation described herein. For sensory targets, the stimulation may be described as dermatoselective, meaning that stimulation is limited to a single dermatome or a sub-region of that dermatome, without extending into additional sensory territories. For autonomic or visceral targets, the stimulation may be described as visceroselective, meaning that stimulation is directed to a single autonomic organ or a defined sub-portion of that organ, such as one kidney or a specific gastrointestinal segment, without activation of additional organ systems. These modality-specific terms provide a clear and anatomically grounded means of distinguishing between muscular, sensory, and autonomic embodiments of selective neuromodulation, while remaining fully aligned with the numerical selectivity framework described above for selective, semi-selective, and non-selective stimulation.

The parameters in Table 1 apply to selective stimulation. However, stimulation amplitude is maintained within a range of about 0.1-3 mA for selective therapy using direct-contact electrodes, and may be scaled according to nerve size and threshold feedback. Broader ranges (e.g., up to 5 mA) may be employed for semi-selective configurations or larger nerves, while amplitudes above 5 mA are generally unnecessary for the selective embodiments described herein.

FIG. 1E illustrates four exemplary positions for nerve stimulation devices according to illustrative embodiments, demonstrating selective, semi-selective, and non-selective stimulation configurations.

Position 1 36A (deep perineal nerve) represents a selective stimulation site, as direct contact at this distal branch enables activation of the pubococcygeus and variations of the levator ani muscles without extending beyond this anatomical target. When stimulation is titrated to threshold, off-target activation is not anticipated. This position 36A is preferred for highly targeted therapy because it delivers charge directly to fascicles responsible for the desired functional response, achieving depolarization at lower, safer amplitudes and reducing current spread to adjacent nerves. These distal placements are advantageous because they achieve the desired effect at lower amplitudes, reducing the risk of exceeding electrode safety limits.

Position 2 36B (a more superficial perineal branch) is generally semi-selective, as stimulation may activate the pubococcygeus while also recruiting the bulbospongiosus muscle or other perineal musculature. Although these structures share regional function, they represent distinct physiological targets under the selectivity framework. Activation remains clinically acceptable when amplitudes are maintained within safe limits, but this position 36B is less desirable for strict selective engagement because it introduces additional muscle activation beyond the primary target. While not considered deleterious, this position 36B is less selective than Position 1 36A.

Position 3 36C (a distal pudendal branch leading toward the perineal nerve) is non-selective, as stimulation near this branching site often recruits multiple fascicular pathways, including those to the dorsal nerve of the clitoris, bulbospongiosus, and other pelvic floor muscles. While this position 36C excludes the inferior rectal nerve and therefore avoids anal sphincter contraction, it still engages more than three distinct targets, placing it outside the selective or semi-selective categories. This position 36C may require higher stimulation amplitudes to achieve the desired distal effect (e.g., at the pubococcygeus), which can increase the risk of exceeding electrode safety limits. Accordingly, while effective for certain therapeutic goals, this position is not selective or semi-selective.

Position 4 36D (proximal pudendal trunk or early branches) is also non-selective, as stimulation at this level typically activates a broad set of targets, including the levator ani group, external urethral sphincter, bulbospongiosus, dorsal nerve to the clitoris, and the inferior rectal nerve, resulting in anal sphincter contraction. These proximal placements 36C and 36D require higher stimulation amplitudes and pose greater risk of off-target effects. Without intending to be bound by theory, the inventors believe that distal placements 36A and 36B improve selectivity because fascicular architecture becomes simpler toward the distal target (e.g., (fewer, more target-specific fascicles). Delivering cathodic charge directly to the distal fascicle maximizes the proportion of channels affected within that fascicle, improving the likelihood of threshold depolarization of the intended nerve while reducing current spread. By contrast, more proximal stimulation (e.g., 36C and 36D) interacts with more numerous and heterogeneous fascicles, so a given field is more likely to recruit multiple pathways, thereby diluting the effect on the intended branch and increasing off-target co-activation. Although action potentials are all-or-none at the axon level, the number of recruited axons varies with placement and field geometry; damaged nerves may also exhibit elevated thresholds, favoring placements that deliver a higher fraction of the field to the intended fascicle at safe amplitudes.

The therapy of various embodiments yields at least two coordinated benefits: (i) initiation of axonal regeneration, which can occur with at least one appropriately delivered session, and (ii) promotion of remyelination repair and more rapid/larger functional recovery through multiple sessions over time. The therapy is applicable across peripheral nerve types and sizes, with illustrative embodiments for pelvic nerves (e.g., perineal and inferior rectal nerves) as well as limb and autonomic nerves (e.g., vagus, cardiac, renal, cavernous).

Illustrative embodiments provide a number of advantages over prior art approaches. Prolonged continuous intraoperative stimulation (e.g., ~1 hour at low frequency) has been reported to accelerate regeneration, but it is clinically impractical (adds significant operating time), is energy-intensive, and does not address selectivity at distal branches. In addition, such continuous paradigms are not designed for, nor do they teach, a clinically workable chronic regimen that coordinates regeneration with remyelination and functional training longitudinally (e.g., over weeks).

Illustrative embodiments provide several advantages compared to prior art nerve stimulators. First, the clip style device of various embodiments offers a large circumferential contact surface area, enabling uniform engagement with the nerve along a substantial portion of its circumference. In various embodiments, each electrode may have a length ranging from approximately 4 mm to 7 mm and a width ranging from 0.25 mm to 0.6 mm, resulting in a contact surface area of about 1 $mm^2$ to 4 $mm^2$, around 3.25 $mm^2$ (e.g., 6.5 mm×0.5 mm). This surface area supports safe charge density limits, reduces impedance, and improves charge injection capacity for chronic stimulation. Preferentially, the electrodes are arranged in a circumferential configuration that surrounds the nerve to maximize contact and uniform current distribution. In some embodiments, the engagement structure provides coverage of more than 50% of the nerve circumference, and more than 80%, to enhance selectivity and stimulation efficiency while minimizing off-target activation. This contrasts with prior art devices that rely on small point contacts or needle electrodes, which concentrate current delivery into a limited region, resulting in high charge density and increased risk of tissue damage. By distributing current across a broader area, illustrative embodiments achieve lower impedance, improved safety margins, and more efficient stimulation at lower amplitudes.

Second, the disclosed system supports variable stimulation parameters, including adjustable frequency, amplitude, and pulse train architecture. This flexibility allows therapy to be tailored to nerve type (motor, sensory, autonomic) and therapeutic goals, whereas prior art devices often operate at fixed frequencies and lack the ability to deliver structured train-and-rest cycles. Such adaptability advantageously promotes nerve regeneration and remyelination, as different nerve types exhibit distinct physiological responses to stimulation frequency.

Third, illustrative embodiments are configured for chronic therapy, enabling repeated or sustained stimulation sessions over weeks or months to accelerate recovery and maintain functional gains. In contrast, prior art systems are primarily intended for intraoperative use, providing only brief stimulation during surgical procedures. Evidence indicates that multiple stimulation sessions produce superior regenerative outcomes compared to single intraoperative applications (e.g., see FIG. 5).

Additionally, transcutaneous or broad "volume conduction" systems (e.g., pelvic floor "pants" or generalized surface electrodes) lack targeting precision, often produce off-target activation, and deliver inconsistent fields across patients. They do not ensure direct coupling to the intended nerve branch, making dose and effect unreliable, and they can provoke discomfort without providing the organized, selective neural activity that supports axonal regrowth and remyelination at the site of need. In addition, lead migration or displacement of surface-contact elements can further alter the delivered field, degrade selectivity, and contribute to variable or diminished therapeutic outcomes.

Generic nerve cuff literature demonstrates direct contact at proximal nerve sites, but additionally do not disclose the specific parameter architecture, short above-threshold pulse trains, rest intervals, nerve-type thresholds, and multi-week regimens of various embodiments to (a) initiate axonal regeneration efficiently and (b) promote remyelination repair with reduced fatigue and lower energy burden. Prior disclosures frequently lack clear threshold definitions tied to nerve type (motor/sensory/autonomic), fail to normalize for nerve size, and do not articulate objective, indication-specific outcomes (e.g., urethral closure pressure, fecal episode counts) as functional endpoints.

By contrast, illustrative embodiments (1) target the correct branch (e.g., distal branch) with direct-contact, insulated electrodes to achieve selectivity; (2) use a short-train/defined-rest architecture to minimize fatigue, reduce energy consumption, and improve tolerability; (3) bind amplitude to threshold appropriate for the nerve type, with bounded ranges that scale to nerve size; and/or (4) specify clinically meaningful, objective outcomes. These features produce a practical, selective, and biologically grounded therapy that initiates and advances axonal regeneration, promotes remyelination repair, and delivers faster and larger functional improvements than prior art approaches while remaining feasible for real-world clinical deployment.

In various embodiments, stimulation amplitude is scaled to nerve size to maintain effective depolarization while minimizing charge density and energy consumption. For example, nerves as small as 0.5 mm may be stimulated at amplitudes near 0.1 mA, whereas larger nerves up to 25 mm may require amplitudes approaching 3 mA. This proportional scaling reflects the relationship between nerve diameter, axon count, and tissue impedance. While the system may support a broad amplitude range (e.g., 0.1-5 mA), clinical use embodiments fall within 0.1-3 mA for direct-contact configurations. Amplitude selection may be guided by threshold-based titration following implantation to account for variations in tissue environment and encapsulation.

Thus, prior art nerve stimulation typically delivers stimulation in short bursts during intraoperative procedures or event-driven applications (e.g., respiratory-triggered stimulation for sleep apnea). Illustrative embodiments are configured for chronic therapeutic use aimed at functional nerve repair and restoration. In various embodiments, stimulation is delivered in structured sessions comprising pulse trains of less than eight bursts per session, with each train lasting 3-60 seconds, and total session durations maintained well below one hour to minimize fatigue and optimize recovery. While additional pulse trains could theoretically be applied, such increases generally yield diminishing returns, accelerate muscle fatigue, and unnecessarily deplete battery capacity, potentially compromising long-term therapy. Excessive stimulation may even weaken targeted muscles over time, exacerbating conditions such as urinary incontinence rather than improving them. Accordingly, the disclosed system balances efficacy, safety, and energy efficiency by limiting cumulative stimulation time while maintaining amplitudes within comfort and safety limits (e.g., ≥0.1 mA for small distal nerves and ≤~2 mA for pelvic applications). This chronic, parameter-optimized approach contrasts with prior art devices that either apply brief intraoperative stimulation or event-driven bursts without therapeutic intent for nerve regeneration.

One of the challenges in electrical stimulation therapies is the onset of muscle and nerve fatigue when stimulation is delivered continuously or at high intensity for extended periods. Fatigue can lead to diminished therapeutic effect, patient discomfort, and even adverse outcomes such as leakage during pelvic floor therapy. Prior art approaches, including continuous intraoperative stimulation for up to an hour, exacerbate this problem by maintaining constant activation of motor units without recovery intervals, resulting in rapid depletion of neuromuscular resources and reduced efficacy over time.

Illustrative embodiments advantageously overcome these limitations through a pulse-train protocol with defined rest intervals. Instead of continuous stimulation, the therapy employs short trains of pulses (e.g., 5-30 seconds) followed by rest periods (e.g., 1-5 minutes). This design allows motor units and nerve fibers to recover between trains, minimizing fatigue while maintaining the regenerative signaling required for axonal growth and Schwann cell recruitment. By spacing trains within a session and limiting total stimulation time, illustrative embodiments preserve neuromuscular responsiveness and improves patient tolerability.

Additionally, illustrative embodiments use threshold-based stimulation rather than excessive amplitudes. For motor nerves, stimulation is delivered at or slightly above contraction threshold, ensuring activation without unnecessary overload. For sensory and autonomic nerves, stimulation is tied to sensation or physiological thresholds, avoiding overstimulation that could lead to discomfort or autonomic imbalance. This targeted approach reduces cumulative stress on the nerve and surrounding tissue while still achieving the biological triggers for regeneration and remyelination.

The combination of short, above-threshold trains, rest intervals, and bounded amplitude ranges provides a novel solution to fatigue management. It enables chronic therapy over weeks without diminishing returns, unlike prior art methods that either rely on impractical continuous stimulation or fail to address fatigue altogether. By reducing fatigue, illustrative embodiments not only improve safety and comfort but also enhances long-term outcomes, allowing patients to complete multi-week regimens that accelerate nerve repair and restore functional performance.

Illustrative embodiments deliver electrical stimulation to peripheral nerves using charge-balanced biphasic pulse trains. Each pulse may consist of a stimulation phase followed by an inverse recovery phase, ensuring net zero charge transfer to minimize tissue damage and electrode corrosion. In various embodiments, the recovery ratio may be between 1:1 (equal amplitude and duration for stimulation and recovery phases) or 1:2 (e.g., where the recovery phase has half the amplitude and double the duration).

While monophasic or other pulse shapes may elicit a physiological response, biphasic stimulation is preferred because it mitigates the risk of nerve injury by preventing net charge buildup at the electrode-tissue interface. A biphasic pulse provides charge balancing that reduces electrode polarization, limits undesirable electrochemical reactions, and helps maintain a stable current distribution within the nerve. By contrast, monophasic stimulation may accumulate charge and alter local polarity in a manner that increases the likelihood of tissue irritation or damage. Accordingly, various embodiments advantageously employ biphasic pulses to promote safe, repeatable stimulation suitable for applications involving nerve repair or long-term therapeutic use. However, while biphasic pulses provide advantages, some embodiments may operate with one or more phases (e.g., monophasic, triphasic, etc.).

Waveform shapes may include square, triangular, sawtooth, or sinusoidal profiles, and pulse trains may incorporate ramping envelopes, gradual amplitude increases at the start of a train, to reduce abrupt onset sensations. These waveform options provide clinicians with tools to tailor therapy for tolerability and physiological response.

To avoid muscle and nerve fatigue while promoting regeneration and remyelination, some embodiments employ a progressive regimen. Rather than continuous stimulation, therapy may be delivered in short bursts (pulse trains) separated by rest intervals, allowing neuromuscular recovery between activations. This reduces cumulative stress on motor units, and improves patient comfort.

The regimen can be scaled over time to match patient tolerance and therapeutic goals. For example, early sessions may use fewer trains or shorter durations, gradually increasing stimulation time or train count as the patient adapts. This progression supports sustained biological signaling for axonal regrowth and Schwann cell activity while minimizing fatigue.

Selectivity

As discussed above, selectivity enables the stimulation system and method to activate a target nerve or nerve branch while minimizing or avoiding activation of adjacent or off-target nerves and tissues. Selectivity is achieved primarily through mechanical targeting in combination with precision target site delivery (e.g., a direct-contact electrode clip or cuff) is positioned on a distal branch of the intended nerve and insulated to confine current to the target fascicles. This physical configuration ensures that the electrical field is localized and does not propagate broadly through surrounding tissue.

Selectivity is further reinforced by parameter guardrails, including amplitude, frequency, and pulse width settings that are sufficient to elicit the desired physiological response in the target nerve (e.g., contraction threshold for motor nerves, sensation threshold for sensory nerves, physiological threshold for autonomic nerves) but insufficient to activate neighboring nerves at therapeutic levels. Evidence of selectivity may include the absence of specified off-target responses (e.g., no inferior rectal reflex when stimulating the perineal nerve) and confirmation of functional outcomes associated with the intended nerve pathway.

By combining anatomical precision with threshold-based parameterization, illustrative embodiments provide a reproducible and clinically meaningful approach to selective nerve stimulation. This is advantageous over prior art methods, such as transcutaneous or volume conduction techniques, which lack targeting precision and often produce inconsistent or off-target activation.

Selectivity Example 1: Selective Stimulation for Perineal Nerve Regeneration and Remyelination for Continence In some embodiments, a direct-contact electrode (e.g., a clip or cuff) is mechanically coupled to a distal branch of the perineal nerve that innervates urethral closure musculature within the levator ani complex. The electrode's stimulation surfaces are positioned in direct contact with the nerve, while the remaining exterior surfaces of the electrode housing are insulated to confine current to the targeted fascicles and limit volume conduction to adjacent branches. This mechanical selectivity is reinforced by parameter guardrails chosen to activate the perineal branch while avoiding nearby nerves. Specifically, stimulation from the parameters disclosed in Table 1 is delivered at or slightly above the contraction threshold of the perineal target, with a frequency of about 20-100 Hz (e.g., 40-80 Hz), pulse width of about 100-500 μs (e.g., ~250 μs), pulse trains of about 3-60 seconds, followed by rest intervals of about 1-5 minutes, repeated for 1-8 trains per session, ≥1 session/day, 3-7 days/week, over ≥2-20 weeks.

By confining stimulation to the distal branch of the perineal nerve to selectively activate motor fibers responsible for urethral closure and operate at or slightly above the contraction threshold, illustrative embodiments ensure localized depolarization of axons, triggering pro-regenerative gene expression and Schwann cell recruitment. This selective activation promotes axonal regrowth across damaged segments and supports remyelination repair, restoring conduction and improving continence. Off-target avoidance (e.g., no inferior rectal nerve activation) prevents unnecessary stimulation of unrelated pathways, reducing fatigue and discomfort while focusing regenerative signaling where desired.

On-target confirmation for includes an observed or palpable urethral closure response at threshold and/or optional EMG evidence of motor unit recruitment in the urethral sphincter/levator ani at threshold or slightly above. Off-target absence is assessed by verifying no "anal wink" or external anal sphincter activation at the perineal thresholds (indicating the inferior rectal nerve has not been driven) and no diffuse pelvic contraction suggestive of pudendal trunk activation. Objective outcomes can include increased urethral closure pressure, improved leak point pressure, reduced stress leak frequency, and improved voiding efficiency/capacity measured over a multi-week regimen. The short-train/defined-rest architecture manages comfort and minimizes fatigue while sustaining regenerative and remyelination signaling.

Selectivity Example 2: Selective Stimulation for Inferior Rectal Nerve Repair for Fecal Control In another embodiment, the inferior rectal nerve supplying the external anal sphincter is targeted using a direct-contact electrode configured to couple with the inferior rectal branch with insulation to shield neighboring perineal branches and the more proximal pudendal trunk. Selectivity is achieved by this distal placement together with parameter guardrails that are sufficient for on-target activation but insufficient to drive adjacent branches at therapeutic amplitudes. Stimulation may be delivered at or slightly above the contraction threshold for the external anal sphincter, using a frequency of about 20-100 Hz (e.g., 40-80 Hz), pulse width of about 100-500 μs, pulse trains of 3-60 seconds, and rest intervals of 1-5 minutes, with 1-8 trains/session, ≥1 session/day, 3-7 days/week, for ≥2-20 weeks.

The inferior rectal nerve is targeted to restore external anal sphincter function. Selective stimulation at contraction threshold initiates axonal regeneration in partially injured fibers and enhances Schwann cell activity for remyelination. By avoiding activation of perineal branches, the therapy concentrates repair processes on the anal sphincter pathway, improving fecal continence without inducing unwanted pelvic contractions. Objective outcomes such as increased anal squeeze pressure and reduced incontinence episodes confirm functional recovery driven by nerve repair.

On-target confirmation includes an observed sphincter contraction at threshold and/or optional EMG in the external anal sphincter. Off-target absence is verified by no urethral closure pressure rise at the inferior-rectal therapeutic amplitudes (indicating perineal motor branches are not activated) and no diffuse pelvic recruitment (indicating the pudendal trunk is not driven). Objective outcomes include increased anal squeeze pressure and a reduction in fecal incontinence episodes over the course of therapy. The short-train/defined-rest regimen reduces fatigue risk and supports progressive neuromuscular recovery.

Selectivity Example 3: Selective Stimulation of Levator Ani Motor Branches for Pelvic Support In a further embodiment, a small-diameter levator ani motor branch is selectively targeted with a direct-contact clip; a conformal insulating body is used to minimize current spread to inferior rectal and perineal branches. Parameter-based selectivity is obtained by operating at or slightly above the contraction threshold of the levator ani target using pulse-train delivery (about 20-100 Hz frequency; 100-500 μs pulse width; 3-60 second trains; 1-5 minute rests; 1-8 trains per session; with daily or near-daily sessions over ≥2-20 weeks).

Selective stimulation to the levator ani motor branches may reverse conduction deficits caused, for example, by childbirth-related stretch injuries. Direct-contact placement and threshold-based titration ensure targeted activation of damaged axons, initiating regeneration and remyelination while minimizing off-target effects. Over a multi-week regimen, progressive adjustments maintain stimulation within safe ranges as thresholds may decline with recovery. Functional improvements in urethral closure and pelvic support validate the repair process.

On-target confirmation is demonstrated by visible/palpable levator ani contraction at threshold and/or optional EMG localized to levator ani. Off-target absence is confirmed by no anal sphincter contraction (sparing the inferior rectal branch) and no cutaneous paresthesia in the perineal field at therapeutic amplitudes (sparing perineal sensory branches). Functional outcomes include improved urethral closure capability, reduced stress leak frequency over time, and measurable improvements in pelvic organ prolapse (POP) scores or other validated pelvic floor function indices. The disclosed train-and-rest architecture, combined with threshold-based titration, sustains on-target nerve engagement while mitigating fatigue and preserving tolerability. This structured approach enables chronic therapy that promotes nerve repair and functional recovery without the drawbacks of continuous stimulation paradigms.

Selectivity Example 4: Selective Stimulation of the Renal Nerve (Autonomic) Using Physiological Thresholds In accordance with another embodiment, selective stimulation is applied to a renal nerve branch to promote reinnervation of the kidney following surgical denervation, such as after kidney transplantation. The renal nerve provides sympathetic innervation that regulates blood pressure and water-salt homeostasis. Direct-contact placement of the stimulation device on an isolated renal branch enables visceroselective activation of the kidney without engaging adjacent autonomic structures.

On-target confirmation is established by observing a controlled physiological response indicative of renal activation, such as changes in renal blood flow, urine output, or biomarkers of sympathetic tone. Stimulation parameters may include biphasic pulses delivered in short pulse trains of about 3-60 seconds at a frequency of 20-100 Hz and a pulse width of 100-400 μs, separated by rest intervals of 0.5-5 minutes, with fewer than eight bursts per session and a total session duration of less than one hour. Amplitude is titrated to the minimal threshold required to achieve the desired renal response, typically within 0.1-3 mA for selective therapy. Off-target avoidance is achieved by positioning the device distal to the aortico-renal and celiac plexus to prevent activation of adjacent branches that innervate the adrenal gland, gonads, or ureter. Stimulation at these proximal sites would be considered non-selective, as it could trigger systemic sympathetic effects such as increased heart rate, elevated blood pressure, and altered vascular tone. By confining stimulation to the renal branch and titrating to physiological thresholds, the disclosed method achieves selective activation of a single autonomic organ while minimizing systemic side effects.

Sensation/Perception Threshold

As used herein, the term sensation or perception threshold refers to the minimum stimulation intensity at which a patient becomes aware of the stimulation, typically through a perceived muscle contraction or tingling sensation. This threshold is distinct from the contraction threshold, which is defined by visible or palpable muscle movement, and from the pain threshold, which represents the onset of discomfort. Sensation threshold is generally higher than the action potential threshold of the nerve but lower than the pain threshold, making it a clinically useful reference point for titrating stimulation.

The sensation threshold is relevant for sensory nerve repair and for patient comfort during chronic stimulation. In embodiments where sensory modulation is desired, such as treatment for overactive bladder (OAB) or urgency symptoms, stimulation is delivered below or near the sensation threshold to avoid discomfort while still activating sensory fibers that influence reflex pathways. Operating at or slightly below this threshold ensures that the therapy remains tolerable for the patient while achieving neuromodulatory effects without triggering unwanted motor contractions.

In practice, the sensation threshold is determined qualitatively during setup by gradually increasing stimulation amplitude until the patient reports a perceptible contraction or tingling. Device algorithms or clinician protocols may then set the operating amplitude at a fixed percentage below this threshold (e.g., approximately 10%) for afferent therapy, or above this threshold for certain motor or mixed nerve applications where contraction is beneficial. This approach provides a reproducible and patient-specific reference point that balances efficacy with comfort, supporting long-term adherence to therapy regimens.

Contraction Threshold

As used herein, contraction threshold refers to the minimum stimulation intensity required to produce a visible or palpable contraction of the muscle innervated by the target motor nerve. This threshold is a practical and clinically relevant reference point for motor nerve stimulation because it provides an observable indicator that the stimulation has successfully activated motor units and generated action potentials in the nerve fibers.

The contraction threshold is distinct from other thresholds such as sensation threshold or pain threshold. While sensation threshold depends on patient perception and can vary widely, contraction threshold offers an objective measure that can be confirmed visually or through palpation, and/or optionally verified using electromyography (EMG). In sedated or anesthetized patients, where subjective feedback is unavailable, contraction threshold becomes a primary method for determining adequate stimulation.

Illustrative embodiments use the contraction threshold as the basis for setting stimulation amplitude for regeneration and remyelination. Delivering stimulation at or slightly above contraction threshold ensures that the nerve receives sufficient electrical input to trigger action potentials and initiate pro-regenerative signaling without applying unnecessary or excessive current that could cause discomfort or fatigue. This approach balances efficacy with safety and supports selective activation of the target nerve while minimizing off-target effects. By anchoring stimulation parameters to contraction threshold, illustrative embodiments provide a reproducible and clinically meaningful standard for therapy delivery. This threshold-based approach enables consistent outcomes across patients and nerve types, supports progressive regimens for comfort, and distinguishes illustrative embodiments from prior art methods that rely on fixed amplitudes or continuous stimulation without regard to nerve-specific activation levels.

Pain Threshold

As used herein, pain threshold refers to the stimulation intensity at which a patient first experiences discomfort or pain during electrical stimulation. This threshold is higher than both the sensation threshold and the contraction threshold, and it represents an upper limit for therapy delivery. While illustrative embodiments do not aim to operate at or near the pain threshold, understanding its position in the hierarchy of thresholds is critical for ensuring patient comfort and preventing adverse effects.

The pain threshold is clinically important because it provides a clear boundary for amplitude adjustments during chronic therapy. In various embodiments where stimulation is delivered repeatedly over weeks, maintaining amplitudes well below the pain threshold minimizes the risk of discomfort, tissue irritation, or therapy discontinuation. This is particularly relevant for chronic applications, where patient adherence depends on tolerability.

Illustrative embodiments leverage this concept by defining stimulation parameters relative to lower thresholds, such as contraction threshold for motor nerves and sensation threshold for sensory nerves, while explicitly avoiding amplitudes that approach the pain threshold. This approach distinguishes illustrative embodiments from prior art methods that often rely on fixed amplitude settings without individualized threshold calibration, which can lead to unnecessary discomfort or inconsistent outcomes. By incorporating threshold-based titration and progressive regimens, illustrative embodiments ensure effective nerve activation for regeneration and remyelination while preserving patient safety and comfort.

EMG Threshold

The EMG threshold refers to the stimulation intensity at which an electromyographic signal is first detected in the target muscle. This threshold typically occurs below the contraction threshold and provides an objective measure of nerve activation when visible or palpable contraction is absent.

The EMG threshold is particularly valuable in situations where the patient is sedated or anesthetized, or when the muscle is too weak to produce a visible contraction. The EMG threshold could also be used when the patient is particularly sensitive to stimulation. By monitoring EMG activity, clinicians can confirm that stimulation is sufficient to depolarize motor units and trigger action potentials, ensuring therapy efficacy even in severe injury cases. Illustrative embodiments may incorporate EMG-based detection as an optional method for threshold determination, supporting consistent therapy delivery across diverse clinical contexts.

Physiological Threshold

The physiological threshold refers to the stimulation intensity required to elicit a measurable functional response in an autonomic nerve pathway, such as a change in heart rate, blood pressure, respiration rate or organ-specific activity.

For illustrative embodiments stimulating autonomic nerves, contraction or sensation thresholds are not applicable. Instead, physiological markers provide a practical reference for titrating stimulation. For example, vagus nerve stimulation may use heart rate modulation as a threshold indicator. This approach ensures selective activation of autonomic fibers without overstimulation, enabling safe and effective therapy for organ function regulation and autonomic disorders.

Action Potential Thresholds (Nerve and Muscle)

The action potential threshold for a nerve is the minimum membrane potential required to initiate an action potential in neuronal axons. For muscle fibers, it is the minimum stimulation level to trigger contraction at the cellular level.

These thresholds represent the fundamental physiological basis for nerve activation and regeneration. Illustrative embodiments use stimulation parameters configured to exceed these thresholds to ensure depolarization and activation of regenerative signaling pathways.

Threshold Determination and Fallback Operation

In various embodiments, stimulation amplitude is titrated relative to clinically meaningful thresholds to ensure selective activation of the target nerve while preserving comfort and safety. For motor nerves (e.g., perineal, inferior rectal, levator ani branches), the amplitude is set at or slightly above the contraction threshold, defined as the minimum intensity that produces a visible or palpable contraction of the innervated muscle. The contraction threshold provides an objective anchor that confirms motor unit recruitment and action potential generation in the target axons. In awake patients, visual or palpable confirmation is preferred. In sedated or anesthetized patients, the contraction threshold may be verified by the operating clinician via direct observation or palpation.

For sensory nerves, stimulation is typically delivered below or near the sensation threshold to avoid discomfort while engaging sensory pathways. Sensation threshold is the minimum intensity at which the patient perceives the stimulus (e.g., tingling or a faint urge-related sensation). In practice, the amplitude may be set to a fixed percentage below sensation threshold (for example, ~5-15% below) to standardize comfort while maintaining neuromodulatory efficacy. For autonomic targets (e.g., vagus, cardiac, renal, cavernous), thresholds are tied to physiological markers (e.g., heart rate modulation, blood pressure change, blood flow), and intensity is titrated to the physiological threshold required to elicit a measurable, organ-specific response without overshoot.

Various embodiments also provide fallback strategies for cases in which immediate functional signs are absent due to severe injury or anesthesia. If visible contraction is absent, the system (or clinician) may use the EMG threshold as an objective surrogate for motor unit activation, provided that some motor units remain functional. If both contraction and EMG signals are absent (e.g., complete axonal discontinuity), or sensation is unavailable (e.g., sedation) and physiological markers do not apply (e.g., purely somatic motor target), the amplitude may be set using default parameter scaling derived from nerve size/type and established safety bounds. In such cases, the therapy is delivered within the claimed windows (e.g., frequency~20-100 Hz; pulse width~100-500 μs; pulse-train duration~3-60 s; rest~1-5 min; trains/session~1-8), and follow-up assessments verify downstream evidence of regeneration/remyelination and functional improvement (e.g., urethral closure pressure increase, leak reduction).

These threshold-based and fallback procedures are integrated within the progressive regimen of the system to maintain comfort and minimize fatigue. Amplitude is constrained below the pain threshold, and, where appropriate, within each session, trains are separated by rest intervals to allow neuromuscular recovery. Over a multi-week course, parameters (e.g., number of trains per session or train duration) may be adjusted gradually to sustain the biological triggers for axonal regrowth and Schwann-cell remyelination while preserving tolerability.

Dynamic Threshold Behavior Over Time

Thresholds for nerve activation are not static. Instead, threshold can change significantly during the course of therapy and recovery. After an injury, conduction properties of the nerve and surrounding tissue evolve as regeneration and remyelination progress. Initially, stimulation may require higher amplitudes to overcome conduction block or demyelination. As axonal continuity improves and Schwann cells restore myelin sheaths, the nerve becomes more excitable, and the effective threshold for contraction or sensation typically decreases. Conversely, in cases of scar tissue formation or fibrosis, thresholds may increase due to altered impedance and reduced current penetration.

Illustrative embodiments account for these dynamic changes by incorporating threshold-based titration and progressive regimens. Amplitude can be adjusted over time to maintain stimulation at or slightly above the relevant threshold, whether contraction threshold for motor nerves, sensation threshold for sensory nerves, or physiological threshold for autonomic nerves, without exceeding tolerability limits. This adaptive approach ensures consistent activation of regenerative signaling while minimizing discomfort and fatigue as the nerve heals.

FIG. 1C illustrates the various grades of peripheral nerve injury that may be treated using illustrative embodiments. The figure shows the structural organization of a normal peripheral nerve and the progressive degrees of damage that can occur in response to trauma, disease, or other pathological processes. A normal peripheral nerve includes individual axons surrounded by myelin sheaths with intervening nodes of Ranvier. The axons are enclosed within layers of connective tissue, namely, the endoneurium, perineurium, and epineurium, that collectively protect and organize nerve fascicles.

As shown in FIG. 1C, a Grade I (Neuropraxia) injury involves a localized conduction block due to myelin disruption without structural damage to the axon. The axon remains intact within continuous endoneurial, perineurial, and epineurial sheaths. Recovery from neuropraxia primarily requires remyelination, in which Schwann cells regenerate the myelin sheath to restore normal electrical conductance.

A Grade II (Axonotmesis) injury involves disruption of the axon while the surrounding connective tissue remains intact. In this scenario, the distal segment undergoes Wallerian degeneration while the proximal neuron initiates axonal regeneration to re-establish continuity. Because the endoneurial tube remains structurally preserved, axonal sprouts can follow the original pathway toward the target tissue, promoting functional recovery.

In Grade III (Neurotmesis) injuries, both the axon and the endoneurium are disrupted, while the perineurium and epineurium remain intact. The absence of intact endoneurial guidance increases the likelihood of misrouted axonal regrowth or neuroma formation. Recovery therefore depends on coordinated regeneration and remyelination, often supported by external stimulation or surgical repair.

A Grade IV (Neurotmesis) injury extends through the perineurium and affects the integrity of the fascicular boundary, while the epineurium may remain partially intact. Fibrotic scarring may form at the lesion site, creating a physical barrier that prevents normal axonal extension. Restoration in this case requires active repair that encompasses bridging the gap, encouraging axon regeneration, and re-establishing myelin continuity through remyelination.

A Grade V (Neurotmesis) injury represents a complete transection of the nerve trunk, where all layers, axon, endoneurium, perineurium, and epineurium, are disrupted. The proximal and distal segments are fully separated, and spontaneous regeneration is extremely limited. Effective treatment requires surgical approximation or grafting, followed by guided axonal regeneration and remyelination to restore function.

Nerve injury can arise from multiple causes, including mechanical trauma such as laceration, crush, or stretch injury; surgical or obstetric complications; prolonged compression or entrapment; ischemic damage from vascular compromise; metabolic disorders such as diabetes; toxic exposure from chemotherapy or heavy metals; inflammatory neuropathies; and degenerative or hereditary conditions. Infectious agents such as herpes zoster or Lyme disease, and tumor invasion or radiation-induced fibrosis, can also contribute to nerve damage. Regeneration is defined as the growth of an axon from the neuron to restore continuity of the nerve pathway. This process occurs when the axon itself is damaged or disconnected, such as in axonotmesis (Grade II) or neurotmesis (Grades III-V). Regeneration involves axonal sprouting from the proximal stump, guided by Schwann cells and extracellular matrix molecules toward the distal target, at a rate of a few millimeters per day.

Remyelination refers to the restoration of the myelin sheath surrounding axons to permit efficient electrical conduction. This process primarily occurs in neuropraxia (Grade I), where demyelination occurs without axonal damage, but also follows regeneration in more severe injuries once new axons have formed. Schwann cell proliferation and differentiation play key roles in this process, and electrical stimulation has been shown to enhance Schwann cell activity, promoting faster and more complete remyelination.

Repair is a broader term encompassing both regeneration and remyelination, as well as the restoration of vascular and connective tissue structures that support nerve function. Repair processes operate across all grades of injury and may include angiogenesis, fibroblast-mediated remodeling, and surgical reconstruction of perineurial or epineurial layers. Repair thus represents the umbrella process through which the structural and functional integrity of the nerve is restored.

In various embodiments, implanted stimulators and sensors can be configured to support and accelerate these biological processes. For example, electrical stimulation may be applied to promote remyelination in cases of neuropraxia, to encourage axonal regeneration following axonotmesis or neurotmesis, and to stimulate vascular and tissue repair in more severe lesions. Closed-loop systems can monitor nerve or muscle responses and dynamically adjust stimulation parameters to optimize the repair process. By integrating targeted neuromodulation with physiological feedback, the system can enhance natural regenerative mechanisms and improve recovery outcomes across the full range of nerve injury types illustrated in FIG. 1C.

In the field of neuromodulation, there exists significant inconsistency and ambiguity in the way terms such as "repair," "remyelination," and "regeneration" are used. Many references, both in the patent literature and in scientific publications, employ these terms without clear definition or without delineating the biological distinctions among them. As a result, it is often unclear what specific physiological process is being addressed or achieved by a given neuromodulation system or method.

For example, certain disclosures in the art describe "nerve repair" as encompassing all forms of recovery, without specifying whether the underlying mechanism involves restoration of myelin, axonal regrowth, or structural reconstruction of connective tissue layers. In other instances, the term "regeneration" is used interchangeably with "repair," even though regeneration properly refers to axon elongation and re-establishment of continuity between the proximal and distal nerve segments. Conversely, other disclosures treat "remyelination" and "regeneration" as separate and independent therapeutic goals, yet fail to clarify whether stimulation is directed toward Schwann cell activation (for myelin repair) or axonal outgrowth (for neural regeneration).

This inconsistent usage creates confusion in interpreting the true scope and functionality of existing neuromodulation technologies. Some systems claim to promote "nerve regeneration" when, in fact, their mechanisms of action appear limited to the restoration of conduction via remyelination of intact axons. Others refer to "nerve repair" while providing no evidence or mechanism indicating the re-growth or reconnection of severed axons. As a result, it is frequently indeterminate whether such systems are designed to promote electrophysiological recovery (restoration of signal transmission), structural recovery (tissue reconstruction), or both.

Illustrative embodiments, by contrast, provide clear distinctions among these biological processes. As used herein, "regeneration" refers specifically to the growth of a new axon from the proximal neuron to re-establish continuity with the distal target. "Remyelination" refers to the restoration or reformation of the myelin sheath around axons, whether intact or newly regenerated, to restore proper conduction velocity. "Repair" is used as a broader umbrella term encompassing either, or both, regeneration and remyelination, as well as restoration of the structural and vascular support tissues that maintain nerve integrity. By explicitly defining these terms and correlating them with known grades of nerve injury (as shown in FIG. 1C), the present disclosure eliminates ambiguity and provides a consistent biological framework for describing and implementing neuromodulation-based therapeutic interventions.

Damage to peripheral nerves can manifest in numerous ways depending on the type of nerve affected, the location of injury, and the severity of the disruption. Nerves serve as bidirectional conduits between the central nervous system and peripheral targets, transmitting both motor commands and sensory feedback. Accordingly, injury to motor nerves can lead to weakness, paralysis, or loss of voluntary muscle control, while injury to sensory nerves can result in numbness, tingling, burning, or chronic neuropathic pain. Injury to mixed nerves, which contain both motor and sensory fibers, can produce combinations of these symptoms, often accompanied by secondary autonomic disturbances such as changes in sweating, temperature regulation, or vascular tone in the affected region.

Peripheral nerves can be damaged by a wide variety of causes. Mechanical trauma, such as stretching, compression, or laceration, can occur during accidents, orthopedic injuries, or surgical procedures. Compression neuropathies may arise gradually, for example, in the median nerve of the wrist (carpal tunnel syndrome) or the peroneal nerve at the fibular head. Ischemic injury may result from prolonged pressure or vascular compromise, leading to hypoxia of the nerve fibers. Inflammatory or metabolic disorders, including diabetes, autoimmune neuropathies, and chronic inflammatory demyelinating polyneuropathy, can also degrade nerve integrity. A particularly relevant example is obstetric trauma, where excessive stretching or compression during childbirth can injure pelvic nerves such as the pudendal nerve or inferior rectal nerve, resulting in urinary or fecal incontinence, pelvic floor weakness, or altered sensory perception. These examples illustrate that both acute and chronic forces can compromise nerve structure and function.

The severity of nerve damage influences the extent and nature of functional impairment. Mild injuries, such as neuropraxia (Grade I), may involve temporary myelin disruption without axonal loss, resulting in transient conduction block and spontaneous recovery following remyelination. More significant injuries, such as axonotmesis (Grade II), involve axonal severance while preserving connective tissue scaffolds, requiring axonal regeneration to restore continuity. Severe injuries, such as neurotmesis (Grades III-V), disrupt both axons and surrounding endoneurial, perineurial, or epineurial layers, often creating fibrotic gaps that impede regrowth and necessitate surgical intervention. The functional consequences of these injuries may include loss of voluntary motor control, diminished reflexes, sensory loss, abnormal muscle tone, or chronic pain due to aberrant neural firing or misdirected reinnervation.

Assessment of nerve damage severity can be accomplished using a combination of clinical evaluation and diagnostic testing. Physical examination may identify weakness, atrophy, loss of sensation, or altered reflexes corresponding to the affected nerve distribution. Electrophysiological studies, such as electromyography (EMG) and nerve conduction velocity (NCV) testing, can quantify signal transmission and identify whether conduction block, demyelination, or axonal loss has occurred. Ultrasound and magnetic resonance neurography (MRN) can visualize structural discontinuities, swelling, or scarring within the nerve pathway. In some cases, evoked potential testing may be employed to evaluate sensory and motor pathway integrity, and histological analysis of biopsied tissue may confirm the extent of axonal degeneration or demyelination. Together, these diagnostic modalities provide an objective framework for classifying injury severity and for determining appropriate therapeutic approaches, including the use of targeted neuromodulation to promote repair (i.e., remyelination, and/or regeneration).

FIG. 1D illustrates the neuroanatomy of the pelvic floor from a caudal view, divided into two layers for clarity. The left side of the drawing represents the superficial layer, showing structures such as the perineal membrane, Colles' fascia, superficial perineal nerve, and dorsal nerve to the clitoris. These nerves provide sensory innervation to the skin and external genitalia. The right side of the drawing depicts a deeper layer, including the pudendal nerve, deep perineal nerve, and inferior rectal nerve, which supply motor innervation to the pelvic floor muscles and sphincters. These distal branches are critical for maintaining continence and sexual function. Injury to these nerves can lead to significant dysfunctions such as stress urinary incontinence (SUI), overactive bladder (OAB), fecal incontinence, and sexual dysfunction, including loss of sensation or dyspareunia.

In various embodiments, the system employs a family of epineurial neuroclips, described below as atraumatic, self-closing, multi-contact cuffs, that couple to a nerve by caliber and compliance, with exemplary categories including micro-clip (~0.8-2 mm inner diameter), small (~2-4 mm), medium (~3-6 mm), large (~6-12 mm), and macro-clip (≥12 mm). Each clip may support monopolar, bipolar, or tripolar stimulation and closed-loop sensing via multiple contacts arrayed around the inner lumen.

The nerves shown in the pelvic floor are provided as an illustrative example and serve as proof of concept for the disclosed methods. The inventors believe that the stimulation patterns and techniques described herein are broadly applicable to peripheral and autonomic nerves throughout the body. The objective is to promote nerve regeneration and remyelination, thereby restoring motor, sensory, and/or autonomic function following injury or disease. Target nerves include, but are not limited to, pelvic nerves (e.g., pudendal, perineal, inferior rectal nerve, dorsal nerve of the clitoris), limb nerves (e.g., median, ulnar, radial, femoral), autonomic nerves (e.g., cardiac, vagus, renal, cavernous, hepatic), and cranial nerves (e.g., III, IV, VI). These nerves vary in origin, size, and function, yet share common regenerative challenges that can be addressed through controlled electrical stimulation protocols as disclosed herein.

As non-limiting examples, nerves throughout the body may be repaired to varying degrees to restore beneficial functions. Illustrative examples are provided below:

Pelvic Nerves

Pudendal Nerve (S2-S4)

The pudendal nerve is a mixed motor and sensory nerve measuring approximately 3-5 mm in diameter. It innervates the muscles of the perineum and pelvic floor, including the external anal and urethral sphincters. Damage to the pudendal nerve can result in stress urinary incontinence (SUI), fecal incontinence, and sexual dysfunction due to loss of sphincter control and sensory feedback. In various embodiments, targeted electrical stimulation of the pudendal nerve promotes axonal regeneration and remyelination, restoring voluntary control of continence and improving sensory function.

Perineal Nerve (Terminal Branch of Pudendal)

The perineal nerve, 1.5-3.5 mm in diameter, provides motor and sensory innervation to structures within the urogenital triangle. Injury to this nerve can impair pelvic floor stability and reduce sensation in the perineal region, leading to discomfort and functional deficits. Illustrative embodiments apply patterned stimulation to the perineal nerve to restore both motor coordination and sensory perception.

Superficial Perineal Nerve (Terminal Branch of Perineal Nerve)

This sensory nerve, measuring 1-3 mm, supplies sensation to the skin of the urogenital triangle, including the scrotum, labia, and vagina. Damage may result in loss of tactile sensation and sexual dysfunction. Illustrative embodiments may deliver controlled stimulation to regenerate sensory fibers, restoring normal sensation and improving quality of life.

Deep Perineal Nerve (Terminal Branch of Perineal Nerve)

The deep perineal nerve, 1-3 mm in diameter, provides motor innervation to muscles such as the bulbospongiosus, ischiocavernosus, superficial transverse perineal muscles, and the external urethral sphincter. Injury can lead to compromised pelvic floor strength and urinary control. Embodiments stimulate this nerve to restore muscle tone and sphincter function.

Dorsal Nerve of the Clitoris (Terminal Branch of Pudendal)

This sensory nerve, 2-3.2 mm in diameter, innervates the clitoris, particularly the glans. Damage can cause loss of sexual sensation and reduced sexual function. Embodiments apply regenerative stimulation to restore sensory integrity and improve sexual health.

Inferior Rectal Nerve (Terminal Branch of Pudendal)

The inferior rectal nerve, 1-3 mm in diameter, provides motor innervation to the external anal sphincter. Injury results in fecal incontinence and impaired bowel control. Embodiments stimulate this nerve to restore sphincter function and continence.

Levator Ani Nerve (S3-S5)

This motor nerve, 2-3 mm in diameter, innervates the levator ani and coccygeus muscles, essential for pelvic floor support. Damage can lead to pelvic organ prolapse and reduced core stability. Embodiments target this nerve with stimulation to regenerate fibers and restore pelvic support.

Pelvic Sensory Branches (Superficial Perineal Nerve; Dorsal Nerve of the Clitoris; Selected Perineal Cutaneous Branches, ~1-3 mm).

In some embodiments, these nerves are instrumented with a micro-clip or small clip configured for delicate sensory fibers and thin epineurium. The clip provides closely spaced, low-impedance contacts to enable precise, low-current delivery and stable sensing. Because these are sensory nerves, the system determines amplitude using a sensation threshold, i.e., the lowest current at which the patient perceives a defined stimulus (or an objective surrogate such as somatosensory-evoked responses). Operating amplitude is set just above the sensation threshold and remains within the 0.1-10 mA range, typically toward the lower portion of that range for smaller-caliber nerves. Illustrative embodiments apply patterned stimulation to promote regeneration and remyelination and thereby restore tactile discrimination and sexual sensation while minimizing off-target activation.

Pelvic Motor Branches (Deep Perineal Nerve, Inferior Rectal Nerve, Levator Ani Nerve, ~1-3 mm) and Mixed Pudendal Trunk (3-5 mm).

In various embodiments, small to medium clips are utilized, with slightly longer contact arrays to support tripolar focusing around sphincteric and pelvic floor motor fibers. For motor nerves, amplitude is governed by a contraction threshold, e.g., the lowest current that elicits a reproducible increase in sphincter pressure, pelvic floor EMG activity, or visible contraction. Operating amplitude is set above contraction threshold and scaled within the 0.1-10 mA range (generally higher than for purely sensory branches as caliber increases). These embodiments deliver stimulation patterns that encourage axonal regrowth and remyelination while restoring continence and pelvic support.

Limb Nerves

Median Nerve (C5-T1)

The median nerve, 9-10 mm in diameter, controls forearm flexion and thumb opposition. Injury can cause loss of grip strength and dexterity. Embodiments stimulate the median nerve to restore motor function and sensory feedback in the hand.

Ulnar Nerve (C7-T1)

The ulnar nerve, 6-7 mm in diameter, enables wrist flexion and adduction. Damage results in impaired hand coordination and weakness. Embodiments apply stimulation to regenerate fibers and restore fine motor control.

Radial Nerve (C5-T1)

The radial nerve, 4-5 mm in diameter, controls extension of the elbow, wrist, and fingers. Injury leads to wrist drop and reduced arm function. Embodiments stimulate the radial nerve to restore extension strength and coordination.

Femoral Nerve (L2-L4)

The femoral nerve, 2.5-10 mm in diameter, innervates hip flexors and knee extensors. Damage causes difficulty walking and standing. Embodiments target this nerve to restore lower limb strength and mobility.

Limb Mixed Nerves (Median 9-10 mm; Ulnar 6-7 mm; Radial 4-5 mm; FEMORAL 2.5-10 mm).

For upper- and lower-limb mixed nerves, various embodiments employ medium to large clips that incorporate strain-relief features and multi-column contact sets to steer current and reduce activation of off-target fascicles. Because these nerves carry both motor and sensory fibers, amplitude control can use either (a) contraction threshold (e.g., onset of thenar, interosseous, wrist/finger extensor, quadriceps activation measured by EMG or torque) and/or (b) sensation threshold (patient report or evoked-potential markers). The operating amplitude is set above the measured threshold(s) and scaled within 0.1-10 mA, tending toward the higher end for larger diameters (e.g., median/ulnar) while respecting patient-specific thresholds. Stimulation patterns within the application's guidelines are used to restore grip strength, dexterity, and limb proprioception as regeneration proceeds.

Autonomic Nerves

Cardiac Nerves (Stellate Ganglia)

These autonomic nerves, 0.8-1.5 mm in diameter, regulate heart rate. Damage can lead to arrhythmias and impaired cardiac function. Embodiments stimulate cardiac nerves to restore autonomic control and normalize heart rhythm.

Vagus Nerve (Medulla Oblongata)

The vagus nerve, 2-4 mm in diameter, decreases heart rate and provides sensory input from internal organs. Injury can cause dysautonomia and impaired visceral regulation. Embodiments apply stimulation to restore autonomic balance and organ function.

Renal Nerve (Celiac and Aorticorenal Ganglia)

The renal nerve, 1-2 mm in diameter, regulates renal function and blood pressure. Damage can lead to hypertension and kidney dysfunction. Embodiments stimulate this nerve to restore renal homeostasis.

Cavernous Nerve (Hypogastric Ganglia)

The cavernous nerve, 0.8-1.5 mm in diameter, mediates erectile function. Injury results in erectile dysfunction. Embodiments apply stimulation to regenerate fibers and restore sexual function.

Hepatic Nerve (Medulla Oblongata, Celiac Ganglia)

The hepatic nerve, 0.8-1.5 mm in diameter, regulates liver metabolism. Damage can impair metabolic processes. Embodiments stimulate this nerve to restore hepatic function.

Autonomic Small-Caliber Nerves (Cardiac, Vagus, Renal, Cavernous, Hepatic; ~0.8-2 mm).

In some embodiments, micro-clips with narrow lumens and high-specificity contact geometry are used to localize current to small autonomic trunks. Because autonomic fibers do not yield skeletal muscle contraction or conscious sensation, the system sets amplitude using a physiological (functional) threshold tied to the nerve's target organ: e.g., change in heart rate or rhythm (cardiac/vagal), blood pressure or renal perfusion/diuresis (renal), erectile tumescence/pressure (cavernous), or metabolic/portal flow indices (hepatic). The operating amplitude is selected just above the detected physiological threshold and modulated within 0.1-10 mA, typically at the lower end for these small nerves.

Facial Nerves

Cranial Nerves III, IV, and VI (Midbrain and Pons)

These motor nerves, 2-3 mm in diameter, control eye movements. Damage causes diplopia and impaired ocular motility. Embodiments stimulate these nerves to restore coordinated eye movement and visual function.

Ocular Motor Cranial Nerves (III, IV, VI; ~2-3 mm).

For extraocular motor nerves, various embodiments utilize a small clip with directional, multipolar contacts to limit current spread and avoid neighboring structures. Amplitude is determined by a contraction threshold based on oculographic measures (e.g., minimal evoked saccade or tonic alignment change) and fine-tuned to prevent diplopia during therapy. Operating current remains within 0.1-10 mA and above threshold, with stimulation patterns chosen per the application to foster remyelination and restore coordinated ocular motility.

Very Large Mixed Nerves (e.g., Sciatic, Macro-Clip Example).

To illustrate scalability, in embodiments addressing very large nerves such as the sciatic, a macro-clip with multiple circumferential contact columns may be used. The same stimulation parameter families described in this application apply; however, amplitude is scaled upward within the 0.1-10 mA range according to patient-specific thresholds (motor contraction and/or sensation) rather than size alone. In practice, threshold-guided, closed-loop control (e.g., EMG onset, torque, and/or patient sensation) determines the appropriate setting, ensuring adequate recruitment for regeneration while maintaining safety and comfort.

Threshold-Driven, Patient-Specific Control.

Across various embodiments, nerve type dictates the operative threshold used to set amplitude: contraction threshold for motor fibers, sensation threshold for sensory fibers, and physiological (functional) threshold for autonomic fibers tied to the relevant organ function (e.g., heart rate, breathing rate, stool movement, blood flow, metabolic markers). Amplitude is then maintained just above the measured threshold and adapted over time as healing progresses, remaining within 0.1-10 mA and within the general stimulation pattern guidelines disclosed herein (with frequency, pulse width, duty cycle, and waveform shape selected per the application). This threshold-first, patient-specific approach ensures that embodiments scale naturally from the smallest autonomic nerve to the largest mixed trunk while providing the conditions that promote regeneration and remyelination and restore the intended function.

Systemic and Central Demyelination Context (Non-Limiting)

Multiple Sclerosis (MS; Central Nervous System Demyelination).

MS is the most common demyelinating disorder of the central nervous system (CNS) and typically requires central and/or systemic therapeutic strategies. In various embodiments, the inventors contemplate peripheral-to-central neuromodulation as a complementary or adjunctive approach. Specifically, stimulation of peripheral afferents (e.g., somatosensory branches listed above) and/or autonomic pathways (e.g., vagus nerve using a small neuroclip) is configured to engage central circuits and neuro-immune pathways that influence myelination, inflammation, and plasticity.

Amplitude remains within 0.1-10 mA and is set above the relevant threshold for the instrumented nerve: sensation threshold for cutaneous/sensory branches, contraction threshold for motor branches, and a physiological (functional) threshold for autonomic fibers (e.g., change in heart rate or heart-rate variability for vagus, respiratory modulation, or other organ-specific markers). In some embodiments, closed-loop operation further references central functional readouts (e.g., somatosensory-evoked potentials, gait metrics, or cognitive task performance) to titrate therapy. These embodiments do not supplant central therapies but provide peripheral entry points that may beneficially modulate CNS myelination and network function through activity-dependent and neuro-immune mechanisms.

Guillain-Barré Syndrome (GBS; Acute PNS Demyelination).

GBS is an acute, often rapidly progressive peripheral nervous system demyelinating neuropathy. In various embodiments, following or alongside standard medical care, micro, small, medium, or large neuroclips (depending on the specific nerve caliber) are placed on affected mixed or motor nerves (e.g., radial, ulnar, median, femoral) to promote regeneration and remyelination and to preserve muscle recruitment during recovery. Amplitude is maintained just above contraction and/or sensation thresholds within 0.1-10 mA and adjusted with closed-loop EMG and sensory feedback. For associated autonomic dysfunction, a micro-clip on an autonomic nerve (e.g., vagus) may use physiological thresholds (heart rate, blood pressure) to titrate stimulation. These embodiments aim to accelerate functional restoration (strength, dexterity, gait) while minimizing off-target activation.

Chronic Inflammatory Demyelinating Polyneuropathy (CIDP; Chronic PNS Demyelination).

CIDP features ongoing demyelination and remyelination with chronic weakness and sensory loss. Various embodiments implement repeatable, session-based stimulation of the involved mixed and motor nerves with small-to-large neuroclips matched to caliber. Amplitude is set above contraction and/or sensation thresholds and adjusted over time within 0.1-10 mA as thresholds shift with recovery. Protocols leverage the application's general stimulation guidelines (frequency, pulse width, duty cycle, waveform) and closed-loop adaptation (EMG for motor recruitment; evoked potentials or patient report for sensation), with the objective of stabilizing and enhancing conduction, muscle strength, proprioception, and endurance.

Charcot-Marie-Tooth Disease (CMT; Hereditary PNS Demyelination).

CMT encompasses inherited neuropathies with diffuse demyelination and distal weakness. In some embodiments, micro-, small-, or medium-sized neuroclips are placed on distal mixed nerves (e.g., peroneal, tibial, ulnar/median) to support activity-dependent remyelination and maintain motor unit recruitment. Amplitude is titrated just above contraction and/or sensation thresholds within 0.1-10 mA, often at the lower-to-mid range to avoid fatigue or discomfort in chronically denervated muscles and hypoesthetic skin. Over time, closed-loop algorithms adapt parameters to patient-specific changes in thresholds, nerve conduction, and functional endpoints (e.g., grip strength, timed walking).

Organ-Function—Autonomic Control (Applies Across MS Adjunctive Use and PNS Disorders).

For autonomic targets, the "right setting" is defined by physiological function of the organ subserved by the nerve. Thus, for the vagus nerve, the controller references heart rate or respiratory metrics; for cardiac nerves, rate/rhythm; for renal nerves, blood pressure, renal perfusion, diuresis; for cavernous nerves, tumescence/intracavernosal pressure; and for hepatic nerves, flow or metabolic indices (and, where relevant, immune metrics such as T-cell activity or cytokine patterns for spleen-related pathways). The system increases amplitude from the lower range to the higher range as needed to pass the physiological threshold, always remaining within 0.1-10 mA and under closed-loop control. In this way, nerve size informs the initial range, but patient-specific thresholds ultimately determine final settings.

Unified Threshold Statement

Depending on nerve type, the operative threshold is contraction (motor), sensation (sensory), or physiological/functional (autonomic). In various embodiments, amplitude is maintained just above the corresponding threshold and scaled within 0.1-10 mA; for very large trunks (e.g., sciatic with a macro-clip), amplitude is scaled upward within that range as required by thresholds, not by size alone. Frequency, pulse width, duty cycle, and waveform conform to the general guidelines described in the application, and the same families of parameters are used across peripheral and peripheral-to-central adjunctive embodiments.

Figure 2:
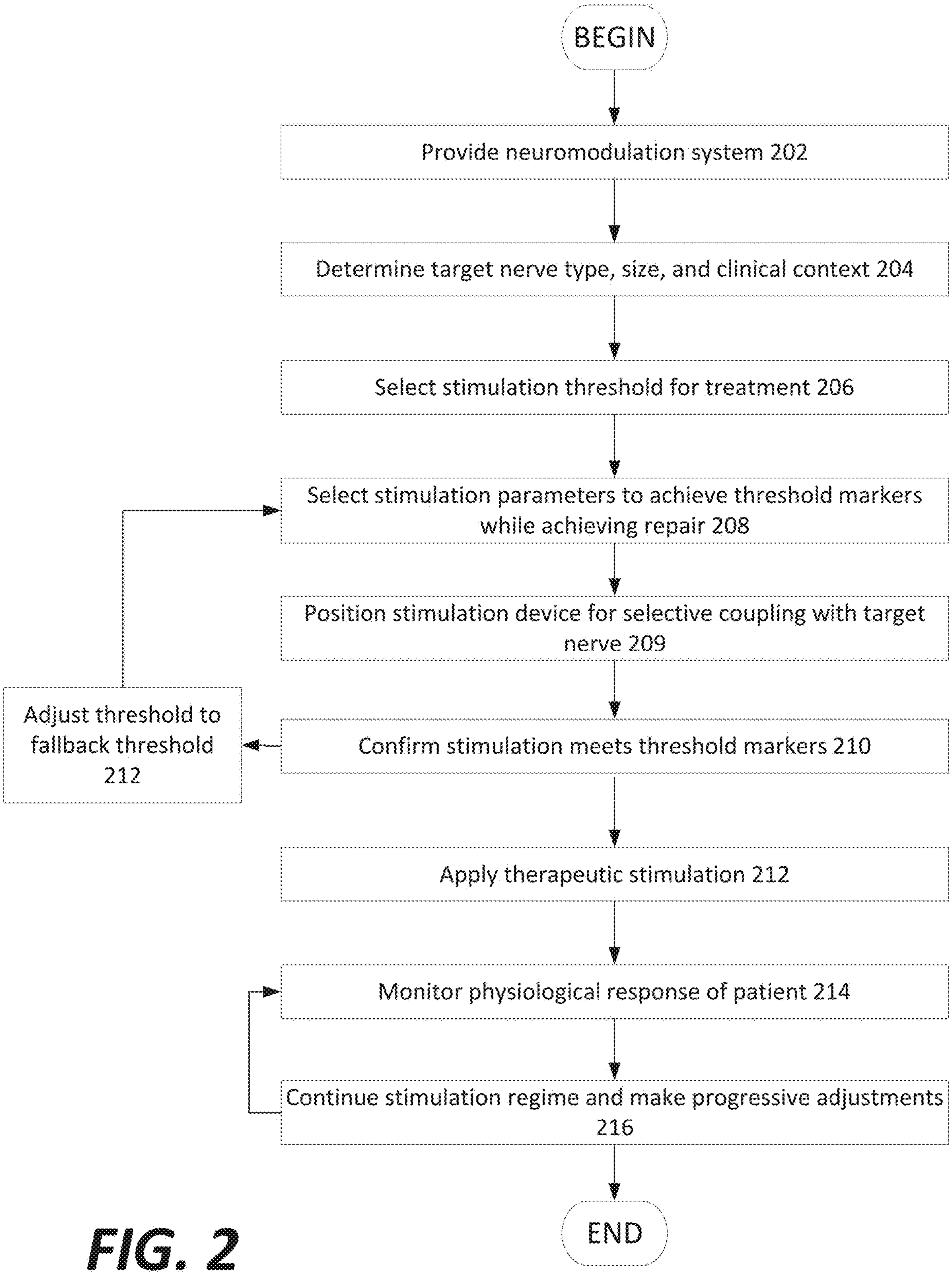
FIG. 2 shows a process for nerve repair in accordance with illustrative embodiments.

FIG. 2 shows a process for nerve repair in accordance with illustrative embodiments. The figure illustrates the decision process used to select stimulation amplitude by nerve type, including primary thresholds (contraction, sensation, physiological) and fallbacks (EMG threshold; default parameter scaling based on nerve size/type) when immediate functional signs are absent. Safety (below pain threshold), fatigue-avoidance (pulse-train with rest), and progressive adjustments over weeks are applied across all branches. Functional outcomes are used to confirm effect and to refine parameters within the claimed ranges.

It should be noted that this process is simplified from a longer process that normally would be used. Accordingly, the process likely has many steps that those skilled in the art likely would use. In addition, some of the steps may be performed in a different order than that shown. Additionally, or alternatively, some of the steps may be performed at the same time. Furthermore, some of these steps may be optional in some embodiments. Those skilled in the art therefore can modify the process as appropriate.

In various embodiments, a process of using the system for closed-loop stimulation begins at step 202, which provides a neuromodulation system. The system may include one or more neuromodulation devices (also referred to as a stimulators) configured to stimulate a target tissue (e.g. a nerve), and a controller configured to provide the therapeutic output as a function of the sensed signal. In various embodiments, the system includes one or more sensors 192 configured to sense a signal from a patient, The neuromodulation device 100 may be any of the devices discussed herein, and may include the primary neuromodulation device 100 with the satellite neuromodulation device(s) discussed further below.

In some embodiments, the controller is configured to receive data from one or more sensors 192 and uses the sensed data to modulate a therapeutic dosage. Various embodiments may refer to receiving data from the sensor, but it should be understood that reference to the sensor 192 in the singular also includes data receiving from one or more sensors. In some embodiments, the controller and/or the sensor 192 may be integrated into one or more of the neuromodulation devices. Additionally, or alternatively, the controller and/or the sensor 192 may be separate from one or more neuromodulation devices. In some embodiments, the controller and/or sensor 192 are external to the patient's body.

At step 204, the process determines the nerve type, size, and the patient clinical context. Peripheral nerves vary widely in size, composition, and function, and these differences dictate the appropriate stimulation parameters and threshold logic. For example, motor nerves such as the perineal or inferior rectal branches primarily control skeletal muscle contraction and require stimulation at or above the contraction threshold to ensure activation of motor units. In contrast, sensory nerves involved in afferent signaling for bladder or pelvic pain modulation are titrated relative to the sensation threshold, typically operating above or at this level to avoid discomfort while achieving neuromodulatory effects. Autonomic nerves, such as the vagus or cavernous nerves, do not produce visible contractions or patient-perceived sensations; instead, stimulation is referenced to a physiological threshold, defined by measurable organ responses such as heart rate modulation or blood flow changes.

The clinical context further influences threshold determination and parameter selection. Factors such as patient state (awake versus sedated), injury severity, nerve safety, and therapeutic goals maybe considered. In awake patients, thresholds can be identified through direct feedback (e.g., sensation reporting) or observation of muscle contraction during a visit with the clinician (or by the patient themselves in some embodiments). In sedated or anesthetized patients, where subjective feedback is unavailable, thresholds may be inferred from objective markers such as EMG activity, ENG activity, or physiological responses. In cases of severe nerve injury where conduction is absent and neither contraction nor sensation can be elicited, stimulation is delivered using default amplitude scaling based on nerve size and type, ensuring activation of regenerative signaling pathways even without immediate functional feedback.

By identifying nerve type and context, illustrative embodiments threshold-aware titration of stimulation parameters, ensuring selective activation of the target nerve while maintaining patient comfort and safety.

Accurate identification ensures selective coupling and effective regeneration or repair while minimizing unintended stimulation of adjacent structures.

In some embodiments, the target nerve is selected based on its physiological role and clinical relevance to the condition being treated. For example, motor nerves may be targeted for restoring muscular function, sensory nerves for restoring sensation, and autonomic nerves for restoring organ function. The identification process includes determining the nerve type and its anatomical location within the patient's body.

The method further includes assessing the physical characteristics of the nerve, such as its diameter, which typically ranges from approximately 1 mm to 25 mm for peripheral nerves. Nerve size serves as a practical surrogate for fascicle count, which is difficult to measure intraoperatively. The nerve may be identified visually during surgery, through imaging modalities, or by using nerve localization tools such as electrical nerve finders.

In addition to anatomical identification, the method includes evaluating the functional status of the nerve. The target nerve should exhibit impaired conduction, which may result from demyelination, axonal injury, or structural discontinuity. Examples of such injuries include neuropraxia, axonotmesis, and neurotmesis. Functional impairment can be confirmed by the absence or reduction of expected physiological responses, such as muscle contraction for motor nerves or sensory feedback for sensory nerves.

At step 206, after the nerve type and clinical context have been identified, the process selects the primary threshold that guides stimulation amplitude. This threshold represents the minimum intensity required to achieve a meaningful physiological response for the target nerve type and ensures selective activation without unnecessary overstimulation.

For motor nerves, the primary threshold is the contraction threshold, defined as the lowest amplitude that produces a visible or palpable contraction of the muscle innervated by the target nerve. This threshold provides an objective marker of motor unit recruitment and confirms that stimulation has exceeded the action potential threshold for the nerve fibers. In awake patients, contraction threshold is determined by gradually increasing amplitude until a contraction is observed. In sedated or anesthetized patients, contraction threshold may also be verified by palpation or supplemented with EMG monitoring.

For sensory nerves, the primary threshold is the sensation threshold, which is the lowest amplitude at which the patient perceives the stimulation, typically as a tingling or subtle contraction sensation. This threshold may be used to titrate afferent therapy for conditions such as overactive bladder, where stimulation is delivered at or above the sensation threshold to avoid discomfort while modulating sensory pathways.

For autonomic nerves, the primary threshold is a physiological threshold, defined by a measurable organ-specific response such as heart rate modulation, blood pressure change, or blood flow adjustment. This approach ensures selective activation of autonomic fibers without overshoot or adverse systemic effects.

At step 208, stimulation parameters are selected based on the selected threshold and within a range the inventors have discovered is configured to achieve repair. The inventors have determined that the stimulation parameters in Table 1 initiate nerve repair.

Unless specifically stated to the contrary, pulse trains or pulse bursts described in the application are those configured with such therapeutic parameters. Pulse sequences delivered for calibration, impedance checks, sensing, device warm-up, or other non-therapeutic purposes may also be employed in various embodiments, but these non-therapeutic sequences are not considered pulse trains or pulse bursts for purposes of determining the number delivered during a stimulation session.

For session-related descriptions, any reference to the number of pulse trains or pulse bursts delivered within a session refers solely to the number of therapeutic pulse trains or therapeutic pulse bursts delivered within that session. Pulse trains occurring within one hour of each other are considered part of the same session unless the context requires separate categorization.

Various embodiments of the invention include the delivery of between one and eight therapeutic pulse trains having at least the amplitude, frequency, and pulse burst duration outlined in Table 1 during each stimulation session. The number of therapeutic pulse trains within this range has been observed to produce a consistent and reproducible therapeutic response. Additional pulse trains may be delivered before, during, or after the session. However, any pulse train having parameters outside the therapeutic ranges of Table 1 is considered non-therapeutic and does not count toward the number of therapeutic pulse trains delivered in the session.

In some embodiments, the device is configured to deliver non-therapeutic pulse trains for purposes such as impedance measurement, calibration, titration, or device warm-up, among other things. These non-therapeutic pulse trains do not affect the determination of how many therapeutic pulse trains are delivered during a session because only pulse trains with parameters within the Table 1 therapeutic ranges are counted. Thus, a stimulation protocol may include any number of non-therapeutic pulse trains while still delivering one to eight therapeutic pulse trains in a session.

TABLE 1

| Parameter | Range |
|---|---|
| A. Parameters for nerve repair | |
| Pulse type (preferred) | Biphasic |
| Current Amplitude | 0.1 mA-5 mA |
| Pulse Width (preferred) | 150-500 μsec |
| Interpulse Delay (i.e., for non-monophasic) | 25-100 μsec |
| Frequency | 20-100 Hz |
| Pulse Burst Duration (per individual pulse burst) | 3-60 sec |
| Pulse Burst Quantity in Session (preferred) | 1-8 |
| Pulse Burst Intrasession Rest Duration | 0.5-5 min |
| Session Duration ((pulse burst duration + pulse rest duration) × (pulse burst quantity)) | 3 seconds to less than 1 hour per session |
| Pulse Burst to Rest Ratio | 1-200% |
| Number of Sessions Per Day (preferred) | 1 to 10 |
| Number of Days per Week to Run Sessions | 1 to 7 |
| Duration of Therapy Session | 33 sec (3 seconds without final rest) up to 48 minutes (including 8 cycles with rests) |
| Minimum rest time between sessions | 1 hour |
| B. Target nerve conditions | |
| Nerve Size | 1-25 mm |
| Nerve Definition | Any peripheral nerve |
| Nerve Fascicle Count | — |

For consistency and clarity, it should be understood that references in this application to "pulse trains," "pulse bursts," "bursts," or similar terms refer to therapeutic pulse trains or therapeutic pulse bursts unless the context expressly indicates otherwise. As used herein, a therapeutic pulse train or therapeutic pulse burst is a sequence of stimulation pulses having parameters within the therapeutic ranges identified in Table 1. These parameters, which include amplitude, pulse width, frequency, burst duration, and other controllable stimulation attributes, have been identified as effective for producing the desired nerve repair response.

After the appropriate threshold has been determined, whether contraction threshold for motor nerves, sensation threshold for sensory nerves, or physiological threshold for autonomic nerves, illustrative embodiments use this reference point to set stimulation parameters within safe and effective ranges described in Table 1. The amplitude is adjusted to operate at or slightly above the threshold for motor and autonomic nerves to ensure activation of action potentials and regenerative signaling, while remaining well below the pain threshold to maintain comfort. For sensory nerves, amplitude is typically set at or above the sensation threshold (e.g., approximately 5-15% below) while remaining under the pain threshold to avoid discomfort while achieving neuromodulatory effects.

Other parameters are selected to complement the amplitude setting and optimize biological outcomes while minimizing fatigue. For regeneration and/or remyelination, stimulation is delivered in short pulse trains of about 3-60 seconds at frequencies between approximately 20 Hz and 100 Hz, with pulse widths of about 150-500 microseconds. Each train is followed by a rest interval of about 1-5 minutes to allow neuromuscular recovery and prevent fatigue. A typical session may include 1-8 trains, with one or more sessions per day, repeated 1-7 days per week over a course of 2-20 weeks. However, some embodiments can provide improvement with a single stimulation session.

In various embodiments, the stimulation waveform comprises biphasic pulses to minimize charge accumulation and tissue damage. The current-controlled amplitude is adjustable within a range of approximately 0.1 mA to 10 mA, scaled according to nerve size and patient-specific threshold feedback. For smaller nerves (e.g., 1-3 mm diameter), amplitudes near the lower end of the range (e.g., 0.6-1.0 mA) may be sufficient, whereas larger nerves (up to 25 mm) may require higher amplitudes within the safe range. In practice, stimulation thresholds can vary significantly between intraoperative measurements and chronic implanted conditions due to changes in tissue environment, fluid regulation, and fibrotic encapsulation. It is generally observed that thresholds decrease after implantation and stabilization, enabling lower amplitudes for effective engagement compared to intraoperative values. Accordingly, stimulation parameters may be titrated to motor threshold or combined sensory-motor thresholds post-surgery to ensure on-target activation while minimizing fatigue and preserving safety margins.

Thresholds measured intraoperatively often differ from those observed under chronic implanted conditions due to changes in tissue environment, extracellular fluid, and fibrotic encapsulation. During surgery, stimulation thresholds may be elevated because of variable fluid presence and incomplete tissue stabilization. After implantation, thresholds typically decrease as the cuff settles and fibrotic tissue forms, improving current distribution and reducing impedance. Accordingly, thresholds established intraoperatively can serve as an initial reference but should be reassessed post-surgery and adjusted downward as desired. In practice, clinicians may set the threshold during implantation and fine-tune it during follow-up sessions based on patient feedback and observed physiological responses.

As an example, both the inferior rectal and perineal nerves are mixed somatic nerves (motor+sensory) with diameters in the 1-4 mm range. In this case, the inventors have found that effective stimulation amplitudes fall within 0.6-1 mA, scaled to nerve size and patient-specific thresholds. Because these nerves serve dual roles, motor control of pelvic floor muscles and sensory input from the perineal region, the threshold selection strategy prioritizes functional restoration while maintaining comfort.

For mixed nerves, the recommended approach is to use the motor contraction threshold as the primary reference, since motor recovery is often critical for continence and pelvic stability. This threshold is objectively verifiable (visible or palpable contraction of the anal sphincter or pelvic floor muscles) and ensures activation of motor fibers. Once contraction threshold is identified, amplitude is set slightly above this level but below the pain threshold. Sensory fibers will also be recruited at this setting, providing neuromodulatory benefits without excessive discomfort. If the patient is awake, contraction can be confirmed visually or by palpation; if sedated, EMG monitoring serves as a fallback. In cases where neither contraction nor sensation can be elicited (e.g., severe injury), amplitude defaults to size-based scaling within the safe range (e.g., 0.5-2 mA for a 2-3 mm nerve).

The pulse width for nerve repair is set between 150 μsec and 500 μsec, and the inter-pulse delay between 25 μsec and 100 μsec, providing adequate depolarization while maintaining safety margins. The stimulation frequency is typically between 20 Hz and 100 Hz, selected to promote axonal growth and Schwann cell activity without inducing fatigue or excessive heating. Therapy is delivered in pulse bursts lasting 3 to 60 seconds, followed by a rest interval of approximately 0.5 to 5 minutes, creating a controlled duty cycle that balances efficacy and energy efficiency.

The number of bursts per session and the overall session duration are calculated based on these parameters and the desired therapeutic effect. In various embodiments, the therapy may include 1 to 10 sessions per day, repeated 1 to 7 days per week, depending on the severity of nerve injury and clinical objectives. These parameters may be dynamically adjusted during treatment based on observed physiological responses, such as contraction threshold for motor nerves, sensation threshold for sensory nerves, or organ function markers for autonomic nerves.

Stimulation therapy is delivered using stimulation sessions configured to promote nerve regeneration while minimizing fatigue and energy consumption. Each session comprises pulse bursts delivered at a frequency of 20-100 Hz, with individual burst durations of approximately 3-60 seconds. The number of bursts per session is between one and eight, resulting in a total stimulation time of less than one hour per session. Between bursts, rest intervals of about 0.5-5 minutes allow recovery and reduce neuromuscular fatigue. Accordingly, the total stimulation duration, ranges from a few seconds to less than one hour, with selective nerve repair implementations advantageously falling between 1 and 8 minutes for most therapeutic applications.

This protocol contrasts with prior art approaches that require prolonged intraoperative stimulation (e.g., 8 minutes or more at low frequencies such as 2 Hz), which are impractical and less effective for chronic therapy. Experimental findings indicate that short bursts repeated over multiple sessions can initiate regenerative processes such as axonal repair and remyelination, even when cumulative stimulation time per session is minimal (e.g., four 15-second bursts totaling about 1-2 minutes). This therapy may be applied several times a day, daily or several times per week, over a course of 1-20 weeks, with flexibility to taper or maintain stimulation as desired to sustain functional recovery.

By applying stimulation above the relevant threshold for the nerve type, the inventors believe that the configured parameters induce action potentials in the target axons, triggering molecular pathways associated with regeneration and repair. This includes upregulation of pro-regenerative genes, initiation of axonal sprouting, and facilitation of remyelination by Schwann cells. The defined ranges ensure that stimulation remains selective, safe, and effective across a broad spectrum of peripheral nerve sizes and injury types.

In this step, stimulation parameters are selected to achieve therapeutic activation of the target nerve and promote repair. In various embodiments, the parameters are configured to exceed a defined threshold, such as contraction threshold for motor nerves, sensation threshold for sensory nerves, or physiological threshold for autonomic nerves, ensuring effective stimulation while maintaining safety and selectivity.

However, in various embodiments, confirmation of threshold markers may be optional. Instead of explicitly determining and verifying a threshold, the system may apply default regenerative parameters within the disclosed safe ranges (e.g., amplitude between 0.1 mA and 10 mA, frequency between 20 Hz and 100 Hz, pulse width between 150 μsec and 500 μsec). This approach enables therapy delivery without requiring objective or subjective threshold feedback, which may be desirable in scenarios where threshold determination is impractical or unnecessary.

While this alternative method can achieve nerve repair, it may result in unintended patient discomfort or muscle fatigue if stimulation remains at the upper end of the range. To mitigate this, the method optionally incorporates patient objective or subjective feedback, such as reports of pain, exhaustion, or discomfort, as an input for adjusting stimulation parameters. For example, if the patient experiences excessive fatigue during repeated contractions, amplitude or duty cycle may be reduced while remaining within the disclosed ranges. Similarly, if discomfort occurs, frequency or burst duration may be modified to improve tolerability without compromising therapeutic effect.

At step 209, the stimulation device is positioned to achieve selective direct coupling with the nerve. This selective placement ensures that the stimulation parameters applied in subsequent steps produce the desired regenerative and reparative effects without activating adjacent nerves. The stimulation device (e.g., device escribed below) is positioned to achieve direct, selective coupling to the identified target nerve while minimizing current spread to adjacent tissues.

The one or more neuromodulation devices are coupled to one or more corresponding nerves. In one embodiment, the target nerve is positioned into a stimulation chamber of a neuromodulation device. In some embodiments, the device 100 includes at least one movable arm that opens to permit passage of the nerve into the stimulation chamber. The arm closes to prevent or hinder the nerve from being dislodged from the stimulation chamber without overly compressing the nerve. In some embodiments, the movable arm is configured to retain nerves of a variety of sizes within the chamber (e.g., the chamber accommodates nerves of ranges of 0.3 mm-4 mm). In various embodiments, the arm is biased towards a closed or substantially closed position.

Additionally, the device 100 may be configured to retain nerves of different sizes in the chamber and in contact with one or more electrodes while applying an atraumatic retention force on the nerve. The channel similarly is configured to allow passage of the nerve therethrough. In some embodiments, the channel can yield to pressure from inserting the nerve, such that the channel opens or changes shape. The necessary pressure to open or deform the channel is configured to be less than a pressure that may damage the nerve. Additionally, or alternatively, the nerve is stretched in length causing its cross-sectional diameter to narrow to a point that it can pass through the channel. In some embodiments, both the channel and the nerve transiently deform to some degree to permit the nerve to pass through the channel. Details of illustrative embodiments are discussed below.

As discussed previously, various embodiments further selectively couple to and stimulate the peripheral nerve in areas near the distal end of the nerve (e.g., the last ¼th or ⅓rd length of the nerve, or where there are a small number of fascicles 1-3). This allows the use of a compact stimulation device 100 to deliver lower power stimulation directed at a specific nerve target without the risks of a potentially damaging, time intensive and/or traumatic surgical procedure. Prior art electrode arrays disadvantageously do not provide specific enough stimulation to the targeted nerve often resulting in unintended side effects (e.g. non-target nerve stimulation). Similarly, nerve cuffs disadvantageously are limited by pre-defined sizes, which often lead to suboptimal nerve electrical coupling when a cuff is not properly sized. Various embodiments disclosed herein advantageously provide greater assurance of electrical coupling to a target nerve for delivery of a selective stimulation signal and are placed with a simple implantation procedure.

Furthermore, various embodiments include a neuromodulation device 100 having a channel defined by a plurality of jaws or arms that are movable and/or deformable. The dimensions of the channel are adjustable to allow for entry of nerves of various sizes into the chamber, while also for securing the nerve within the chamber with electrode contact. Additionally, other sensors 192 may be coupled to relevant anatomy (e.g., EMG may be coupled to the corresponding muscle, etc.).

Sensors utilized for system triggering and/or feedback are coupled to relevant anatomy and may be located within or external to the patient's body. In some embodiments, the triggering and feedback sensors 192 are independent sensors. In some embodiments, the EMG sensor 192 placed over a specific muscle is utilized to trigger a nerve stimulator that is coupled to a nerve that stimulates the same muscle. When a patient 105 consciously tries to use the muscle, the output of the EMG sensor 192 changes which is detected as a muscular contraction by the nerve stimulation controller. The controller then stimulates the nerve that innervates the subject muscle to assist in muscle contraction. In some embodiments, the nerve stimulation system ends stimulation when the same or other sensors 192 detect that muscular contraction is complete (e.g. relative motion sensors 192 indicate that an orifice is closed). In another embodiment, nerve stimulation ends after a duration of muscular contraction time (e.g. voiding the bladder requires diaphragm and abdominal muscle contraction for an amount of time).

In various embodiments, the stimulation device includes an inner, atraumatic contact surface and one or more integrated electrodes disposed to face the epineurial surface when closed. The device is advanced to the target site under direct visualization, loupe magnification, or surgical microscopy, optionally assisted by nerve localization tools, and oriented such that its electrode(s) extend longitudinally or circumferentially relative to the nerve axis depending on the desired field geometry and selectivity.

The stimulator is closed around the nerve with a controlled closure force sufficient to maintain electrical contact without occluding perineural blood flow or reducing the cross-sectional area of the fascicles by more than 10%. In some embodiments, an applicator with a torque- or displacement-limiting mechanism is used to standardize the closure force across patients and nerve sizes (e.g., 1-25 mm diameter). The inner surface may include a compliant, biocompatible interface (e.g., silicone, polyimide, or similar elastomer) to conform to epineurial irregularities, while the electrode contact(s) comprise platinum, platinum-iridium, titanium nitride, or conductive polymer coatings configured to reduce impedance and improve charge transfer. The outer surface of the clip may be insulated to direct current density into the target nerve and away from neighboring structures, thereby enhancing selectivity.

Following mechanical coupling, electrical coupling is confirmed by delivering a brief low-amplitude test pulse train and observing a nerve-specific response. For motor nerves, appropriate placement is verified by visible or palpable target muscle contraction or by electromyographic (EMG) activity; for sensory nerves by patient-reported sensation (when applicable); and for autonomic nerves by a physiological marker associated with the innervated organ (e.g., transient change in heart rate, sphincter tone, or organ motility). If the observed response indicates off-target activation or inadequate contact, the clip is repositioned and re-secured until the desired selective response is obtained at a sub-therapeutic amplitude. In all cases, insulation of the clip body and maintenance of intimate epineurial contact are used to limit volume conduction and reduce activation of non-target nerves.

The device may further include strain-relief features and suture tabs or barbs to prevent migration, as well as integrated or adjacent conformal insulating body to electrically shield the operative field. Where appropriate, a return/reference electrode is positioned to complete the circuit in a geometry that favors current flow through the coupled nerve. After placement is confirmed, the surgical field is inspected to ensure that the clip does not overly compress the nerve, or interfere with surrounding tissues.

In various embodiments intended for short-term or intraoperative use, a temporary clip or percutaneous lead is positioned using the same atraumatic principles, optionally with biodegradable or trial-lead formats to deliver one or more therapy sessions and subsequently be removed or resorbed. In other embodiments intended for chronic therapy, the device is left in situ and connected to an implantable pulse generator or externalized connector, enabling delivery of the stimulation parameters described herein (e.g., biphasic pulses, 0.1-10 mA, 150-500 μsec, 20-100 Hz) in later steps. Proper positioning and coupling thus provide the selective interface for regenerative and reparative effects of the therapy while maintaining nerve integrity and patient safety.

In various embodiments, the stimulation device is not in direct contact with the target nerve but is positioned in close proximity to the nerve or a neurovascular bundle containing the nerve, such that stimulation is delivered by controlled volume conduction through interposed tissues (e.g., adventitia, perineural fat, fascia, vessel wall, and connective tissue). In these embodiments, the device is configured and operated to selectively activate the target nerve while avoiding activation of adjacent, non-target nerves by measuring and controlling stimulation based on nerve-specific thresholds, rather than relying on fixed amplitude or frequency values alone. Illustrative embodiments may position non-direct contact stimulation devices closer to the target nerve than to a non-target nerve.

For purposes of non-contact stimulation, a nerve activation threshold is defined as the minimum charge-per-phase (or current-pulse width combination) at the nerve required to elicit a nerve-specific physiological marker. The system treats output amplitude at the electrode as a means to reach the nerve's threshold, not as the threshold itself. Because intervening tissues attenuate and shape the electric field, the current delivered at the electrode may differ from the effective field at the nerve; therefore, stimulation parameters are adaptively titrated to achieve the same functional threshold at the nerve that would be obtained under direct contact, even though the electrode-side amplitudes may be higher and dependent on distance, tissue impedance, and electrode geometry.

Selectivity with non-direct contact may be achieved by a combination of: (i) proximity to the target nerve or neurovascular bundle; (ii) field shaping using insulation, guard electrodes, or return electrode placement to favor current density through the target nerve; (iii) closed-loop titration to threshold using nerve-specific biomarkers; and (iv) control of pulse parameters (e.g., pulse width, interphase interval, waveform asymmetry) to bias activation toward the intended fibers. In various embodiments, the device is positioned such that the shortest tissue path between the stimulating pole(s) and the target nerve is less than a predetermined distance (e.g., 0.5-1.5 mm), while the path to neighboring non-target nerves is longer or shielded, enabling selective activation at sub-side-effect levels.

At step 210, the process confirms whether the stimulation meets threshold via objective and/or subjective outcomes. This threshold ensures that stimulation is delivered at a level sufficient to induce the desired physiological effect without causing unnecessary discomfort or activating adjacent nerves. In some embodiments, the threshold is defined as the minimum amplitude at which a measurable response occurs in the target nerve. The specific response depends on the nerve type:

Motor Nerves: In various embodiments, the threshold is the contraction threshold, identified when the target muscle exhibits a visible or palpable contraction. This may be confirmed by direct observation, palpation, or electromyographic (EMG) monitoring. In sedated patients, EMG or visual cues are used to verify contraction in the absence of patient feedback.

Sensory Nerves: In various embodiments, for sensory nerve repair, stimulation is titrated to a sensation threshold, i.e., the minimal amplitude that produces a reproducible patient-reported sensation in the dermatome innervated by the target nerve (e.g., as tingling or pressure sensation). As sensory regeneration is believed to require depolarization of a sufficient number of sensory fibers, amplitudes set below the sensation threshold (e.g., ~10% under threshold) may fail to activate enough fibers to initiate or sustain repair and are therefore not preferred. Accordingly, therapy is administered at or above the sensation threshold, while remaining below the pain threshold and within safety limits.

When patient-reported feedback is unavailable or unreliable (e.g., anesthesia, acute postoperative setting, neuropathies with absent sensation), the system employs a backup thresholding strategy that does not rely on subjective sensation. In such embodiments, stimulation is delivered at a fixed, predetermined amplitude known to depolarize the target sensory nerve based on prior characterization (e.g., intraoperative motor co-activation thresholds, physiological correlates, or device-specific lookup values for nerve size and configuration). Initial intraoperative thresholds may be recorded as a reference and subsequently adjusted downward post-implantation as the peri-electrode environment stabilizes (e.g., fluid normalization and fibrotic encapsulation), while maintaining amplitudes sufficient to ensure fiber depolarization and avoiding under-treatment. This approach ensures that sensory targets are consistently driven to threshold or slightly above, enabling axonal repair and remyelination without requiring continuous patient feedback.

Autonomic Nerves: In various embodiments, the threshold is a physiological threshold, identified by monitoring an organ-specific functional marker. For example, stimulation of the vagus nerve may be confirmed by a transient change in heart rate, while stimulation of a gastrointestinal nerve may be verified by motility or sphincter tone changes.

When primary threshold markers are available, the markers are used to confirm that stimulation parameters are appropriate for selective nerve activation and therapeutic effect. For motor nerves, the presence of a visible or palpable contraction at the expected amplitude confirms that stimulation has reached or slightly exceeded the contraction threshold, ensuring activation of motor units and action potential generation in the target axons. This observation provides an objective reference for setting amplitude and validates that the selected frequency, pulse width, and train/rest architecture are sufficient to achieve neuromuscular engagement without overshoot.

For sensory nerves, patient-reported perception of stimulation, such as tingling or subtle contraction sensation, indicates that the sensation threshold has been reached. Various embodiments operate below or near this threshold for afferent therapy to avoid discomfort while maintaining neuromodulatory efficacy. Clinicians may confirm this by gradually increasing amplitude until the patient perceives the stimulus, then adjusting downward by a fixed percentage (e.g., 5-15%) to ensure tolerability. This process validates that stimulation parameters are aligned with patient comfort and therapeutic goals.

For autonomic nerves, physiological markers such as heart rate modulation or blood flow changes serve as confirmation that stimulation has reached the physiological threshold. These markers provide a functional indicator that autonomic fibers are activated, allowing clinicians to fine-tune amplitude and other parameters to achieve the desired organ-specific response without exceeding safety limits. By comparing observed responses to expected thresholds, illustrative embodiments ensure that stimulation parameters are both effective and safe.

In various embodiments, the system applies a series of low-amplitude test pulses and incrementally increases amplitude until the threshold response is observed. After the threshold is established, therapeutic stimulation is delivered at an amplitude above the threshold to ensure effective activation of the target axons. For motor nerves, this typically means stimulation above contraction threshold; for sensory nerves, above sensation threshold; and for autonomic nerves, above the physiological marker threshold.

Determining the threshold provides a patient-specific reference point for scaling stimulation parameters within the defined ranges (e.g., 0.1-10 mA amplitude, 150-500 μsec pulse width, 20-100 Hz frequency). This step ensures selectivity, safety, and efficacy, forming the basis for subsequent therapy sessions aimed at promoting nerve regeneration, remyelination, and functional recovery.

If primary threshold markers, such as visible muscle contraction for motor nerves or patient-reported sensation for sensory nerves, are not obtainable, the process continues to step 212, which adjusts the threshold. This can occur in sedated or anesthetized patients, or in cases of severe nerve injury where conduction is absent and functional signs cannot be elicited. Illustrative embodiments address these challenges by providing structured fallback strategies to ensure stimulation parameters remain effective and safe.

When contraction cannot be observed, the system or clinician may rely on electromyographic (EMG) threshold as an objective surrogate, provided that partial conduction remains. EMG detection confirms motor unit activation even in the absence of visible movement. If both contraction and EMG signals are absent, stimulation amplitude is set using default scaling based on nerve size and type, combined with empirically validated safety margins. For autonomic nerves or mixed injuries where neither contraction nor sensation applies, stimulation is titrated to physiological markers such as heart rate modulation or blood flow changes. If these markers are unavailable, conservative default parameters are applied within the claimed ranges for frequency, pulse width, and train/rest architecture.

Regardless of the fallback method used, various embodiments incorporate objective and subjective outcome verification to confirm therapeutic effect over time. Objective measures for a urinary incontinence example include urethral closure pressure, leak point pressure, fecal continence scores, and organ-specific physiological metrics. Subjective measures include patient-reported improvements in urgency, pain, or functional performance. These outcomes are monitored periodically and used to refine stimulation parameters within the claimed windows, ensuring that therapy remains effective even when initial threshold determination relies on fallback logic.

It should be apparent based on the above that, in addition to determining stimulation threshold based on contraction, sensation, or physiological markers, various embodiments may incorporate patient input as an alternative or supplemental criterion for setting stimulation parameters. This approach addresses scenarios where therapy is adjusted not solely to meet an objective threshold but to optimize patient comfort and minimize adverse effects such as fatigue or pain (in other words, to meet a subjective threshold).

In some embodiments, after initial stimulation confirms nerve activation, the system or clinician solicits feedback from the patient regarding comfort level. If the stimulation parameters, while technically above threshold, result in excessive muscle fatigue, discomfort, or pain, the amplitude, frequency, or duty cycle may be reduced within the disclosed safe ranges (e.g., 0.1-10 mA amplitude, 20-100 Hz frequency). This adjustment ensures that therapy remains tolerable while still delivering regenerative and reparative benefits.

Patient feedback may include indicators such as, muscle exhaustion during repeated contractions, pain or discomfort at the stimulation site or in the innervated region and/or functional interference, such as inability to perform daily activities due to overstimulation.

In various embodiments, the system integrates a user interface allowing patients to report discomfort or fatigue during therapy sessions. These inputs are processed alongside physiological data to dynamically adjust stimulation parameters without compromising therapeutic efficacy.

Upon placement of the stimulation device, the system may initiate a calibration routine configured to determine in situ activation thresholds for the target nerve and, where necessary, side effect thresholds for nearby non target nerves. During this routine, the controller may deliver incremental test pulses that increase charge per phase by modulating one or more threshold-relevant parameters, including pulse amplitude, pulse width, polarity, interphase delay, and pulse frequency.

For motor nerves, the biomarkers may include visible or palpable contraction of the innervated muscle, an electromyographic signal that exceeds a predefined signal to noise ratio, or the onset of an M wave. For sensory nerves, the biomarkers may include subject reported paresthesia that localizes to a target dermatome or an appropriate evoked potential signature. For autonomic nerves, the biomarkers may include a physiological marker change such as inflection of heart rate variability or a pressure or flow change in an innervated organ.

Based on these test pulses, the system determines a Target Threshold (T_target), defined as the lowest charge per phase, or the lowest amplitude and pulse width combination, that reproducibly elicits the intended pattern of activation, which may correspond to selective stimulation of a single physiological target or semi-selective stimulation of two or three physiological targets within a related anatomical region, depending on the programmed therapeutic objective. The same incremental stimulation sequence may be continued until activation is first detected outside the intended selective or semi-selective target set, such as the appearance of an unintended muscle response, an unintended paresthesia territory, or another non-target biomarker, thereby defining an Off-Target Threshold (T_OT). Because the threshold values depend on parameters that influence delivered charge and field distribution, including pulse polarity (biphasic or monophasic), pulse width, amplitude, interpulse characteristics, burst structure, and burst to rest ratio, the system may explicitly associate changes in any of these parameters with corresponding shifts in T_target or T_OT. Anatomical factors, including nerve size, nerve type, and fascicle count, may also be recorded or inferred, since these factors influence the field intensity required to depolarize the intended fibers and therefore directly affect threshold magnitude.

After the thresholds are established, the system may define a therapy window such that the therapy level is greater than or equal to T_target and less than T_OT, optionally with a margin (e.g., approximately 5 to 30 percent) to compensate for a variety of changes, including posture changes, hydration status, fibrosis, or other sources of physiologic variability. During therapy, the controller may maintain operation at or near T_target by issuing brief calibration pulses and adjusting threshold-relevant parameters in a closed loop manner whenever biomarker measurements indicate drift.

In non-contact embodiments, electrode geometry and return electrode placement may be configured to bias current flow toward the target nerve so that T_target is minimized and T_OT is maximized. For example, a monopolar near field configuration may be created using a small active electrode positioned near the nerve and a distant return electrode to generate a steep near field that peaks at the target. Alternatively, bipolar or tripolar focusing may be implemented by placing return or guard electrodes adjacent to the active electrode to collimate the electric field and reduce spread to nearby non target tissues. Conformal insulating body or shields composed of dielectric material may block current pathways toward non target regions to increase selectivity. Phase shaping may be employed using asymmetric biphasic waveforms or interphase intervals to reduce charge accumulation and manage relative activation thresholds for different fiber sizes.

In some non-contact example, a bipolar lead may be tunneled and positioned between approximately 0 mm and 4 mm from a motor branch that courses with an artery in a neurovascular bundle, without touching the nerve. The active pole may be oriented toward the nerve and conformal insulating body may limit medial current spread. During calibration, the system may increment 200 to 500 microsecond biphasic pulses at 1 to 5 hertz, until the EMG amplitude of the target muscle exceeds a defined detection threshold, establishing T_target. Stimulation may then be increased until it is verified that no activation occurs in adjacent compartments, thereby defining T_OT. Chronic therapy may be delivered at approximately 1-1.1 times T_target, with guard electrodes to preserve selectivity, while the controller adjusts amplitude or pulse width as impedance changes during healing so that charge per phase at the nerve remains consistent.

In another non-contact example, a small paddle with two active contacts may be placed 1 to 3 millimeters from a distal sensory branch, and the subject may report paresthesia localization during calibration. A somatotopic overlap score may be computed and T_target assigned to the lowest level achieving a high localization score without extraneous territory activation. T_OT may be determined by the onset of unintended sensory territories or motor twitch. The therapy level may operate just above T_target with intermittent low frequency probe pulses to confirm stability, and the controller may redistribute amplitude between the two active electrodes if posture changes modify the field.

In a further non-contact example targeting an autonomic pelvic nerve, a percutaneously delivered lead may be positioned 3 to 6 millimeters from the branch, and sensors may detect physiological responses such as changes in sphincter tone or peristaltic activity. The Target Threshold (T_target) may correspond to the minimum charge per phase that consistently produces a measurable and therapeutically appropriate physiological response, while the Off-Target Threshold (T_OT) may correspond to the onset of undesirable systemic effects such as heart rate deviation. The system may enforce maximum charge per phase and charge density limits suitable for non-contact stimulation while maintaining efficacy near T_target At step 212, the therapeutic stimulation is applied. After determining the appropriate threshold for the target nerve, the method proceeds to deliver therapeutic stimulation according to the configured parameters. The stimulation is applied using the device coupled directly to the nerve, ensuring selective activation and minimizing unintended effects on adjacent structures.

In some embodiments, the therapy consists of biphasic current-controlled pulses delivered in bursts. Each burst lasts between 3 and 60 seconds, followed by a rest interval of approximately 0.5 to 5 minutes, creating a controlled duty cycle that balances efficacy with safety and energy efficiency. The stimulation amplitude is set above the previously determined threshold, such as contraction threshold for motor nerves, sensation threshold for sensory nerves, or physiological threshold for autonomic nerves, while remaining within the safe operating range of 0.1 mA to 10 mA. Pulse width is maintained between 150 μsec and 500 μsec, and frequency between 20 Hz and 100 Hz, as the inventors have determined these ranges advantageously promote axonal regeneration and Schwann cell activity.

Therapy sessions may include one or more pulse bursts, repeated according to a prescribed schedule. In various embodiments, the patient receives 1 to 10 sessions per day, for 1 to 7 days per week, with the total duration of each session calculated based on the number of bursts and rest intervals. The stimulation protocol may be adjusted dynamically based on patient feedback, observed physiological responses, or clinical progress. For example, amplitude may be reduced as nerve conduction improves, or increased slightly to overcome scar tissue impedance during later stages of tissue repair.

The applied stimulation initiates a cascade of regenerative processes, including upregulation of pro-regenerative genes, axonal sprouting, and remyelination by Schwann cells. Continued therapy over multiple sessions enhances these effects, supporting structural repair and functional recovery of the nerve. In addition, chronic stimulation may contribute to muscle strengthening and improved organ function, depending on the nerve type and clinical application.

By delivering controlled, selective stimulation above the relevant threshold, this step ensures that the therapeutic effect is achieved efficiently and safely, forming the core of the method for nerve repair and regeneration.

Step 214 monitors the physiological response of the patient. Following application of therapeutic stimulation, the method includes monitoring the physiological response of the target nerve to confirm effective activation and track progress toward regeneration and repair. This step ensures that stimulation remains selective, safe, and within therapeutic limits throughout the treatment period.

Monitoring may be performed immediately after initial stimulation and periodically during subsequent sessions. For motor nerves, the response is assessed by observing visible or palpable muscle contractions in the innervated region. EMG may be employed to detect electrical activity in the muscle, providing an objective measure of contraction threshold and recruitment level. For sensory nerves, monitoring involves patient feedback regarding sensation, such as tingling or pressure, without pain. In cases where the patient is sedated or unable to provide feedback, surrogate indicators such as autonomic reflexes or EMG signals may be used.

For autonomic nerves, monitoring is based on organ-specific physiological markers. Examples include changes in heart rate for vagus nerve stimulation, alterations in sphincter tone for pelvic nerves, or motility patterns for gastrointestinal nerves. These markers may be measured using standard clinical sensors or integrated monitoring systems.

In various embodiments, the system records stimulation parameters and corresponding responses to establish a feedback loop for therapy optimization. If the observed response is inadequate or inconsistent, adjustments may be made to amplitude, frequency, or burst duration within the predefined safe ranges. Conversely, if excessive activation or off-target effects are detected, stimulation intensity may be reduced or the device is repositioned to restore selectivity.

Monitoring also provides insight into long-term progress. Over multiple sessions, improvements such as stronger muscle contractions, restored sensory perception, or normalized autonomic function indicate successful regeneration and remyelination. These observations guide decisions regarding therapy continuation, modification, or termination, ensuring that the method achieves its intended outcome of nerve repair and functional recovery.

At step 216, progressive adjustments may be made over the course of weeks as the therapy progresses. Thresholds may decrease over time as axonal continuity improves and remyelination restores conduction, allowing amplitude to be reduced while maintaining efficacy. Conversely, in cases of scar tissue or fibrosis, thresholds may increase, requiring conservative upward adjustments. Illustrative embodiments enable clinicians or automated protocols to modify amplitude, train duration, or train count within the defined ranges to sustain therapeutic effect without exceeding safety limits.

Effectiveness is validated through objective and/or subjective outcomes. Objective measures, for the urinary incontinence example, include urethral closure pressure, leak point pressure, voiding efficiency, fecal continence scores, and organ-specific physiological metrics for autonomic targets. Subjective measures include patient-reported improvements in urgency, pain, or functional performance. These outcomes are monitored periodically and used to refine stimulation parameters, ensuring that therapy remains aligned with biological progress and patient comfort.

After initial monitoring confirms effective stimulation, the method includes continuing therapy according to the prescribed schedule and adjusting parameters as needed to optimize outcomes. This step ensures that the treatment remains effective throughout the nerve repair process, which may involve regeneration, remyelination, and functional recovery.

In one embodiment, therapy is delivered over multiple sessions, typically ranging from 1 to 10 sessions per day and 1 to 7 days per week, depending on the severity of the injury and clinical objectives. The stimulation parameters, such as amplitude, frequency, and burst duration, may be modified dynamically based on patient feedback, physiological markers, or observed progress. For example, amplitude may be reduced as nerve conduction improves to maintain stimulation above threshold without causing discomfort, or increased slightly to overcome impedance caused by scar tissue during later stages of repair.

Adjustments may also account for changes in nerve physiology over time. As regeneration progresses and remyelination occurs, the nerve's excitability and conduction properties may shift, requiring recalibration of stimulation intensity or duty cycle. In various embodiments, the system employs a feedback loop that records responses and automatically recommends parameter adjustments to maintain optimal therapeutic effect (e.g., to maintain the stimulation as threshold).

In various embodiments, as therapy continues, nerve excitability and conduction properties may shift due to biological changes such as regeneration, remyelination, or scar tissue formation. These changes can alter activation thresholds in either direction, e.g., improved conduction may require a lower amplitude, while increased impedance from fibrosis may require a higher amplitude. Because these trends cannot be fully predicted, in various embodiments the process loops back to Step 214 at defined intervals or upon detection of threshold drift. This iterative process ensures that stimulation remains at or just above the functional threshold, preserving therapeutic efficacy while minimizing discomfort and energy burden.

In various embodiments, the method includes dynamically adjusting stimulation parameters during the course of therapy to maintain efficacy and patient comfort while promoting nerve regeneration and repair. Adjustments may be made in response to changes in nerve physiology, patient feedback, or observed clinical markers such as muscle contraction strength, sensory perception, or autonomic function.

The adjustments are performed within the predefined ranges described herein, ensuring safety and consistency with the therapeutic objectives. For example, amplitude may be increased incrementally within the range of 0.1 mA to 10 mA to overcome impedance caused by scar tissue or decreased excitability during later stages of repair. Conversely, amplitude may be reduced as nerve conduction improves to avoid overstimulation. Similarly, pulse width may be adjusted between 150 μsec and 500 μsec, and frequency between 20 Hz and 100 Hz, to optimize activation without inducing fatigue or thermal effects.

Burst duration and rest intervals may also be modified within the disclosed ranges (e.g., 3-60 seconds per burst, 0.5-5 minutes rest) to balance duty cycle and energy efficiency. The number of sessions per day and per week may be adapted according to patient tolerance and clinical progress, while remaining within the recommended limits of 1-10 sessions per day and 1-7 days per week.

In various embodiments, adjustments are guided by a feedback loop that records stimulation parameters and physiological responses, enabling clinicians or automated systems to fine-tune therapy without exceeding the disclosed limits. By constraining all modifications to the ranges specified herein, the method ensures that stimulation remains selective, safe, and effective across a variety of nerve types and injury severities.

The continuation phase may extend over multiple stimulation sessions until functional nerve repair is achieved, as indicated by restored muscle strength, sensory perception, or autonomic function. In some cases, therapy may be tapered gradually to prevent regression and allow the nerve to maintain its function without external stimulation. By incorporating adaptive control and ongoing assessment, this step ensures that the method delivers sustained benefits while minimizing risks associated with overstimulation or undertreatment. In some embodiments, tapering may include reducing stimulation intensity or frequency to a predefined maintenance level, which is then sustained for a period sufficient to preserve functional gains without inducing fatigue or dependency.

While a single stimulation session can trigger axonal regeneration by activating pro-regenerative pathways in the neuron, the inventors have observed that multiple sessions amplify and sustain the repair process. Repeated stimulation using the parameters described herein (e.g., with a direct-contact electrode) promote not only continued axonal growth but also enhances remyelination, which restores conduction velocity and long-term nerve function. This effect is mediated by increased Schwann cell proliferation and alignment, as well as improved recruitment of supporting cells such as fibroblasts and macrophages, which contribute to tissue remodeling and vascularization around the nerve.

In addition to structural repair, multiple sessions accelerate functional recovery. Chronic stimulation improves muscle strength in motor nerve applications, leveraging physiological load (e.g., bladder weight in pelvic floor therapy) to prevent atrophy and support hypertrophy. For autonomic nerves, repeated therapy helps normalize organ-specific functions more reliably than a single session. The inventors noted that extended stimulation over days or weeks correlates with more robust histological evidence of nerve regeneration compared to shorter protocols, for example, greater urethral pressure improvements in pelvic health models.

Functional repair may be assessed by evaluating the restoration of nerve conduction and the return of physiological function associated with the target nerve. The specific indicators vary by nerve type. For example, in motor nerves, repair may be confirmed when the target muscle demonstrates consistent, voluntary or reflexive contractions without external stimulation. Objective measures include EMG showing normal or improved recruitment patterns relative to baseline, restoration of muscle strength to baseline or clinically acceptable levels, as measured by force sensors or manual muscle testing, and/or ability to perform functional tasks (e.g., maintaining continence for pelvic floor muscles). For sensory nerves, repair may be indicated by the return of normal sensation in the innervated region. Examples include patient reports of tactile, pressure, or temperature perception within normal thresholds, quantitative sensory testing confirming normalized conduction velocity and sensory thresholds. For autonomic nerves repair may be demonstrated by normalization of organ-specific physiological functions. Examples include stable heart rate variability for vagus nerve stimulation, restoration of sphincter tone and reflexes for pelvic autonomic nerves, and normal gastrointestinal motility or bladder emptying patterns.

In various embodiments, functional recovery may also be supported by histological evidence of axonal regeneration and remyelination, such as increased Schwann cell density and restored myelin sheath thickness. Imaging modalities (e.g., ultrasound or MRI neurography) may further confirm structural continuity of the nerve.

In various embodiments, successful nerve repair may produce measurable improvements in physiological function and patient quality of life. In the context of pelvic nerve injury, restoration of neural signaling can enhance continence control in conditions such as urinary incontinence and fecal incontinence. For urinary incontinence, recovery may be evaluated through objective urodynamic measurements including maximum urethral closure pressure (MUCP), urethral pressure profile (UPP), voiding efficiency, bladder capacity, post-void residual (PVR), leak point pressure (LPP), and detrusor overactivity (DO), each of which reflects changes in sphincter performance, bladder emptying, and resistance to involuntary leakage. These measurements may be complemented by clinical assessments such as pad weight testing, cough stress tests, and voiding diaries that document frequency, urgency, and leakage events. In some embodiments, patient-reported outcome measures including the Patient Global Impression of Improvement (PGI-I), Incontinence Quality of Life (I-QOL), and validated questionnaires such as ICIQ-UI SF and UDI-6 may be used to capture subjective improvements in day-to-day function.

Similar evaluation principles may be applied to fecal incontinence, where functional recovery may be assessed through anorectal manometry, sphincter pressure profiles, and patient diaries tracking bowel control and urgency episodes. Improvements in these measurements may indicate enhanced neuromuscular coordination and restored continence. While absolute performance gains can vary depending on the severity of injury and the biological model, the combined use of objective urodynamic metrics and subjective patient feedback provides a comprehensive framework for characterizing therapeutic benefit.

Following nerve repair associated with urinary continence pathways, certain trends may be anticipated. MUCP values may increase, indicating improved sphincter strength; bladder capacity and voiding efficiency may increase; PVR volumes may decline, suggesting improved detrusor-sphincter coordination; and LPP values may rise, indicating reduced susceptibility to stress-induced leakage. These physiological changes may correspond with decreases in pad weight during standardized testing and improved scores on PROMs such as PGI-I, I-QOL, and ICIQ instruments. Collectively, such improvements are consistent with restoration of neuromuscular control and improved functional outcomes in accordance with illustrative embodiments.

In other embodiments involving motor nerve repair, expected recovery metrics may include restoration of voluntary muscle contraction as evidenced by electromyographic measurements showing improved motor unit recruitment, increased strength and endurance measured through dynamometry, improved gait parameters, and reductions in muscle atrophy as reflected in imaging studies. For sensory nerve repair, outcomes may include reductions in detection thresholds for vibration and light touch, decreases in neuropathic pain scores, and improvements in functional sensory testing such as two-point discrimination and proprioception. These assessments provide a broad framework for evaluating recovery across different nerve types and anatomical targets.

The method may define recovery as achieving these functional benchmarks consistently over a predetermined observation period, after which stimulation therapy can be tapered or discontinued. This ensures that the nerve has regained sufficient intrinsic activity to maintain function without external assistance.

The process then comes to an end.

It should be apparent to one skilled in the art that present method and device offers several significant advantages for nerve repair. Conventional approaches typically require prolonged stimulation sessions, such as one hour at 20 Hz, to achieve regenerative effects. In contrast, the disclosed method achieves comparable or superior outcomes using ultra-short pulse trains lasting less than one minute, dramatically reducing intraoperative time and enabling practical adoption during surgical procedures. The inventors were surprised by this reduction because prior embodiments use extended stimulation times.

Various embodiments also advantageously provide for dynamic adjustment of stimulation parameters within predefined safe ranges using threshold-based modulation for regenerative therapy. Unlike static protocols, the present method incorporates adaptive control of amplitude, frequency, and duty cycle based on real-time feedback, such as contraction threshold, sensation threshold, or physiological markers. These adjustments remain constrained within disclosed ranges, ensuring selectivity and safety while accommodating changes in nerve physiology during recovery.

The method also introduces a multi-modal threshold system tailored to different nerve types: contraction threshold for motor nerves, sensation threshold for sensory nerves, and physiological threshold for autonomic nerves. Other embodiments apply uniform stimulation criteria without accounting for nerve-specific functional markers. This differentiation enables precise targeting across diverse nerve classes, including autonomic nerves, which are rarely addressed in regenerative protocols.

Further, illustrative embodiments provide mechanical and electrical selectivity through direct epineurial coupling with insulation, minimizing volume conduction and off-target activation. Some other embodiments rely on cuff electrodes or transcutaneous stimulation, which undesirably lack this level of precision. The combination of mechanical selectivity and parameters synergistically provides nerve repair.

Furthermore, illustrative embodiments are advantageously applicable across multiple nerve injury grades, from demyelination to partial transection, and even severe cases requiring bridging.

Figure 3A:
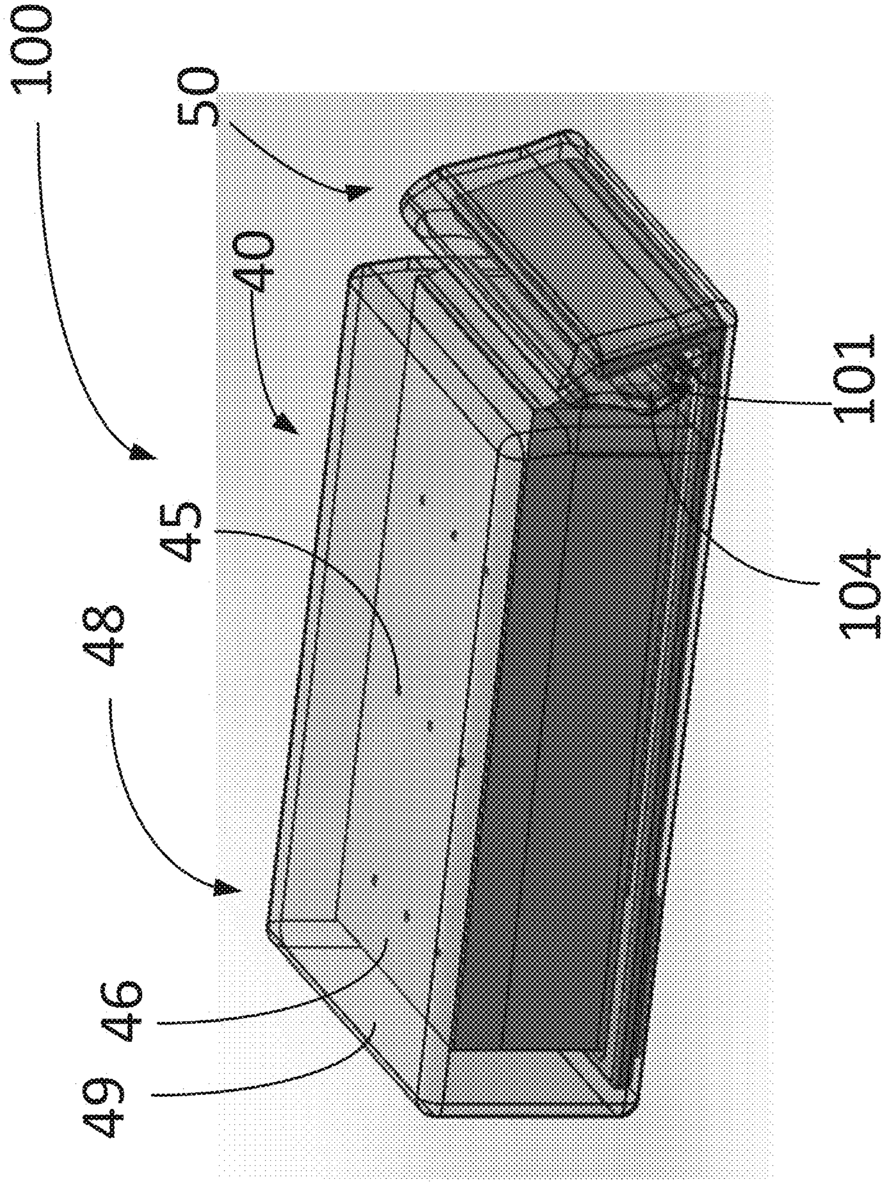

FIG. 3A schematically shows a neuromodulation device 100 configured in accordance with illustrative embodiments. To that end, the neuromodulation device 100 has a main body 40 coupled with a movable target retention portion 50 (also referred to as a movable arm or movable jaw 50). The arm 50 may be hingedly coupled with the main body 40 (e.g., such that the arm 50 pivots relative to the main body 40).

In various embodiments, the main body 40 may include a housing 48. The housing 48 may also encapsulate at least a portion of the movable arm 50. To that end, the housing 48 may be formed from a resilient or deformable material. The main body 40 and the movable arm 50 (or the portion of the housing 48 surrounding the movable arm 50 and the main body 40) may define a chamber 101 configured to receive a nerve 200 and a channel 102 leading to the chamber 101. In some embodiments, the chamber 101 may be defined by one or more arms 50. The chamber 101 includes at least one electrode 104 to stimulate the nerve 200.

The housing 48 encapsulates a package 46 of the main body 40. The housing 48 includes a buffer layer 49. As known by those of skill in the art, the package 46 encapsulates electronics and semiconductor material within. For example, the package 46 may include different types of circuitry, including stimulator(s), sensor(s), communication(s), and/or power circuitry. In various embodiments, the package 46 may be formed from a substantially rigid material, such as titanium, stainless steel, glass, ceramic, alumina, zirconium, plastic, and/or other generally acceptable hermetic package material. In various embodiments, the electronic package and the nerve/attachment electrode are unitary. In various embodiments, instead of a feedthrough pin extending from the hermetically sealed housing that is welded to the electrode, the feedthrough pin forms the electrode. In such embodiments, the electrode is unwelded (i.e., has no welded joints connecting it to the feedthrough pin). Instead, the feedthrough pin forms the electrode. When the feedthrough pin is embedded in the movable arm (e.g., silicone) it operates as a reinforcement for the deflecting arm.

The package 46 forms a hermetic seal around the internal electronic circuitry. The electronic circuitry may be loaded into the hermetic enclosure 46 and sealed in an inert oxygen and water-limited environment. After the hermetic seal is formed, two advantages are provided. First, the hermetic seal ensures that no additional liquid is introduced into the electronic package 46, potentially causing electrical failure. Second, the hermetic seal ensures that the non-biocompatible materials from which the internal electronics are formed do not leach into the body.

The package 46 may be formed from a glass or ceramic material, which provide reduced interference to radio frequencies used for wireless power and wireless communication relative to other commonly used package 46 materials. The package 46 (also referred to as the hermetic enclosure 46) may be formed from glass wafers directly bonded to one another. Alternatively, the package 46 may be formed from zirconia ceramic with brazed feedthroughs. In various embodiments, the package 46 may be sealed using laser welding titanium surfaces brazed to the zirconia.

The buffer layer 49 covers the package 46 and provides a second biocompatible layer and suitable soft surface within the human body and continuity to portion contacting the nerve 200. As mentioned previously, the arm 50 may include the overmolded housing 48 formed of a softer material (e.g., durometer 30-50 Shore A).

The buffer layer 49 may be formed from a material configured to conform within its resting position in the body. Although the arm 50 and the package 46 may be encapsulated by the housing 48, the buffer layer 49 does not cover the electrodes 104. Accordingly, the housing 48 may have openings for the electrodes 104 and/or an EMG 42. Additionally, vias 45 may be formed through the housing. In various embodiments, the buffer layer 49 can encapsulate between about 20% and about 99% of the device. Vias 45 may extend through the package 46 and/or the housing 48 (including buffer layer 49). Electrodes 104 and other external electrical connections may be connected to the metalized vias 45. The metalized vias may be formed using platinum feedthrough wires, among other things. The package 46 and the buffer layer 49 may be joined using RTV biocompatible silicone.

In FIG. 3A, the arm 50 is depicted in a closed position or a substantially closed position (collectively referred to as the closed position of the device), in which the size of the channel 102 is sufficiently small so that the nerve 200 cannot pass through the channel 102. The arm is movable from the closed position to an open position in which the size of the channel 102 is sufficiently large so that the nerve 200 can pass through the channel 102. In some embodiments, the open position is sufficiently large such that the nerve 200 can be pass through the channel with a reduction in diameter of less than about 30% to about 50% (e.g., by stretching and/or squeezing the nerve through the channel). Various embodiments may be configured to receive a variety of nerve sizes, as discussed further below. In various embodiments, the arm 50 may be biased (e.g., by the use of a biased interior member 51) towards the closed position. A medical practitioner may transition the arm 50 to the open position by applying a force to the arm 50 (e.g., by pulling on a grippable extension 52) or by pressing the arm 50 with the nerve 200 itself. The nerve 200 may then pass through the channel 102 into or out of the chamber 101.

FIG. 3B illustrates a top-down view of an implantable nerve stimulation device 100 in accordance with illustrative embodiments. The device 100 includes a nerve engagement portion 50 positioned adjacent to, and coupled with, the target nerve 200. A hermetic enclosure 46 is located beneath the nerve engagement portion 50 and houses a pulse generator or other stimulation circuitry. One or more feedthrough conductors extend through the hermetic enclosure 46 to provide electrical coupling between the internal circuitry and the external stimulation electrodes. These feedthrough conductors may function as the stimulation electrodes that deliver electrical pulses directly to the nerve when the device is in the engaged position.

FIG. 3C presents a side view (upper image) and a partially transparent side view (lower image) of the nerve stimulation device shown in FIG. 3B. The side view illustrates the relative placement of the nerve engagement portion 50, lid or lid-through structure, and the hermetic enclosure 46. The feedthrough conductors extend from the internal circuitry through the hermetic enclosure to form external stimulation electrodes positioned adjacent to the nerve for direct nerve stimulation.

The transparent version of the side view reveals internal components of the device, including a printed circuit board assembly (PCBA), an internal battery, and a transmit and recharge coil configured to receive inductive energy from an external source. The coil and internal electronics may be supported by an internal nest or structural frame. The combined arrangement enables the device to generate and deliver controlled stimulation pulses to the nerve while maintaining hermetic isolation of the internal electronics.

Figure 3D:
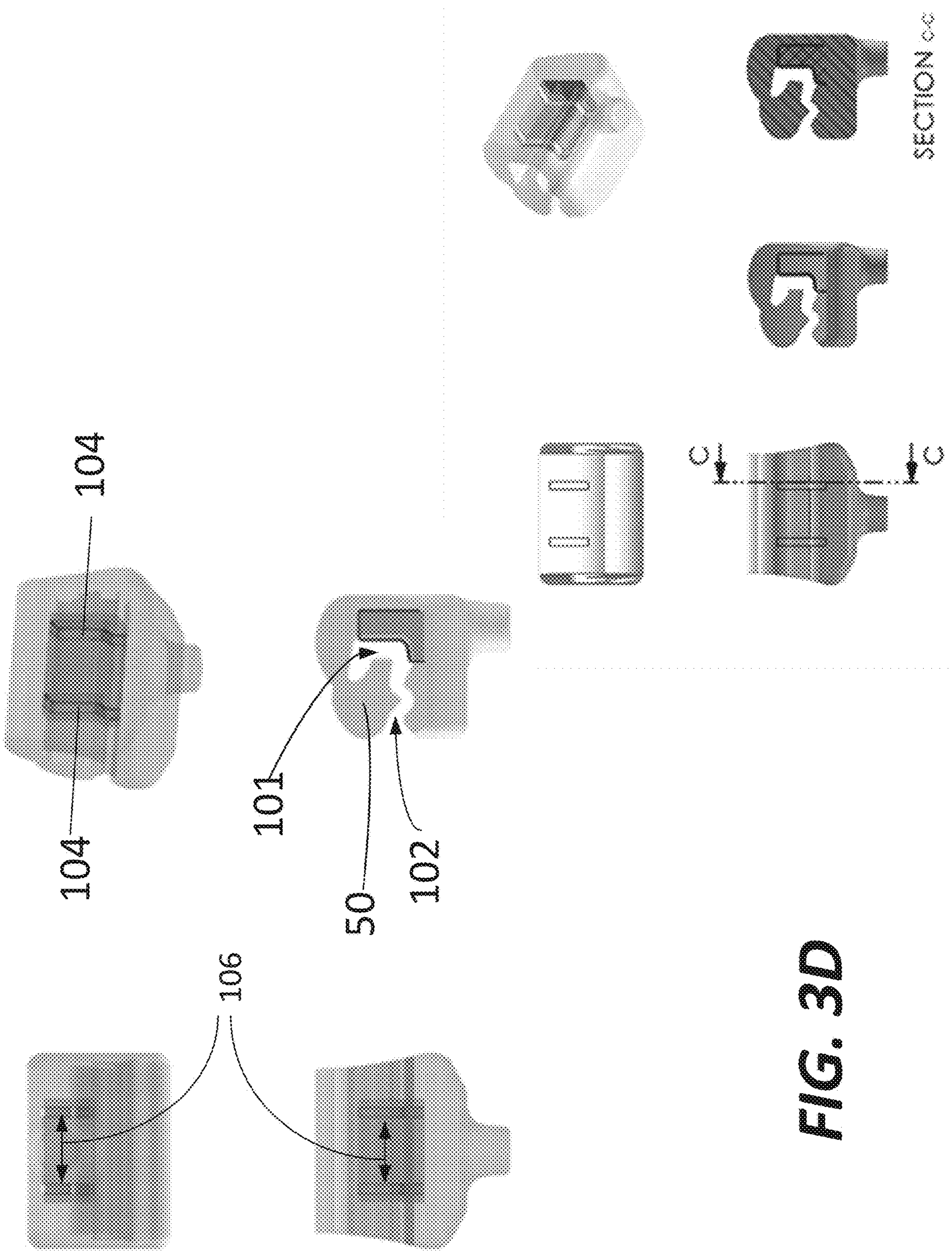

FIG. 3D illustrates an embodiment of a nerve-engagement structure configured to deliver stimulation directly to a target nerve. As shown, the nerve-engagement portion 50 (also referred to as the target engagement portion) includes a pair of electrodes 104 positioned along an interior surface of a clip-like or cuff-like structure sized to partially surround or engage the nerve. The electrodes are supported by, and electrically isolated within, the body of the engagement structure. In some embodiments, the electrodes are formed as conductive feedthrough structures extending from a hermetic electronics enclosure (not shown in this view), thereby providing both structural anchoring and electrical continuity to the pulse-generation circuitry.

The two electrodes are offset from one another along the inner profile of the engagement portion, enabling delivery of stimulation using an active-return configuration. In such embodiments, a first electrode is driven with a stimulation current while the second electrode functions as an active return path, allowing current to flow between the two electrodes through the adjacent nerve tissue. This configuration differs from monopolar or case-return arrangements in which the return electrode is located remotely on the device housing or elsewhere in the body. The dual-electrode active-return configuration may promote more confined current pathways, greater selectivity, and improved control of charge balance during biphasic stimulation.

The cross-sectional views further illustrate the geometry of the engagement portion, including the placement of the electrodes relative to the surface intended to contact or closely approximate the nerve. The distance between the electrodes may be selected based on mechanical constraints and electrical performance considerations. In some embodiments, smaller electrode distance may be achievable relative to conventional nerve-cuff electrodes, allowing the electrodes to be placed at distances suitable for small peripheral nerves or anatomically constrained sites. The electrode spacing may influence the voltage required to depolarize the nerve, the distribution of the induced electric field, and the efficiency with which current is delivered to the tissue.

In various embodiments, the spacing between the two electrodes of the nerve-engagement portion is selected to optimize stimulation efficiency for the specific nerve geometry and anatomical constraints. Empirical testing performed on representative nerve segments demonstrated that larger electrode spacing generally reduced the current required to achieve a given neural response, thereby lowering overall energy consumption and reducing unnecessary current dispersion into surrounding tissues. Conversely, when electrodes are spaced too closely, a portion of the applied current may traverse a short path between the electrodes without penetrating sufficiently into the nerve to produce depolarization, resulting in reduced stimulation efficiency. The embodiments described herein therefore utilize electrode spacing that is smaller than the spacing typically found in commercially available nerve-cuff electrodes, yet sufficiently large to avoid short-circuit current paths. For example, in some tests, the optimized spacing was at least approximately 0.5 mm smaller than the next closest spacing found in standard cuff designs, while still achieving efficient activation of the target nerve with lower current thresholds. This spacing configuration may provide improved selectivity, reduced energy requirements, and enhanced suitability for small or anatomically constrained nerves.

In various embodiments, the nerve-engagement structure includes a pair of electrodes configured with an interelectrode distance 106 of approximately 3 mm, within a range of 2.5 mm to 3.5 mm, to optimize stimulation efficiency while supporting device miniaturization. Empirical testing demonstrated that this spacing provided the lowest stimulation threshold and most consistent performance among tested configurations, thereby reducing energy consumption and improving therapeutic reliability. The selected spacing also accommodates anatomical constraints of the target nerve, such as the human perineal nerve, which exhibits an average diameter of approximately 1.8±0.6 mm, significantly smaller than other clinically targeted nerves (e.g., vagus or sciatic nerves).

The electrodes may further include a width of approximately 0.5 mm, selected to increase the effective neural interfacing area, reduce impedance, and enhance charge injection capacity. Comparative testing indicated that wider electrodes reduced stimulation thresholds relative to narrower electrodes, while maintaining safe charge density levels.

Safety considerations were validated through charge injection analysis. For example, at a maximum stimulation current of 2 mA and a pulse width of 250 μs, the calculated surface charge density for a 0.5 mm wide electrode was approximately 15.38 $\mu C \cdot cm^{-2} \cdot ph^{-1}$, which is well below the reversible charge injection capacity of platinum-iridium alloys (50-150 $\mu C \cdot cm^{-2} \cdot ph^{-1}$). Further analysis using Shannon's equation yielded a safety factor (k) of 0.886 under worst-case conditions, significantly below the threshold ($k \geq 1.85$) associated with tissue damage. In contrast, electrodes with a width of 0.25 mm approached this safety limit ($k \neq 1.81$), reinforcing the preference for the 0.5 mm configuration.

The combined selection of 3 mm interelectrode spacing and 0.5 mm electrode width enables efficient nerve fiber recruitment, reduced stimulation thresholds, and compliance with chronic stimulation safety standards, while maintaining an overall device width of approximately 6 mm, well within the anatomical implantation limit of 10 mm. Various embodiments have advantages over conventional nerve-cuff electrodes, which typically employ larger interelectrode distances 106 and are unsuitable for small or anatomically constrained nerves.

In various embodiments, the interelectrode distance 106 is selected within 2.5-3.5 mm, preferably about 3.0 mm, based on empirical testing demonstrating lowest stimulation thresholds and reduced variance compared with 2 mm, 4 mm, and 5 mm configurations in a nerve model of comparable diameter. Electrode width is selected as about 0.5 mm to reduce impedance and increase charge injection capacity, enabling per-phase charge density of ≤15.38 $\mu C \cdot cm^{-2} \cdot ph^{-1}$ at 2 mA and 250 μs, below reported Pt—Ir reversible CIC limits. Under these conditions, Shannon k is ≤0.886, below injury thresholds ($k \geq 1.85$). Comparative embodiments with 0.25 mm width approach the safety limit ($k \approx 1.81$) at similar currents, supporting the selection of 0.5 mm width for chronic use.

The total device width can be ≤6 mm, including ≥0.5-1.0 mm of outboard insulation on each side of the electrodes to mitigate direct current leakage to surrounding tissue. In various embodiments, an anatomical access constraint of ≤10 mm governs the device envelope for implantation at the perineal nerve.

Figure 3E:
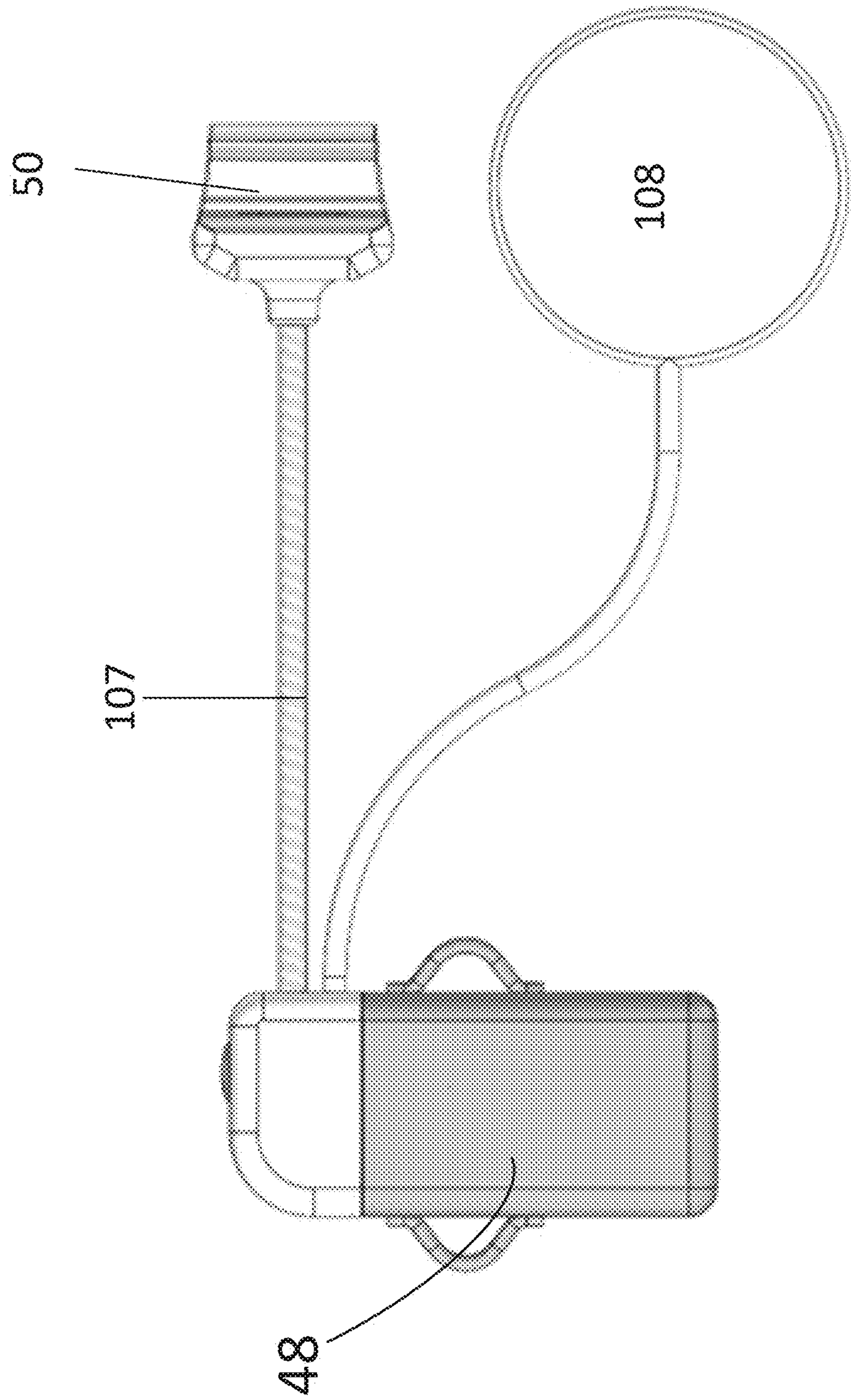

FIG. 3E illustrates an embodiment of an implantable neuromodulation system in which a pulse-generation module is contained within a hermetic enclosure (e.g., within housing 48) implanted subcutaneously. The hermetic enclosure houses the stimulation electronics, power management circuitry, and an internal rechargeable power source. The enclosure may include one or more mounting structures or suture tabs for fixation within the body.

A lead 107 extends from the hermetic enclosure to a distal nerve-engagement component 50, shown at the right side of the figure. The nerve-engagement component 50 may take the form of a cuff, clip, or similar structure configured to partially surround the nerve and maintain stable contact between the nerve and the stimulation electrodes. In various embodiments, two or more electrodes 104 are embedded within the nerve-engagement component 50 to deliver stimulation pulses to the target nerve in a bipolar, multipolar, or active-return configuration.

Also connected to the hermetic enclosure is an inductive recharge coil 108, shown at the lower right of the figure. The recharge coil 108 is configured to receive transcutaneous energy from an external transmitter and to relay that energy to the internal battery or power-storage circuitry. The recharge coil may be positioned at a location favorable for inductive coupling, such as a shallow subcutaneous pocket, while remaining electrically connected to the primary electronics via a short lead.

The configuration shown in FIG. 3E illustrates a system architecture in which the stimulation module, nerve-engagement structure, and recharge subsystem are physically distinct but functionally integrated components designed to operate together as an implantable therapeutic device.

Figure 3F:
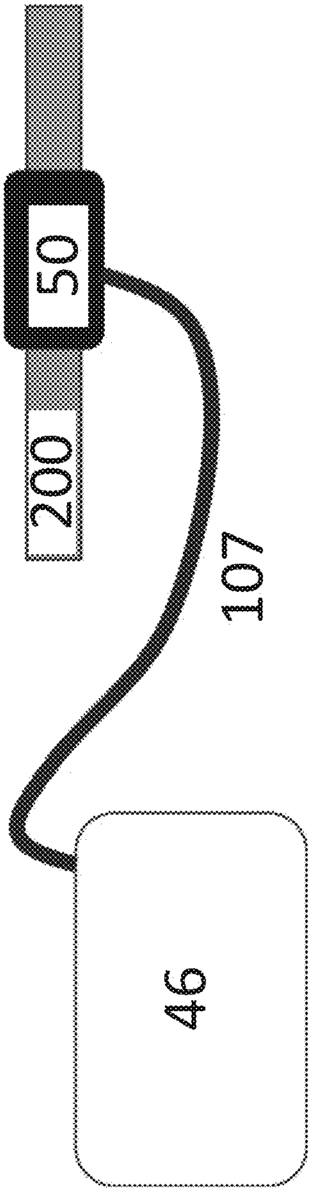

FIG. 3F illustrates an embodiment of a stimulation system in which an implantable pulse generator (IPG) is housed within a hermetic enclosure 46 containing the pulse-generation circuitry, power source, and associated electronics. The IPG 46 is connected to a lead 107 that extends from the enclosure to a distal nerve interface 50. The nerve interface may take the form of, among other things, a cuff electrode, a clip-type electrode, or another structure adapted to engage the nerve and deliver stimulation pulses.

In this configuration, the stimulation pulses generated within the hermetic enclosure are conducted along the lead to the distal electrode assembly, where they are applied directly to the target nerve. This type of architecture represents a lead-based neuromodulation system in which the pulse-generation module and the nerve-engagement module are physically separated but electrically connected via the implanted lead.

Figure 3G:
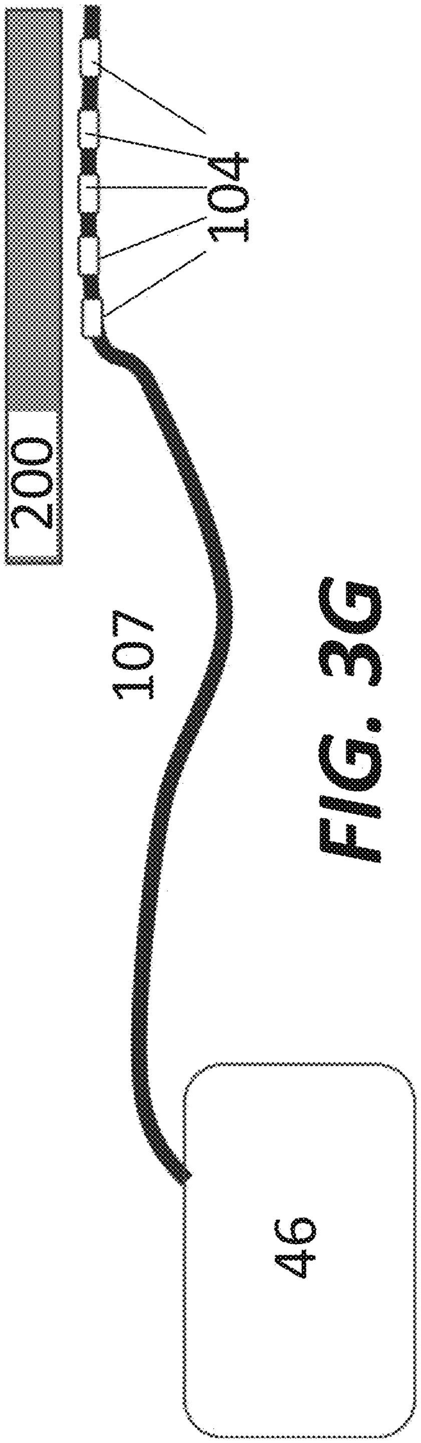

FIG. 3G illustrates an embodiment in which an implantable pulse generator housed within a hermetic enclosure 46 is connected to a distal lead that carries an electrode array positioned adjacent to the target nerve. The electrode array includes multiple discrete electrode contacts 104 distributed along a portion of the lead near the nerve 200. Each of the electrode contacts 104 may be individually addressable, allowing stimulation to be delivered between any selected pair or combination of contacts.

In operation, stimulation pulses generated by the pulse generator are conducted through the lead to one or more of the electrodes 104. By selecting different electrode pairs, channels, or spatial configurations, the device may deliver stimulation to the nerve in a variety of patterns. This configuration enables current steering, in which the electric field is shaped or directed by activating different electrode combinations to target specific regions of the nerve. The electrode array may therefore be programmed, reconfigured, or adaptively adjusted to identify or maintain stimulation pathways that produce desired physiological responses.

Figure 3I:
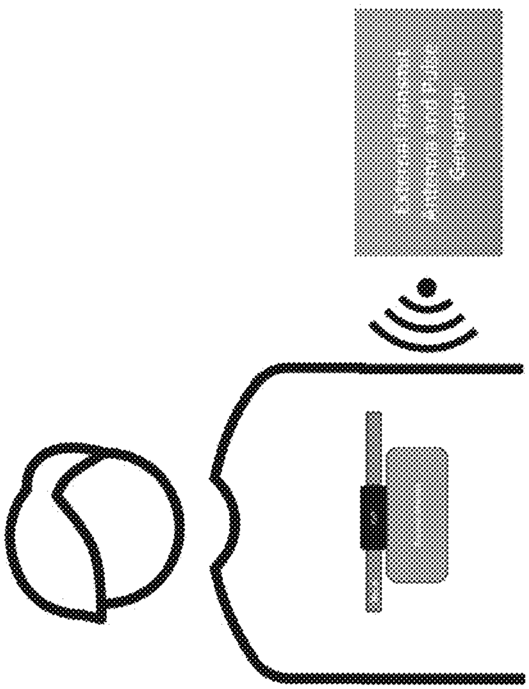
Figure 3K:
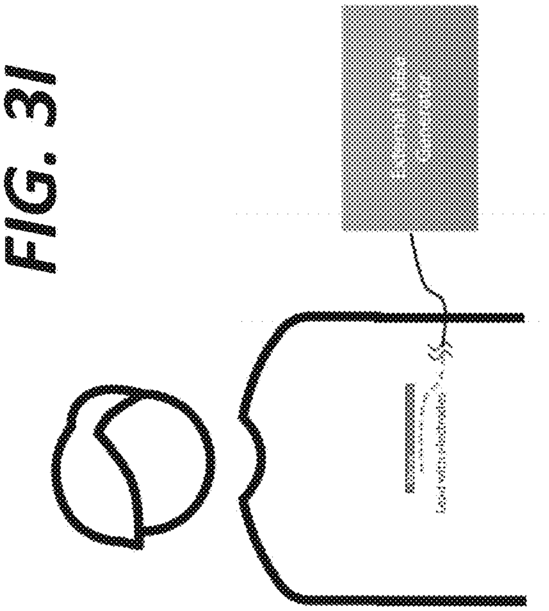
Figure 3H:
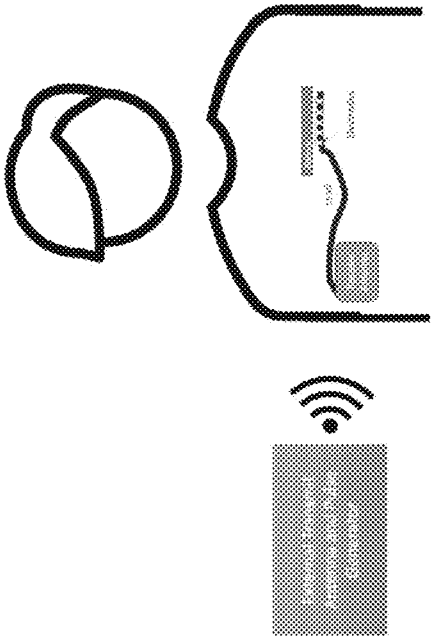

FIG. 3H illustrates an embodiment of a wirelessly powered neuromodulation system in which the stimulation signals and operating power are generated externally and transmitted transcutaneously to an implanted receiver. In this embodiment, an external transmit antenna and pulse generator are positioned outside the patient's body and configured to deliver power and stimulation control signals through wireless coupling, such as near-field inductive, RF, or magnetic-field transmission.

Inside the body, an implanted receive antenna is electrically connected to a lead that terminates at a distal electrode assembly positioned adjacent to the target nerve. The implanted receive antenna converts the externally transmitted energy into electrical power suitable for driving the electrodes and delivering stimulation pulses to the nerve. Because the implant does not contain an internal battery or onboard pulse-generation circuitry, the implanted components may be made smaller and simpler, with reduced hermetic volume relative to self-powered implants.

FIG. 3I illustrates an embodiment of a wirelessly powered, leadless nerve-stimulation device in which the stimulation electrodes and wireless receiver are integrated into a compact implant positioned directly at the target nerve. As shown, a nerve-engagement structure, such as a clip, clamp, or cuff is configured to secure the device around or adjacent to the nerve. The nerve-engagement structure houses, or is mechanically coupled to, an implanted receive antenna that captures power and control signals transmitted from an external transmit antenna and pulse generator located outside the patient's body.

In this embodiment, the implant does not include a lead or an internal battery. Instead, all stimulation energy is delivered transcutaneously from the external unit. The receive antenna converts the transmitted energy into electrical signals that are routed directly to the stimulation electrodes integrated within the nerve-engagement structure. This architecture enables a highly miniaturized implant located entirely at the nerve site while shifting pulse-generation functions to the external device.

Figure 3J:
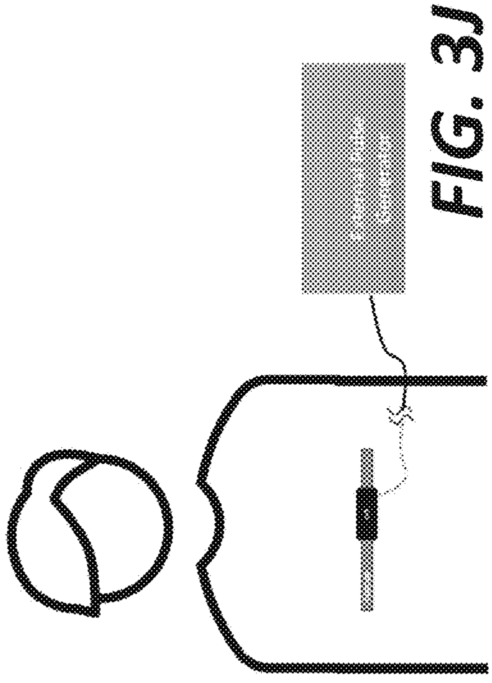

FIG. 3J illustrates an embodiment in which stimulation energy and control signals are provided by an external pulse generator, and the implant includes only a minimal nerve-engagement structure with a percutaneous connection. In this configuration, a cuff, clip, or similar nerve-engaging element is positioned directly on the target nerve. A percutaneous wire extends from the implanted nerve-engagement structure to the external pulse generator, allowing stimulation to be delivered directly from the external unit without requiring an implanted battery, wireless receiver, or internal electronics.

This embodiment may be used in circumstances where short-duration stimulation is desired, such as during acute treatment intervals, perioperative interventions, or limited-time regenerative protocols. Because the active electronics and power source remain external to the body, the implanted component can be small, simple, and easily removed. In some embodiments, the nerve-engagement structure may be biodegradable or may be removed following completion of the stimulation period.

The configuration shown in FIG. 3J therefore represents a temporary or percutaneous stimulation architecture in which the external device generates the stimulation waveform, and the implanted component functions primarily as a passive electrode interface that can be deployed for hours, days, or weeks to support nerve-repair or neuromodulation therapies.

FIG. 3K illustrates another embodiment of a temporary or short-duration nerve-stimulation system in which an external pulse generator delivers stimulation through a percutaneous lead connected to a small implanted electrode assembly positioned at the nerve. In this configuration, the distal portion of the lead carries one or more electrodes configured to contact or closely approximate the nerve surface. Unlike fully implanted systems, the proximal end of the lead exits the body and connects directly to the external pulse generator, which provides all stimulation energy and waveform control.

This embodiment allows the implanted components to remain minimal and easily removable. In some variations, the percutaneous lead may be designed with features that facilitate simplified extraction following completion of the stimulation period, such as smooth-profile insulation, flexible construction, or reduced anchoring structures. As in other disclosed embodiments, stimulation may be delivered for hours, days, or weeks to support nerve-repair or regeneration protocols without requiring a permanent implant or an internal power source.

In various embodiments, the electrode assembly at the nerve may incorporate a receive antenna or conductive structure to support hybrid modes of operation, although the primary stimulation energy in the configuration shown in FIG. 3K is provided directly through the percutaneous lead from the external pulse generator.

Figure 3L:
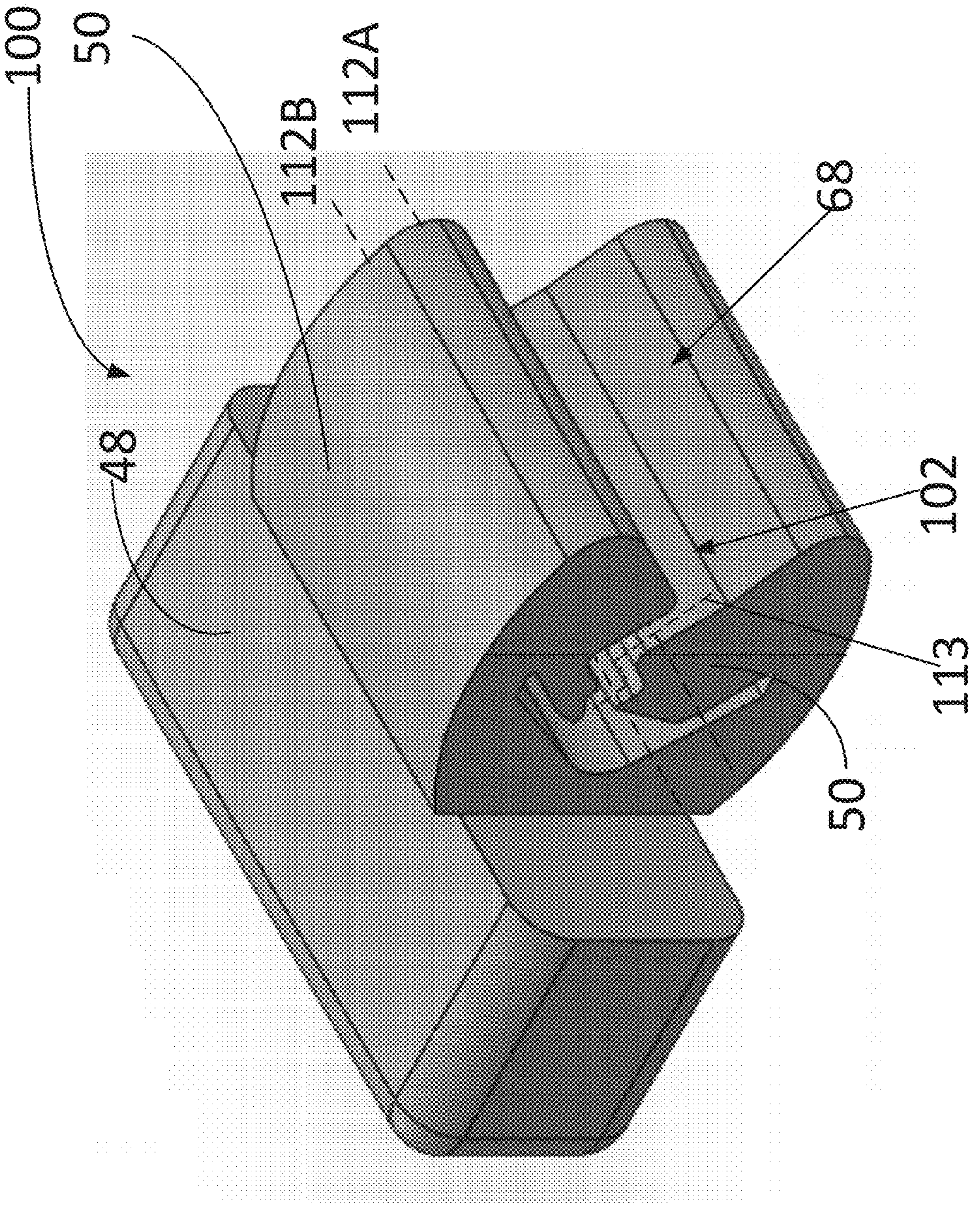

FIG. 3L schematically shows a perspective view of alternative embodiments of the device 100 (with details of the chamber 101, such as the electrode 104 omitted). The channel 102 has a particular travel path 113 (also referred to as a central axis 113) for the nerve 200. For example, as shown in FIG. 3L, the central axis 113 is non-linear. The central axis 113 may be defined by the arms 50.

In addition to the central axis 113, the device 100 has a longitudinal axis 112 that is orthogonal to the central axis 113 at any given point. During nerve implantation procedure, the nerve 200 is generally parallel to the longitudinal axis 112 as it travels along the central axis 113. Two different longitudinal axes 112A and 112B are shown for two different points along the central axis.

Figure 3M:
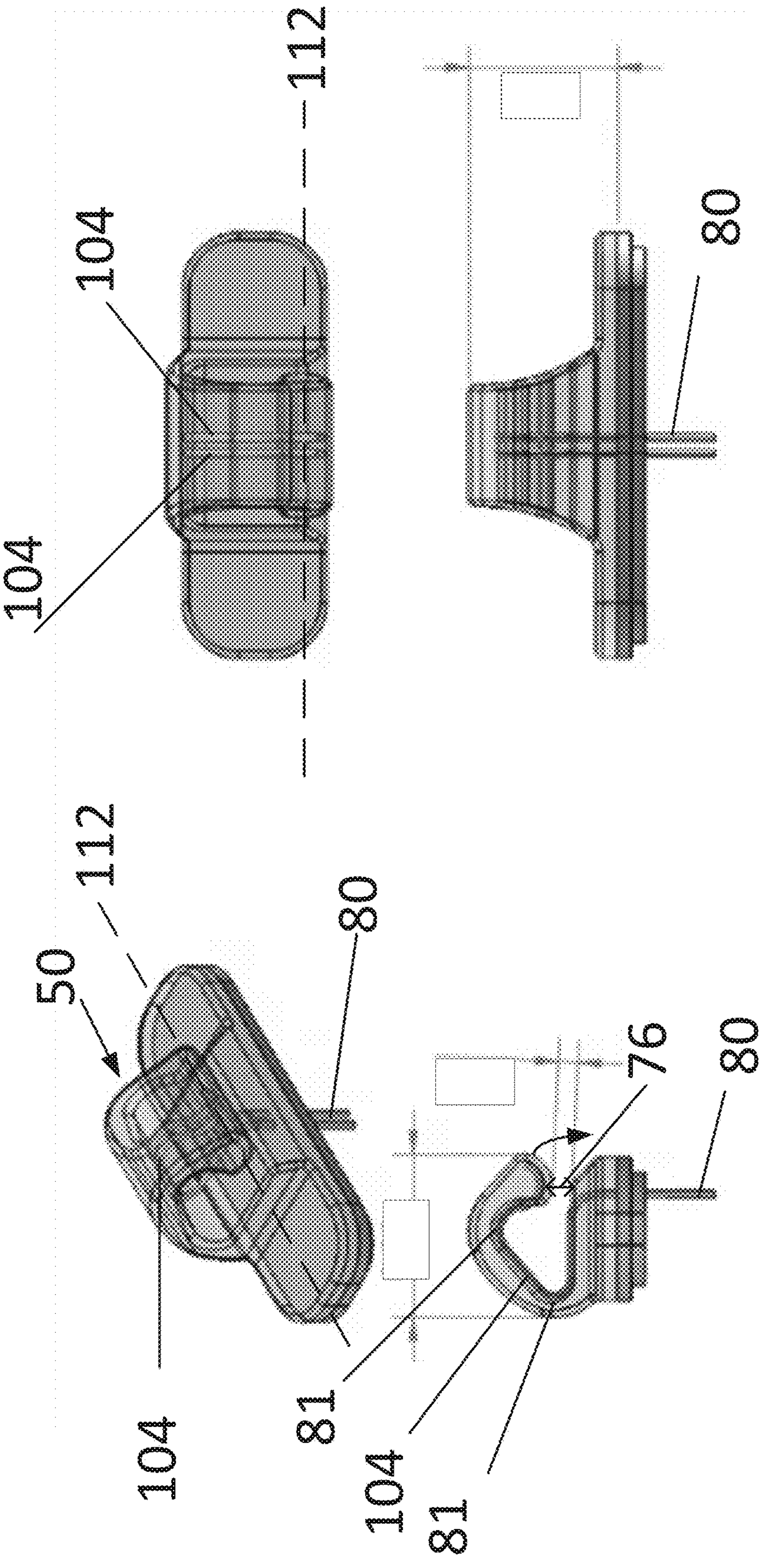

FIG. 3M schematically shows another embodiment of the neuromodulation device 100 in accordance with illustrative embodiments. FIG. 3M shows four different views of a neuromodulate device 100. The hermetically sealed main body 40 is largely omitted. However, a feedthrough conductor 80 that extends from the interior of the hermetically sealed main body 40 is shown. The feedthrough conductor 80 extends through the package 46 and the buffer layer 49. The feedthrough conductor 80 then forms the electrode 104 within the chamber 101, which is defined by the movable arm 50.

The movable arm 50 is shown biased towards a closed position. Although referred to as the "closed position," some embodiments may have the gap 76. Therefore, it is not necessary that the movable arm 50 entirely close the gap 76 in the closed position. The closed position 76 is used to refer to the position of the channel 102 when the channel is narrow to retain the nerve. As the nerve passes through the channel 102, the gap 76 increases (e.g., because the arm 50 moves and/or deforms) and the movable arm 50 transitions towards the open position. To help facilitate the opening of the channel, the movable arm 50 may include one or more bending points 81 formed from a material configured to bend, in order to accommodate the nerve 200. It should be understood that the gap 76 does not have to be fully closed to be biased towards the closed position. In a similar manner, the gap 76 does not have to be fully open to transition towards the open position.

Figure 3N:
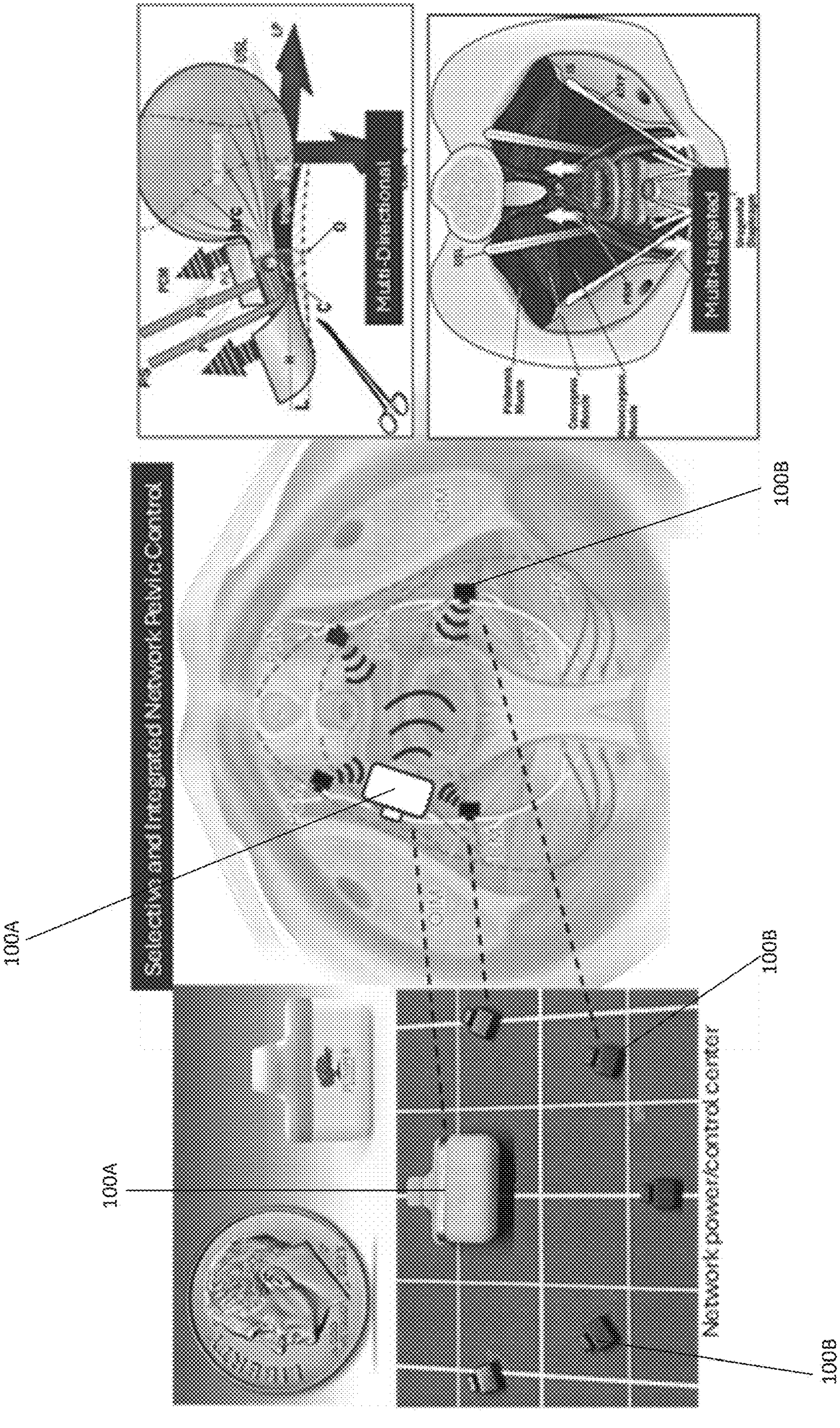
Figure 30:
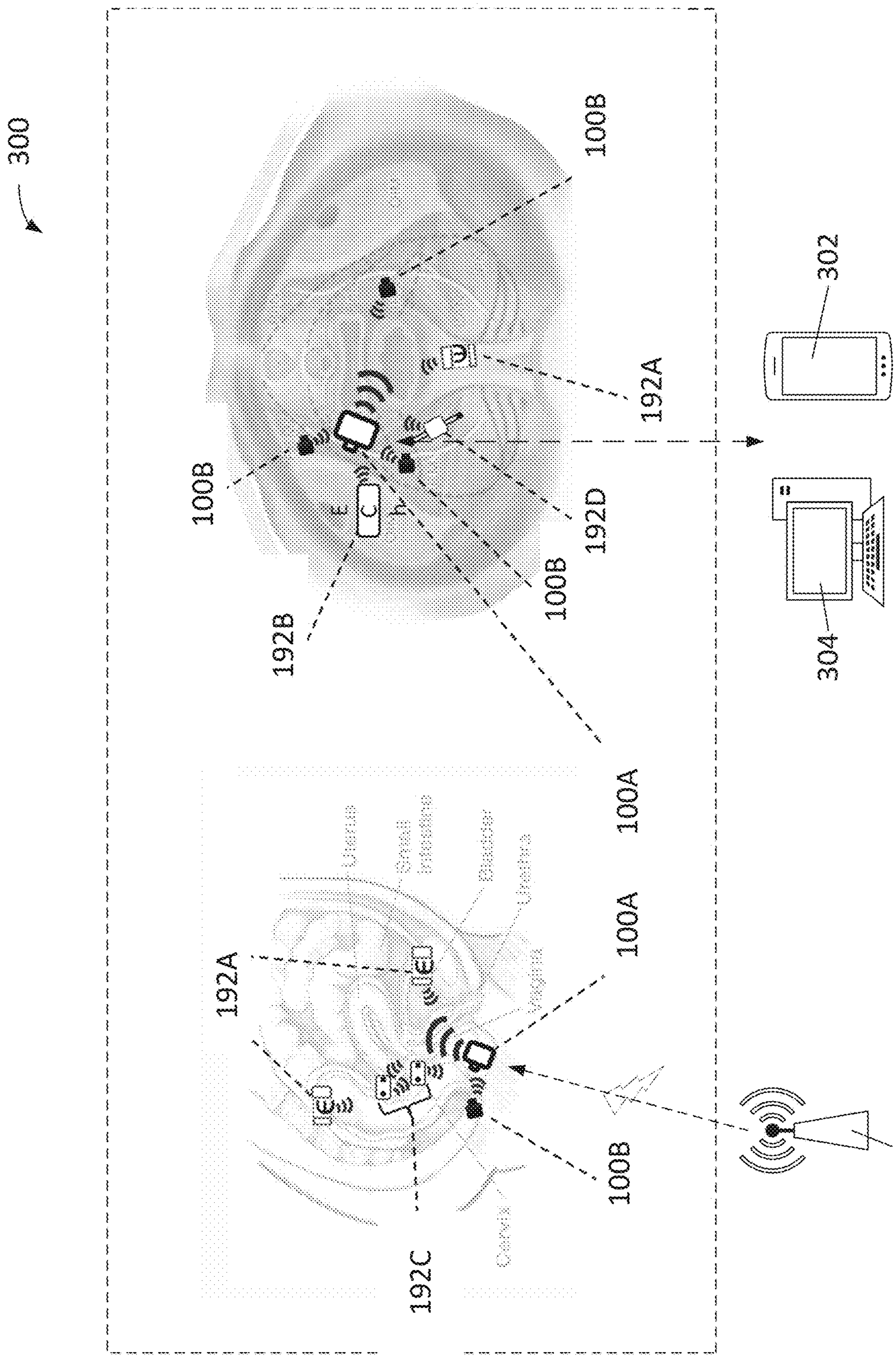

FIGS. 3N-3O schematically show a system 300 for neuromodulation in accordance with illustrative embodiments. FIG. 3O shows details of additional sensors 192 that may be separate from the neuromodulation device 100. The left side of FIG. 3O shows a sagittal plane device array example. The right side of FIG. 3O shows a pelvic floor device array example. Among other things, FIG. 3O shows:

- a primary neuromodulation device 100A. The device 100A may be coupled to the nerve using the Slide-and-Lock method to anchor the electrode and/or sensor 192 to the nerve. This device 100A may be battery operated.
- a plurality of satellite neuromodulation devices 100B. These may be miniature-devices. The device 100B may be coupled to the nerve using the Slide-and-Lock method to anchor 43 the electrode and/or sensor 192 to the nerve.

Strain sensors 192A on the bladder and rectum. A pressure membrane 73 connected to a semistretchable membrane that has two anchor 43 points as seen in the image indicates stretch. A strain sensor 192 can detect strain in ligaments, muscles, bladder wall, colon wall, or the rectum wall. The sensor 192 may be anchored 43 using one or more of barbs or sutures or adhesives.

Electrochemical sensor 192B: The sensor 192 detects local chemical related changes. The sensor 192 may be anchored 43 using one or more of barbs or sutures 44 or adhesives.

Positional Sensor 192C: relative positions of two sensors 192 may indicate relative location and movement over time. The sensor 192 may be anchored to known landmarks to evaluate relative movement of structures to evaluate pelvic floor structure relative position. The sensor 192 may be anchored using one or more of barbed protrusions or sutures 44 or adhesives.

EMG Sensor 192D: Two tethers 53 may be anchored into the muscle, using, for example barbs 43, or sutures 44.

Nerve recorders: In some embodiments of a nerve stimulation system, one nerve stimulation device 100 is used to record nerve activity to serve as input to another nerve stimulation device.

Various embodiments may include one or more of the above components (e.g., a single neuromodulation device 100 without any satellites or EMG sensors)

Illustrative embodiments use one or more miniature, self-contained and implantable, battery powered stimulators 100 (also referred to as a neuromodulation device 100). In various embodiments, this stimulator may be the stimulator described in U.S. patent application Ser. Nos. 16/185,285, 16/414,169, 18/225,129, and/or 18/225,130, each of which are incorporated herein by reference.

The stimulator directly contacts the appropriate peripheral target nerve located in the pelvis to provide direct neuromodulation, which is more precise and requires lower power than volume conduction, to achieve a desired clinical effect. The inventors have successfully tested the neuromodulation device 100 in an acute and chronic sheep model for the treatment of SUI and for the treatment of OAB. Furthermore, the inventors have successfully tested the neuromodulation device 100 in a rabbit model for FI.

In some embodiments, one or more neuromodulation devices 100, including both primary neuromodulation devices 100A and satellite neuromodulation devices 100B, may be configured to receive control signals from an external computing device 304 operated by a clinician, such as a physician programmer or a clinic-based workstation. Additionally or alternatively, therapy parameters, schedules, and feedback may be adjusted or monitored via a patient-controlled mobile device 302, such as a smartphone or tablet, through a secure wireless interface. This external control allows for convenient real-time adjustment of stimulation settings, patient-reported outcomes tracking, and longitudinal therapy optimization. Furthermore, in various embodiments, the primary neuromodulation device 100A may be configured to receive power wirelessly from an external wireless power source 306, such as a wearable inductive coil or radiofrequency (RF) transmitter, enabling sustained or rechargeable energy delivery without the need for percutaneous connectors or frequent surgical intervention.

Illustrative embodiments enable the simultaneous treatment of multiple female pelvic health disorders. To that end, the system may include multiple neuromodulation devices to simultaneously treat SUL, OAB, POP and FL, etc. by neuromodulating specific target nerves that are key to each of the disorders being addressed. Each neuromodulation device 100 is capable of delivering a variety of stimulation patterns (e.g. afferent and efferent) and sensing the nerve response to stimulation. Satellite neuromodulation devices (shown in black in FIG. 3N-3E) may receive induction power and stimulation commands from a principal neuromodulation device 100 (shown in white in FIG. 3N-3E). To that end, the primary neuromodulation device 100 may include a wireless power transmitter (e.g., a wireless power transmitter coil) and the satellite neuromodulation devices may include a wireless power receiver circuitry 455 (e.g., a wireless power receiver coil). Thus, the satellite neuromodulation devices 100 may not include a battery (also referred to as a batteryless device), thereby providing a reduced size. However, in some embodiments, the satellite neuromodulate devices may include the battery. As an example, the battery may be a 3 mAh battery (e.g., EnerSys Quallion 3, or Resolution 3 mAh battery or a smaller solid state lithium battery or any other technology that provides adequate power).

The battery-powered principal neuromodulation device 100 may receive sensing data from the satellites. The sensing data, which may include electromyography (EMG) to sense muscle contractions, electroneurography (ENG) to sense nerve response and/or accelerometers to sense motion, among other things, may be used by the principal neuromodulation device 100 in the closed-loop feedback control of stimulation and the coordination of the therapies. With the addition of sensing and inter-implant communication technology to the platform, the treatment of multiple conditions may be coordinated. Since the larger principal neuromodulation device 100 may contain a significant amount of processing power, it can serve as a hub for optimal pelvic health.

In some embodiments, pelvic organ prolapse (POP) is treated using a distributed neuromodulation architecture that includes a principal neuromodulation device 100 and one or more satellite neuromodulation devices. This configuration enables coordinated therapy across multiple pelvic nerves and muscle groups.

As shown in FIG. 3O the principal neuromodulation device 100A (white) is implanted on a larger pelvic nerve (e.g., 1-6 mm in diameter) and includes a processor, power source, and one or more wireless communication coils. In some embodiments, the principal device 100A includes three orthogonally arranged coils or a combination of a conventional coil with orthogonal double-D coils to enable efficient omnidirectional power and signal propagation. The principal device 100A is configured to deliver induction power and stimulation commands to a plurality of satellite neuromodulation devices (black), each positioned on smaller, distal nerve branches ranging from approximately 100 microns to 1.5 mm in diameter.

Each satellite neuromodulation device 100B includes individualized nerve engagement features configured to interface with specific nerve targets. In various embodiments, the devices may include a stationary, deformable, or movable arm that defines a chamber configured to couple to the appropriate nerve size. The chamber may be proportional to the target nerve diameter, such that, for example, a treatment for POP includes neuromodulation devices having chambers configured to receive nerves of a variety of sizes. In various embodiments, the chamber is sized relative to the target nerve so that it provides less than 4 kPa of pressure to the nerve as it is stimulated by an electrode in the chamber. Additionally, or alternatively, the chamber may be configured so as to not reduce a cross-sectional area of the nerve more than 10%. In various embodiments, the cross-sectional area of the nerve is not reduced, but the cross-sectional shape may be changed. In a similar manner, if the device 100 has a channel through which the nerve travels to get to the chamber, the channel may be sized to reduce the cross-sectional nerve size no more than 25%-30% at any point as the nerve travels through the channel. impart less than 6.7 kPa on the nerve to prevent structural damage to the nerve. For example, the channel may have a cracking pressure of less than 6.7 kPa. In various embodiments, the device 100 100 is configured so that less than 10 kPa or less than about 1.5 psi of pressure is applied to the nerve. Of course, some embodiments may provide higher pressures than disclosed herein.

Although various embodiments describe a device 100 for coupling to, and treating, nerves having diameters of between about 0.2 mm and about 4 mm, it should be understood that such devices and methods are scalable to accommodate a variety of different sized nerves. For example, one skilled in the art may use the disclosure herein to configure the device 100 to couple with larger nerves having diameters of between about 5 mm and about 8 mm. These devices may be configured for long-term coupling with the various nerve sizes without damaging the nerve (e.g., by applying pressure to the nerve that is less than 4 kPa). Thus, in various embodiments, the devices are sized appropriately for a respective target nerve for atraumatic coupling. Atraumatic coupling provides less than a 4 kPa sustained pressure on the nerve when the nerve is in the chamber (e.g., in the chamber for many hours, days, etc.). Furthermore, atraumatic coupling provides less than 6.7 kPa when passing through the channel (e.g., pass through the channel for a short time period of less than 1 minute).

As used herein, the term "coupling to a nerve" or "engaging a nerve" is intended to encompass not only direct attachment or interfacing with an isolated peripheral nerve, but also interfacing with anatomical structures that include the nerve within a broader complex. These structures may include, but are not limited to, neurovascular bundles, and connective tissue sheaths that surround or encapsulate the nerve.

In many anatomical locations, particularly in the pelvic region and at distal branches of peripheral nerves, the nerve is co-located with one or more adjacent blood vessels, lymphatic vessels, and fibrous or connective tissue elements. These components together form what is commonly referred to as a neurovascular bundle or nerve plexus. Accordingly, when an implantable neuromodulation device 100 such as a nerve clip or cuff is "coupled" to a nerve, it may in practice couple with a target structure that includes the nerve along with surrounding vascular and connective components.

The present disclosure recognizes that in such embodiments, the electrode array, housing, or fixation mechanism may contact or envelop tissue beyond the nerve alone. Such interfacing is still considered "nerve coupling", provided that the structure being engaged contains a nerve that is subject to stimulation or sensing. In some instances, the nerve may be only one of several components within the engaged tissue structure, and the precise positioning of the stimulation or sensing elements may be based on anatomical access, surgical approach, or device sizing.

Furthermore, in some cases the nerve within the target structure may comprise multiple small fascicles, which may be spatially separated or partially insulated by surrounding connective tissue. The present system accommodates anatomical complexity by allowing for electrode configurations, sizing ranges, and conformable materials capable of delivering effective neuromodulation even in the presence of heterogeneous or distributed fascicular anatomy.

Thus, all references in this application to coupling the device 100 to "a nerve," "a target nerve," or "nerve interfacing" should be understood to include coupling to any anatomical structure that includes the target nerve, whether isolated or embedded within a broader multi-tissue bundle.

As described above, in various embodiments, implantable neurostimulation devices 100 (e.g., nerve clips, cuffs, or clamps) are designed with specific geometries and mechanical features to interface with nerves or nerve-containing structures of different sizes. The nerve interface may target an isolated nerve, or alternatively a target structure that includes the nerve along with associated tissue such as blood vessels, connective tissue, or other neurovascular components, as discussed above. Accordingly, the size and geometry of the neurostimulation device 100 (e.g., the channel and/or the chamber) are selected to accommodate the cross-sectional area of the entire target structure, not just the nerve itself.

To support a wide range of anatomical targets, the system may include a plurality of stimulation devices 100 with different sizing profiles. These may be provided individually or as part of a kit tailored for particular clinical procedures or therapeutic indications (e.g., stress urinary incontinence, fecal incontinence, or pelvic organ prolapse). A typical kit may include multiple neurostimulation devices 100 with distinct channel and chamber geometries to accommodate the known range of target structure sizes for that specific indication.

Each neurostimulation device 100 comprises a channel region into which the nerve or bundle is initially inserted and a chamber region in which the structure ultimately rests. In some embodiments, the device 100 includes one or more movable or deformable arms made of flexible materials (e.g., silicone or elastomer) that allow the channel width to temporarily expand during insertion and then contract to a more stable configuration for chronic implantation.

The chamber is generally designed to match the cross-sectional area of the largest nerve or neurovascular bundle in the expected size range. In preferred embodiments, the fit between the device 100 and the nerve or bundle is close, with no more than approximately 10% variance from the ideal cross-sectional area, thereby minimizing slippage while avoiding excessive compression. In solid-state chambers (non-flexible) neurostimulation device configurations, this 10% range may represent the allowable compression window for safe long-term placement without inducing nerve damage.

The following table presents exemplary channel and chamber sizing values for devices targeting different nerve or neurovascular bundle size ranges in accordance with illustrative embodiments for neuromodulation devices 100 (e.g., particularly those including one or more movable or deformable arms):

TABLE 2

| Neuromodulation Device with Moveable and/or Deformable Arm | | |
|---|---|---|
| Target Nerve/ Bundle Size Diameter | Channel minimum cross-sectional dimension (in closed configuration) | Chamber Max size (+/− 10%) |
| 100-400 μm | 60 μm | Cross-sectional area of a nerve having a diameter of 400 μm (~0.1257 $mm^2$) |
| 500 μm-1 mm | 300 μm | Cross-sectional area of a nerve having a diameter of 1 mm (~0.7854 $mm^2$) |
| 1 mm-3 mm | 600 μm | Cross-sectional area of a nerve having a diameter of 3 mm (~7.0686 $mm^2$) |
| 4 mm-7 mm | 2.4 μm | Cross-sectional area of a nerve having a diameter of 7 mm (~38.48 $mm^2$) |
| 7 mm-10 mm | 4.2 μm | Cross-sectional area of a nerve having a diameter of 10 mm (~78.54 $mm^2$) |

Table 2 presents exemplary channel and chamber sizing values for neuromodulation devices configured to engage target nerves or neurovascular bundles of varying size ranges, in accordance with illustrative embodiments. For devices 100 incorporating a movable or deformable arm, two dimensions are described: (1) a minimum channel cross-sectional dimension, which refers to the narrowest distance between two opposing internal surfaces of the device 100, and (2) a maximum chamber cross-sectional area in the device's 100 open configuration, which corresponds to the maximum target anatomy the device is designed to accommodate.

For example, a chamber dimensioned to accommodate a 400-micron-diameter nerve or neurovascular bundle in its open state may have a cross-sectional area equivalent to that of a 400-micron circle, computed using the formula $\pi \cdot r^2$ (yielding approximately 0.126 $mm^2$, where r=200 microns). This area serves as a reference to ensure that the chamber can receive anatomical structures of comparable size.

Importantly, the chamber itself need not have a circular shape. In practice, the internal cross-section of the chamber is often non-regular, such as elliptical, polygonal, or asymmetric, depending on the device 100 geometry. Similarly, the target nerve or neurovascular bundle, though roughly circular in native state, can elastically deform into a non-circular shape without incurring damage, so long as the compressive forces remain within atraumatic thresholds. Accordingly, a structure with a circular cross-sectional area may be safely accommodated in a chamber of equal area but different shape, preserving function and minimizing risk of ischemia, demyelination, or other compression-induced injury.

This design flexibility allows the use of a single chamber geometry to effectively and safely engage a range of anatomical targets with varying shapes and minor size deviations, particularly when combined with deformable or biased arm elements that dynamically conform to the target structure.

Table 3 presents exemplary channel and chamber sizing values for devices 100 targeting different nerve or neurovascular bundle size ranges in accordance with illustrative embodiments for neuromodulation devices 100 (e.g., particularly those having fixed channels and/or chambers):

TABLE 3

| Neuromodulation Device with Stationary Channel and/or Chamber | | |
|---|---|---|
| Target Nerve/ Bundle Size | Channel Width | Chamber size (+/− 10%) |
| 100 | 60 μm | Cross-sectional area of a nerve having a diameter of 100 μm |
| 200 μm | 120 μm | Cross-sectional area of a nerve having a diameter of 200 μm |

TABLE 3-continued

| Neuromodulation Device with Stationary Channel and/or Chamber | | |
|---|---|---|
| Target Nerve/ Bundle Size | Channel Width | Chamber size (+/− 10%) |
| 300 μm | 180 μm | Cross-sectional area of a nerve having a diameter of 300 μm |
| 400 μm | 240 μm | Cross-sectional area of a nerve having a diameter of 400 μm |
| 500 μm | 300 μm | Cross-sectional area of a nerve having a diameter of 500 μm |
| 600 μm | 360 μm | Cross-sectional area of a nerve having a diameter of 600 μm |
| 700 μm | 420 μm | Cross-sectional area of a nerve having a diameter of 700 μm |
| 800 μm | 480 μm | Cross-sectional area of a nerve having a diameter of 800 μm |
| 900 μm | 540 μm | Cross-sectional area of a nerve having a diameter of 900 μm |
| 1 mm | 600 μm | Cross-sectional area of a nerve having a diameter of 1 mm |
| 1.5 mm | 900 μm | Cross-sectional area of a nerve having a diameter of 1.5 mm |
| 2 mm | 1.2 mm | Cross-sectional area of a nerve having a diameter of 2 mm |
| 2.5 mm | 1.5 mm | Cross-sectional area of a nerve having a diameter of 2.5 mm |
| 3 mm | 1.8 mm | Cross-sectional area of a nerve having a diameter of 3 mm |
| 3.5 mm | 2.1 mm | Cross-sectional area of a nerve having a diameter of 3.5 mm |
| 4 mm | 2.4 mm | Cross-sectional area of a nerve having a diameter of 4 mm |
| 5 mm | 3 mm | Cross-sectional area of a nerve having a diameter of 5 mm |
| 6 mm | 3.6 mm | Cross-sectional area of a nerve having a diameter of 6 mm |
| 7 mm | 4.2 mm | Cross-sectional area of a nerve having a diameter of 7 mm |
| 8 mm | 4.8 mm | Cross-sectional area of a nerve having a diameter of 8 mm |
| 9 mm | 5.4 mm | Cross-sectional area of a nerve having a diameter of 9 mm |
| 10 mm | 6 mm | Cross-sectional area of a nerve having a diameter of 10 mm |

The values in Tables 2 and 3 are intended to serve as representative examples and may be adjusted based on anatomical data, specific clinical application, or desired coupling mechanics. In embodiments using flexible silicone-based designs, the channel and chamber dimensions allow for secure retention of differently sized structures via compliant deformation of the arms or walls of the device 100.

Thus, the above noted stratification of target nerve or neurovascular bundle sizes and corresponding device 100 dimensions presented herein is provided by way of example.

In various embodiments, the neuromodulation devices 100 may be configured with finer or broader size bands, or alternative stratification schemes depending on clinical need, manufacturing preference, or surgical approach. The disclosed sizing are not intended to limit various embodiments.

In some cases, surgical or anatomical variability may result in the nerve or target structure being slightly outside the preferred range. The device 100 may still be used in such circumstances, provided that mechanical deformation remains within the safe compression limits and do not impair tissue perfusion or nerve function.

The satellites 100B receive power and control signals from the principal device 100A and may deliver stimulation in response to closed-loop control signals coordinated centrally. Sensing modalities, either integrated into the satellites or implemented as stand-alone implanted sensors, provide physiological feedback to the principal device.

The system may include a range of sensors 192 including electromyography (EMG), electroneurography (ENG), accelerometers 77, electrochemical sensors, and strain sensors. In one embodiment, EMG sensors 192 include needle-like probes that embed into a muscle or clip-like structures that attach to muscle surfaces with an electrode on the underside. Accelerometer sensors 77 may be configured similarly to EMG sensors 192 but lack the surface electrode. Electrochemical sensors 192 may include multiple fine electrodes for detecting biochemical signals, while strain sensors 192 include two anchoring points and a stretchable sensing element that detects deformation or relative positional changes of tissue structures. These sensors 192 transmit data to the principal neuromodulation device, enabling adaptive closed-loop coordination of therapy.

The principal neuromodulation device 100A receives the physiological data and adjusts therapy delivery dynamically, including modulation of pulse timing, amplitude, and duty cycle across the satellite network. This configuration enables simultaneous, individualized stimulation of multiple nerves to restore muscular support and prevent or repair pelvic organ prolapse. The architecture may further be extended to coordinate treatment of coexisting conditions such as stress urinary incontinence (SUI), overactive bladder (OAB), and fecal incontinence (FI), using a unified feedback-based control framework.

For the sake of clarity in the description and figures, various embodiments may refer to a principal neuromodulation device as device 100A and one or more satellite neuromodulation devices as device 100B, in order to distinguish between their respective roles and features within a distributed architecture. However, unless otherwise specified, the general reference device 100 is used throughout the application to refer generically to any neuromodulation device, regardless of its specific configuration, capabilities, or role within a system. Thus, the description of device 100 is intended to encompass principal, satellite, standalone, or otherwise coordinated neuromodulation devices as appropriate in the given context. The use of specific lettered suffixes (e.g., 100A, 100B) is for illustrative convenience only and should not be interpreted as limiting the scope of the disclosure or claims.

In some embodiments, population and patient-specific data are collected over time to create a database to train an AI-controlled system.

Stimulation parameters are utilized to quantify the properties of the signal (e.g. electricity) applied to a nerve. Although general parameter settings are provided herein, it should be noted that selected stimulation parameters may vary from nerve to nerve, patient 105 to patient 105 and application to application. Optimal stimulation parameters are affected by one or more of electrode geometry, electrode material, the nerve target, and the physiology of the function that is modified, for example. The parameter settings are derived based on one or more of the types of treatment (nerve blocking, etc.), feedback from one or more probe stimulations, user settings, nerve characteristics (type, size), duration of treatment, feedback from one or more sensors, and nerve condition, for example.

Stimulation parameters are not always static. They can be altered (i.e. increased or decreased) within a treatment session and/or over a series of treatment sessions. For example, the applied current to a nerve can increase commensurate with nerve healing and/or strengthening to promote further nerve healing and/or strengthening. In other embodiments, the frequency of the stimulation pattern may be varied over time to modulate the therapy. In some embodiments, stimulation levels and or frequency are diminished over time to effectively wean a patient 105 from nerve stimulation therapy. Stimulation parameters of various embodiments for nerve stimulation may be mono-phasic (i.e. unipolar) while other forms may be biphasic (i.e. a stimulation of one polarity is followed by a stimulation of the opposite polarity to reset the condition of the nerve post stimulation). In some embodiments, nerve stimulation is tri-phasic in that a nerve is actively reset prior to stimulation by applying reverse polarization first. Discussion of a particular type of stimulation should be considered as disclosing all three of these forms.

FIGS. 3P-3W schematically shows stimulation parameters in accordance with illustrative embodiments. Specifically, the figures illustrate the structure and timing characteristics of electrical stimulation waveforms used in the disclosed neuromodulation therapy. These waveforms are organized into pulses, pulse trains, and therapy sessions, each defined by specific parameters to ensure safe and effective nerve activation.

Pulses

As known by those skilled in the art, a pulse refers to a single stimulation event delivered at a defined point in time, which may include one or more phases of electrical current or voltage. A pulse begins at the onset of its first phase and ends at the completion of its final phase. Pulses may be monophasic, biphasic, triphasic, or multiphasic. The time between the start of successive pulses, referred to as the pulse period or interpulse interval, is determined by the selected stimulation frequency. In various embodiments, the stimulation parameters include a pulse width (also referred to as pulse duration) that determines the amount of time a nerve fiber is subjected to a given stimulation current during an individual phase of a pulse. Within the context of a biphasic or multiphasic waveform, each pulse consists of two or more discrete phases (e.g., a cathodic phase followed by an anodic recovery phase), and the "pulse width" corresponds to the duration of a single phase rather than the cumulative length of all phases combined. Thus, a biphasic pulse having a 1:1 ratio may include two symmetric phase pulse widths of 150-500 microseconds each, whereas a biphasic pulse with an asymmetric ratio may have different phase pulse widths, and at least one of those phase widths should fall within the specified therapeutic range to achieve neural activation.

Pulse width is functionally significant because it determines the time over which current is applied to excitable tissue, and longer phase durations selectively recruit a greater number of axons, particularly small-diameter or unmyelinated fibers. The combination of amplitude and phase-specific pulse width collectively shapes the activation threshold for different fiber populations, influencing depolarization threshold, sensation threshold, motor threshold, and pain threshold. Accordingly, embodiments described herein define phase pulse width as the duration of a single stimulation phase, while "pulse duration" may refer to the full time span of all phases together, permitting clear characterization of multiphasic waveforms and enabling precise control over neural recruitment and safety.

Pulse Amplitude: The current or voltage level applied during the stimulation pulse. This can be cathodic or anodic stimulation.

Interpulse Delay: The interval between consecutive pulses.

Frequency (Hz): The number of pulses delivered per second.

Phase: The number of phases within one stimulation pulse. Most common are: monophasic stimulation which is one active pulse followed by a rest period. Biphasic stimulation is one active stimulation and one recovery stimulation in one pulse. Triphasic is two active stimulation and one recovery stimulation in in one pulse or reverse, one active and two recovery stimulations.

Pulse Period (μsec): The time between the start of one pulse and the next, which is dependent on the stimulation frequency.

Recovery Ratio: The ratio of the stimulation pulse to the recovery pulse in the biphasic (and triphasic) stimulation. In a 1:1 ratio the stimulation and recovery pulse are equal and inverse. In 1:2 the recovery amplitude is ½ the active amplitude for double the pulse width.

Figure 3P:
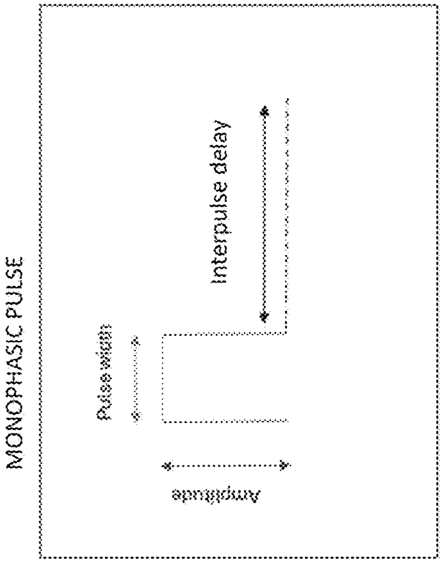
FIGS. 3P-3W schematically show stimulation parameters in accordance with illustrative embodiments.
Figure 3Q:
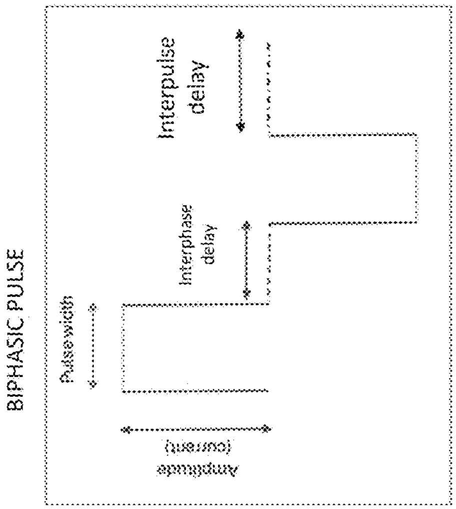

FIG. 3Q illustrates an example of a monophasic electrical stimulation pulse in accordance with illustrative embodiments. A monophasic pulse contains only a single phase of one polarity, which may be configured as either a cathodic (negative-going) or anodic (positive-going) pulse depending on the stimulation circuitry. In contrast, biphasic waveforms include two sequential phases of opposite polarity; monophasic pulses therefore lack both an interphase delay and any secondary charge-balancing phase.

The depicted pulse includes a defined pulse amplitude and a pulse width, which corresponds to the duration of the sole active phase. Following completion of this phase, an interpulse delay extends until the start of the next pulse in the sequence. The combination of pulse width and interpulse delay is defined by the stimulation frequency, allowing the system to deliver a train of monophasic pulses at any desired repetition rate to meet therapeutic objectives.

In various embodiments, pulse amplitude, pulse width, and frequency may be adjusted independently, regardless of whether the system is configured to deliver monophasic or biphasic stimulation. Because monophasic stimulation omits the second, opposite-polarity phase, the resulting neural activation and recovery behavior may differ from that produced by biphasic pulses. Accordingly, the parameters of the monophasic waveform may be selected based on the characteristics of the targeted nerve tissue and the specific physiological response sought.

FIG. 3P-3S illustrate examples of monophasic and biphasic stimulation pulses in accordance with illustrative embodiments. The waveform includes a first (active) phase of defined polarity and amplitude, followed by a second (recovery) phase of opposite polarity. In FIG. 3P, the amplitude of the recovery phase is the same as the amplitude of the active phase.

Figure 3R:
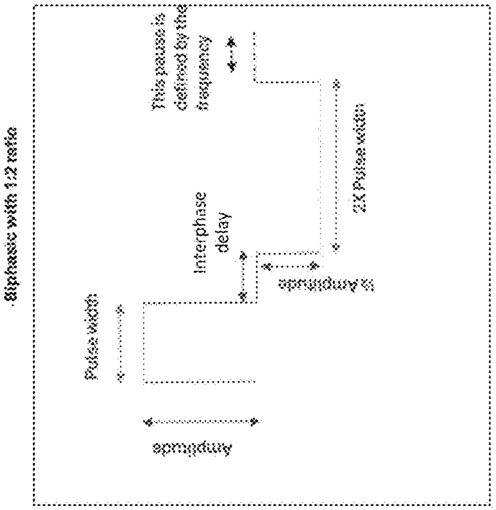

In FIG. 3R, the amplitude of the recovery phase is one-half the amplitude of the active phase, and its duration is twice the pulse width of the active phase, thereby establishing a 1:2 recovery ratio. This ratio provides an example of a charge-balancing configuration in which the total delivered charge in each phase is equivalent but distributed over different amplitudes and durations.

As shown in the figure, the two phases are separated by a short inter-phase delay, representing the interval between completion of the active phase and initiation of the recovery phase. This delay is internal to the pulse structure and is distinct from the frequency-defined pause that occurs after completion of both phases, which constitutes the interpulse interval prior to delivery of the next pulse in a stimulation train.

The waveform in FIG. 3R therefore highlights temporal and amplitude relationships that define a biphasic pulse with a 1:2 recovery ratio, including (i) the pulse width of the active phase, (ii) the amplitude and duration of the recovery phase, (iii) the inter-phase delay, and (iv) the interpulse interval determined by the selected stimulation frequency.

Figure 3S:
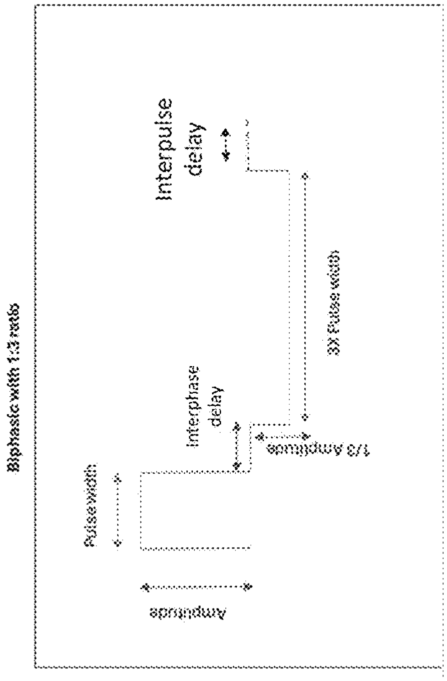

FIG. 3S illustrates an example of a biphasic stimulation pulse in accordance with illustrative embodiments. The pulse consists of a first phase of defined amplitude and pulse width, followed by a second phase of opposite polarity. As shown, the second phase has an amplitude equal to one-third of the amplitude of the first phase and a duration equal to three times the pulse width of the first phase, thereby establishing a 1:3 amplitude-duration ratio for charge balancing. A short inter-phase delay separates the two phases within the same pulse.

Figure 3T:
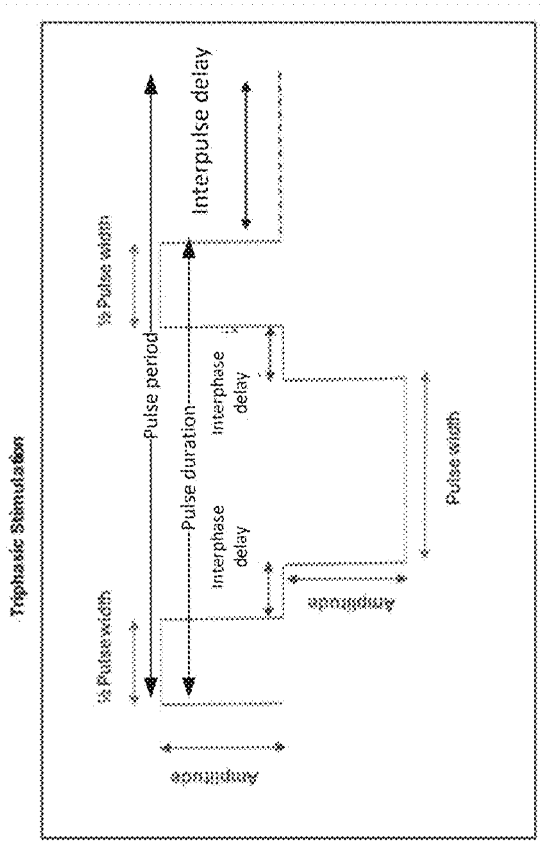
Figure 3U:
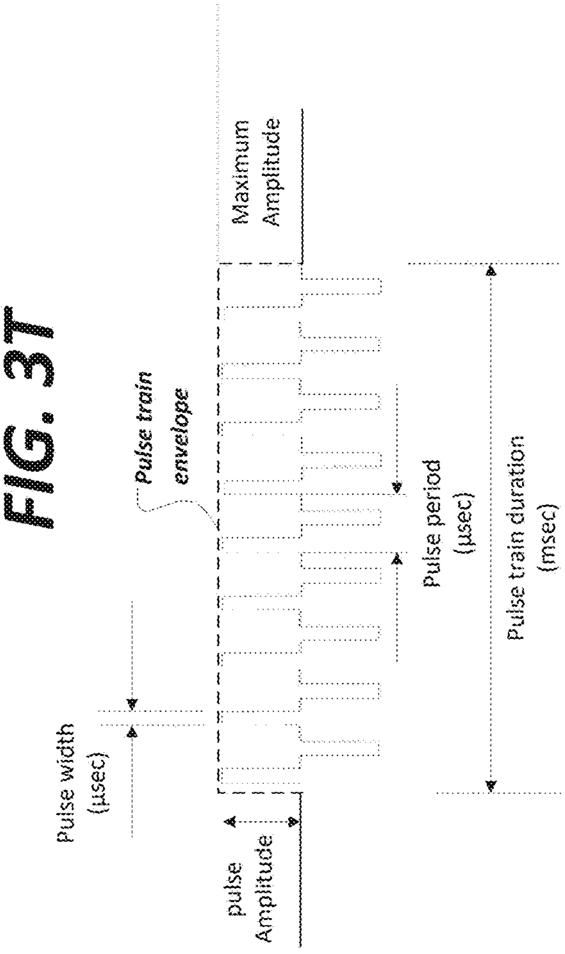

After completion of both phases, an interpulse delay occurs before the onset of the next biphasic pulse. This interpulse delay, together with the total duration of the two phases and the inter-phase delay, defines the overall pulse period and determines the stimulation frequency. The figure further demonstrates the relative timing and amplitude relationships between the two phases of an asymmetric biphasic waveform. FIG. 3T illustrates an example of a triphasic stimulation pulse in accordance with illustrative embodiments. The waveform consists of three sequential phases, each of which may have a distinct polarity, amplitude, and duration. In the illustrated configuration, the first and third phases have equal amplitude and each spans one-half of the nominal pulse width. The middle phase has opposite polarity and extends for a full pulse width. This arrangement demonstrates one form of asymmetric triphasic charge-balancing, where the combined area (charge) of the outer phases equals the area of the middle phase.

Each transition between phases is separated by a short inter-phase delay, representing the interval between the end of one phase and the beginning of the next. These interphase delays are internal to the triphasic pulse and should not be confused with the interpulse delay, which is the frequency-defined pause occurring after all three phases have completed and before the onset of the next triphasic pulse. As shown in the figure, the interpulse delay contributes to the overall pulse period and is directly related to the selected stimulation frequency.

Triphasic waveforms may be used in various embodiments to fine-tune charge balancing, reduce stimulation artifacts, or modulate nerve activation patterns. Although FIG. 3K depicts square-wave phases with a specific amplitude and duration relationship, other triphasic pulse shapes may be employed, including symmetric configurations, ramped phases, or waveforms with differing ratios, depending on the characteristics of the target nerve and the desired therapeutic effect.

Pulse Train Structure

A pulse train consists of a series of pulses delivered consecutively at a defined frequency.

Key Parameters Include:

Pulse Train Envelope: The overall shape and duration of the train.

Pulse Train Duration (sec) (aka Burst Duration): The total time the stimulation train remains active.

Amplitude: The peak stimulation level within the train. This is defined when defining the maximum pulse amplitude.

In some embodiments, the amplitude of a pulse train may be progressively increased over the course of the train, a process referred to as ramping. Ramping may be used, for example, to reduce patient discomfort at the onset of stimulation or to facilitate gradual neural recruitment. A ramp may begin at a defined starting amplitude and increase to a predetermined maximum amplitude over a specified ramp duration or over a defined number of pulses. In various embodiments, a reverse ramp may also be employed at the end of a pulse train, in which the amplitude is decreased from its maximum value according to a specified time interval or number of pulses prior to the end of the train FIG. 3L illustrates an example of a pulse train (also referred to as a pulse burst) in accordance with illustrative embodiments. The pulse train consists of a sequence of individual stimulation pulses delivered consecutively at a defined repetition rate. Each pulse within the train is characterized by a pulse amplitude and a pulse width, as shown in the figure. The pulse period, measured in microseconds, represents the interval from the start of one pulse to the start of the next pulse and determines the stimulation frequency of the train.

The collective group of pulses forms a pulse train envelope, illustrated by the dashed outline surrounding the series of pulses. The envelope may define how the amplitude evolves over the duration of the train, such as ramping up to a maximum amplitude, remaining at that level for a defined time, and optionally tapering down toward the end of the train. The pulse train duration, measured in milliseconds, extends from the onset of the first pulse in the train to the termination of the final pulse.

This figure demonstrates how individual stimulation pulses, each defined by their amplitude and width, are temporally arranged to form a pulse train of specified duration and frequency. In various embodiments, pulse trains may be repeated within a therapy session, interspersed with rest intervals to regulate neuromuscular activation or recovery.

Therapy Session

Therapy sessions are composed of multiple pulse bursts separated by rest intervals.

Burst Duration: The time each pulse train remains active.

Rest Duration: The interval between consecutive bursts, allowing neuromuscular recovery and fatigue avoidance.

Figure 3V:
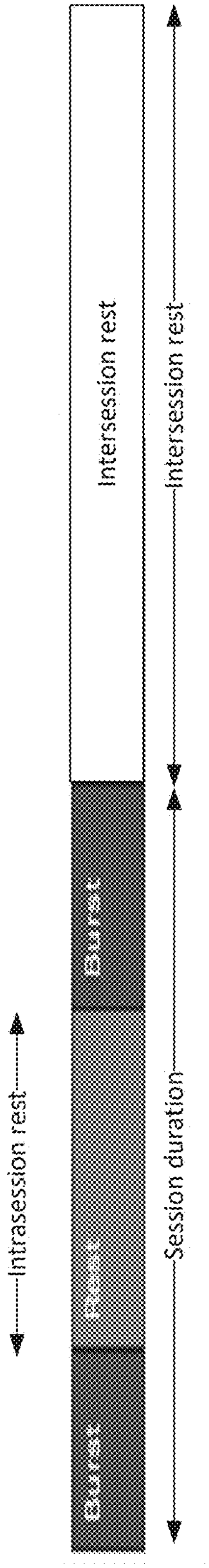

Session Duration: As shown in FIG. 3V, session duration refers to the cumulative elapsed time beginning at the initiation of the first pulse burst and ending upon the delivery of the final pulse burst in the programmed sequence. Although a rest interval may follow the final pulse burst as part of the device's programmed repeating pattern, such post-burst rest time is not considered part of the therapy treatment session duration for purposes of determining stimulation time, duty cycle, burst-to-rest ratios, or any other therapeutic parameter described herein. Pulse duty Cycle: ratio of time on to time off for stimulation during a pulse train. This is a dependent variable based on the pulse train duration and pulse rest duration.

Pulse Rest Duration (sec): Time of each rest after each pulse train within the therapy session.

FIG. 3V illustrates an example of a therapy session in accordance with illustrative embodiments. The session includes a sequence of stimulation bursts separated by rest intervals. The combination of the bursts and rest periods defines the overall session duration. This figure provides a high-level representation of how burst-based stimulation may be organized temporally within a single session. In this example, two pulse bursts are shown in the session. The session duration adds up to the total time of all pulse burst durations and pulse rest durations. In general, the rest is programmed into the repeating pulse burst, so it is factored in.

Figure 3W:
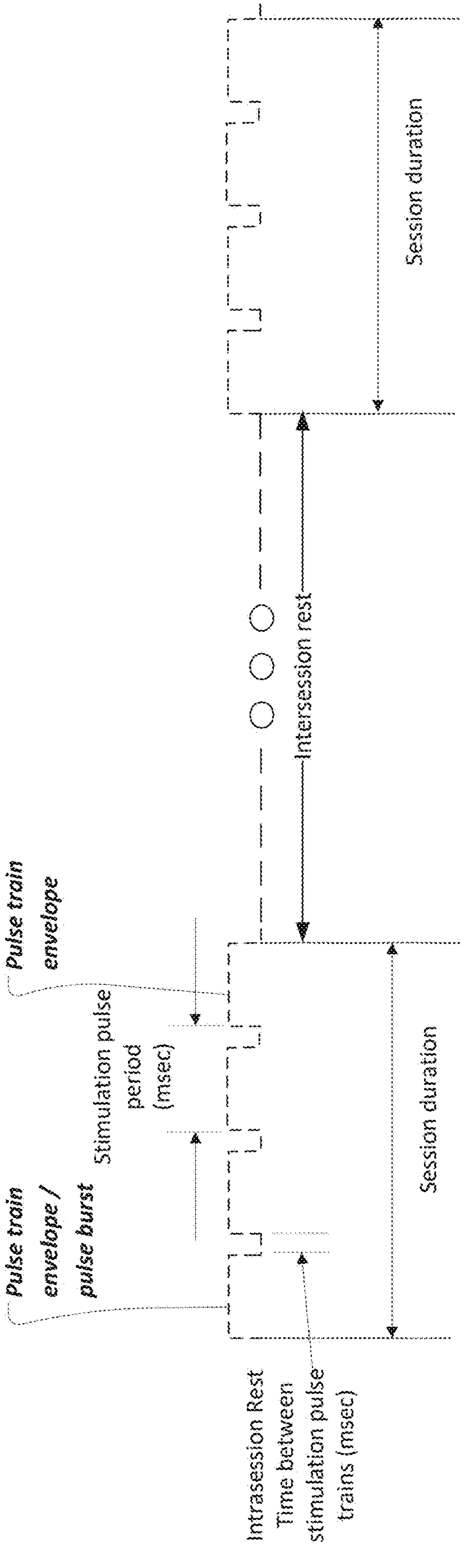

FIG. 3W illustrates a more detailed example of the stimulation timing within a therapy session. FIG. 3W schematically shows two different therapy sessions. A first session has 4 pulse trains, and a second session has 4 pulse trains. Each pulse train defines a pulse train envelope and containing a series of stimulation pulses delivered at a selected frequency. Between pulse trains, a rest interval is provided, allowing neuromuscular recovery or modulation of activation patterns. The sequence of pulse trains and rest intervals defines the session duration. This figure highlights the relationship between pulse-level timing, burst-level structure, and session-level organization. After the session is completed, a second session may occur some time later.

Each stimulation session may include one or more stimulation pulse trains. First, an intra-session rest interval refers to a period of non-stimulation between consecutive stimulation pulse trains within a single session. Second, an inter-session rest interval refers to a period of non-stimulation between distinct stimulation sessions. The figure thus illustrates that the system may implement rest intervals at multiple hierarchical levels, including intra-pulse rest intervals (e.g., interphase or interpulse delays shown in FIGS. 3P-3S), intra-session rest intervals (e.g., inter-pulse train delays), and inter-session rest intervals (e.g., delays between stimulation sessions). The duration, frequency, or scheduling of these rest intervals may be fixed, programmable, or dynamically adjusted based on sensed physiological conditions Other exemplary stimulation parameters include, but are not limited to, the following:

- Stimulation Trigger: the causal event that initiates stimulation onset. Examples include but are not limited to endogenous nerve activity, direct patient 105 control, automation (e.g. ambulation program), analysis of the output of one or more sensors 192 (e.g. crossing a threshold), and a scripted stimulation schedule (i.e. timing).
- Amplitude: The magnitude of the stimulation signal, expressed as an electrical potential difference (e.g., Volts) or an electrical current (e.g., milliamperes or microamperes).
- Pulse frequency: The number of pulses delivered per unit time. Pulse frequency=1/pulse period.
- Pulse duration: The total time during which stimulation is actively applied within a single pulse, including the duration of each phase and any interphase delay.
- Pulse period: The time from the start of one pulse to the start of the next pulse. Pulse period=pulse duration+interpulse delay.

Group Pulse Count: The number of pulses delivered within a stimulation burst or pulse group, which together span a defined burst duration.

Inter-pulse delay: The interval between the end of one pulse and the beginning of the next, determined by the stimulation frequency. The interpulse delay is not part of the pulse duration but is part of the pulse period.

Stimulation Duty Cycle: The ratio of total stimulation-on time (pulse duration) to the full pulse period. Duty cycle=pulse duration/pulse period. In some embodiments, pulses may be delivered on-demand rather than on a fixed duty cycle.

Stimulation period: The elapsed time between the initiation of two sequential stimulation groups or bursts.

Waveshape: The temporal pattern of amplitude change during a pulse, such as square, sinusoidal, triangular, or ramped profiles.

Recovery time: In a biphasic waveform, the duration of the phase that follows the active phase and provides charge balancing by applying current of opposite polarity.

Recovery ratio: The ratio of the duration of the active phase to the duration of the recovery phase (e.g., 1:2, 1:3), used to establish charge-balanced stimulation.

Phase: A segment of a pulse during which current is delivered with a defined polarity and amplitude. A monophasic pulse contains one such phase; biphasic and triphasic pulses contain two or three phases, respectively.

Example (Biphasic Pulse Train): Cathodic phase: 200 μs; Interphase delay: 50 μs; Anodic phase: 200 μs; Interpulse delay: 2000 μs, then: Pulse duration=200+50+200=450 μs, Pulse period=450 μs+2000 μs=2450 μs, and Pulse frequency≈408 Hz Various embodiments described herein relate to systems and methods for delivering electrical stimulation to nerves for therapeutic, rehabilitative, or restorative purposes. The stimulation may be applied to enhance, replace, or interfere with naturally occurring nerve signals, depending on the condition being treated and the desired physiological response. Electrical stimulation is delivered through one or more electrodes positioned proximate to a target nerve and is controlled by a stimulation controller 400, which may optionally be in communication with sensing components or signal processing modules.

In some embodiments, stimulation is used to modify or augment native nerve signals. This approach, referred to herein as signal modification stimulation, is particularly useful in patients with weakened, delayed, or incomplete neural activity. For example, in cases where a nerve produces low-amplitude signals or fails to sustain activation for the necessary duration, the system may detect the native signal and either amplify it, supplement it with a proportional stimulation, or replace it entirely with a preset stimulation pulse train. In some configurations, stimulation is prolonged beyond the duration of the natural signal to maintain the desired physiological effect. This modality may be employed, for instance, to enhance phrenic nerve signaling in order to restore or support respiratory function by stimulating diaphragm contraction.

Other embodiments include efferent nerve stimulation, wherein the stimulation is applied to induce downstream physiological effects. This form of stimulation may be employed when voluntary or endogenous neural control is diminished, absent, or requires supplementation. The stimulation signal is typically configured to exceed the amplitude of natural neural activity to ensure dominance over any residual signal conduction. Efferent stimulation can be used to activate muscle tissue, or direct organ function. Illustrative embodiments may stimulate the phrenic nerve to drive respiration, activation of gastric nerves to influence motility or secretions, and stimulation of the pelvic floor muscles to mitigate or prevent pelvic organ prolapse.

In some embodiments, restorative or repair stimulation is applied to promote the healing or strengthening of nerves that are damaged, underutilized, or experiencing degenerative changes. This type of stimulation may be delivered continuously or intermittently at or near the activation threshold to promote axonal integrity, neuromuscular junction health, and remyelination. Restorative stimulation may halt or reverse atrophy and encourage the reintegration of the nerve pathway into normal physiological function. For example, pelvic floor stimulation may be employed not only for immediate muscle activation but also to progressively strengthen the neuromuscular system over time.

Some embodiments apply multiple stimulation types through a single nerve interface. For instance, in the treatment of stress urinary incontinence, a perineal nerve may be stimulated with a first stimulation pattern to provide immediate efferent control of the pelvic floor muscles, while a second stimulation pattern may be simultaneously or sequentially applied to promote regenerative healing of the nerve and associated muscle tissue. Over the course of treatment, the parameters of the efferent stimulation may be reduced as muscle control improves, while the restorative stimulation is adjusted to accelerate repair and strengthen the neuromuscular system.

In any of the described stimulation modalities, the parameters of the applied signal may be programmed, modulated, or dynamically adapted based on therapeutic needs. Stimulation parameters may include waveform type (e.g., monophasic or biphasic; square, sinusoidal, triangular), amplitude (sub-threshold, threshold, or supra-threshold), pulse frequency, pulse duration, pulse duty cycle, inter-pulse delay, and the number of pulses per pulse train. Additional parameters may include the stimulation duty cycle (the ratio of active stimulation time to rest time), the stimulation period (time between pulse groups), and recovery-related features such as recovery time and recovery ratio. The system may further include means for triggering stimulation manually, on a schedule, or in response to sensed physiological signals. These parameters may be selected and adapted to optimize efficacy, safety, and patient 105 comfort, and may change over time as the condition of the patient 105 evolves.

Multiple treatments may be administered through a single nerve. This is accomplished, in some embodiments, by applying more than one stimulation pattern to a single nerve. In some embodiments, stress-induced urinary incontinence (SUI) may be treated by stimulating the perineal nerve with a biphasic stimulation pattern at a set frequency to arrest nerve generation (efferent stimulation) and a second lower frequency biphasic stimulation pattern to promote healing in the nerve, neuromuscular junction and the muscle (regeneration stimulation). This approach prevents urinary incontinence from the onset of treatment via efferent control while training the nerve to respond to a stimulus and strengthening the affected muscle to restore urinary flow control over time. It should be understood that as the ability for the nerve-muscle system to control urinary flow improves, the parameters for efferent stimulation and regeneration stimulation may change over time. In one example, efferent stimulation amplitude decreases over time (days) as the nerve-muscle system heals while regeneration stimulation amplitude increases over time to promote additional healing and strengthening.

Various embodiments may include one or more controllers 400. In one embodiment, the controller 400 is implanted within a patient 105 (e.g., within the principal neuromodulation device). In other embodiments, the controller 400 is within an external device 100 (e.g. a wearable controller 400, watch, or cell phone).

Figure 4:
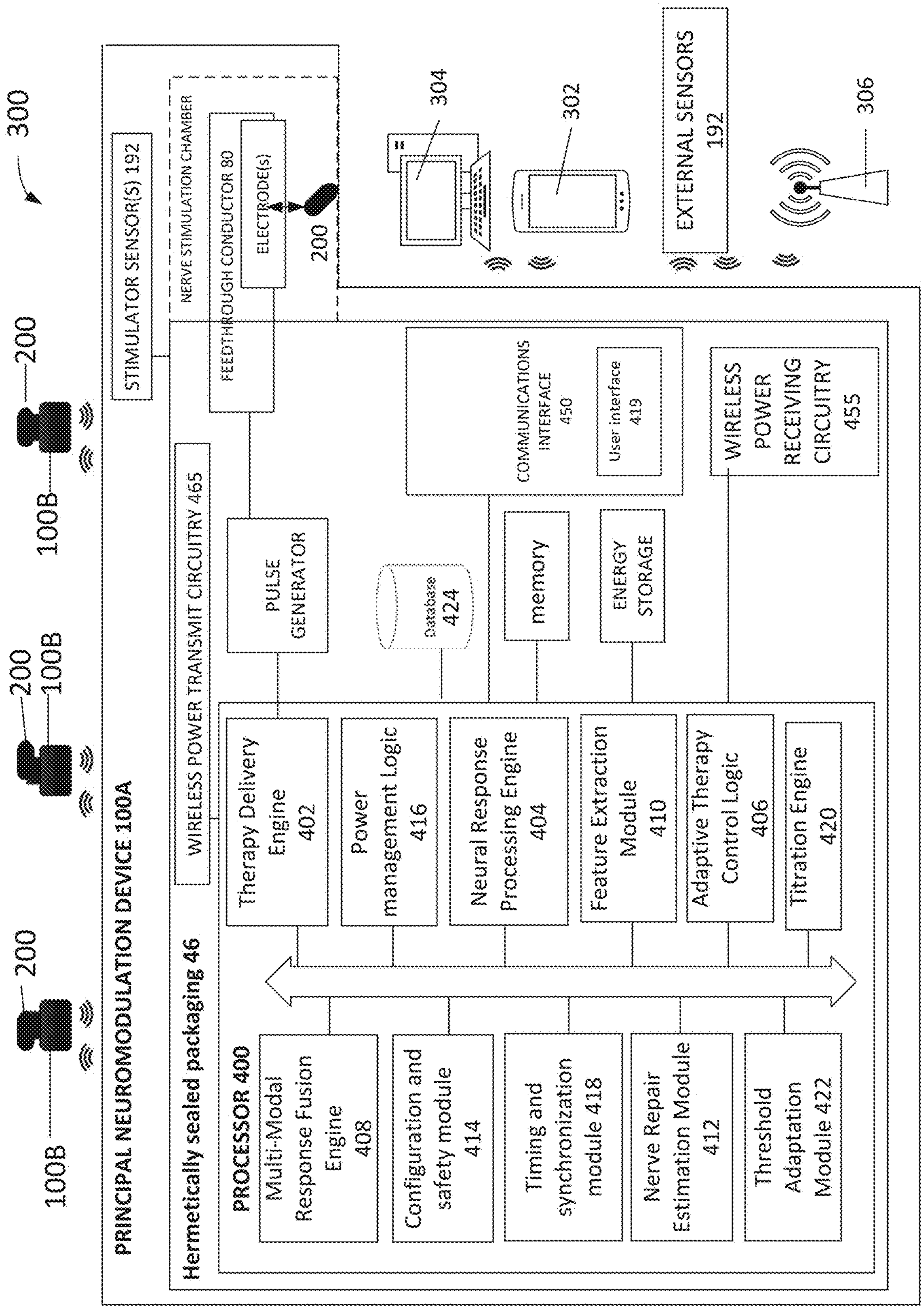
FIG. 4 schematically shows details of the neuromodulation device controller in accordance with illustrative embodiments.

FIG. 4 schematically shows details of the neuromodulation device 100 controller 400 in accordance with illustrative embodiments. The controller 400 may be physically housed within the housing of the neuromodulation device 100, for example, in the primary neuromodulation device 100A. Each of the components in FIG. 4 operatively connected by any conventional interconnect mechanism. FIG. 4 simply shows a bus communicating each of the components. Those skilled in the art should understand that this generalized representation can be modified to include other conventional direct or indirect connections. Accordingly, discussion of a bus is not intended to limit various embodiments.

Indeed, it should be noted that FIG. 4 only schematically shows each of these components. Those skilled in the art should understand that each of these components can be implemented in a variety of conventional manners, such as by using hardware, software, or a combination of hardware and software, across one or more other functional components. For example, the stimulator (discussed in detail below) may be implemented using a plurality of microprocessors executing firmware. As another example, the feedback analyzer may be implemented using one or more application specific integrated circuits (i.e., "ASICs") and related software, or a combination of ASICs, discrete electronic components (e.g., integrated circuits), and microprocessors. Accordingly, the representation of the feedback analyzer and other components in a single box of FIG. 4 is for simplicity purposes only. In fact, in some embodiments, the feedback analyzer of FIG. 4 is distributed across a plurality of different components, not necessarily within the same housing or chassis.

It should be reiterated that the representation of FIG. 4 is a significantly simplified representation of an actual controller 400. Those skilled in the art should understand that such a device 100 has other physical and/or functional components, such as central processing units, other packet processing modules, and short-term memory. Accordingly, this discussion is not intended to suggest that FIG. 4 represents all of the elements of the controller 400.

As shown in FIG. 4, the neuromodulation device 100 can include a sensor 192 interface that interfaces with the sensors, a data storage, a network interface, a user interface, at least one battery (in some embodiments, the battery may be omitted—for example in the satellite, a wireless power transmitter 465 (e.g., in a primary device 100A) and/or a wireless power receiver 455 (e.g., in a satellite device 100B), wireless communication, a stimulator, and at least one processor.

In various embodiments, at least one principal neuromodulation device and one or more satellite neuromodulation devices, each designed to perform complementary roles in a multi-site, closed-loop stimulation framework. These devices may share a set of common internal components but differ in complexity, processing capacity, and stimulation control responsibilities depending on their respective roles in the system.

In various embodiments, both the principal 100A and satellite devices 100B have the following internal components:

- Pulse Generator: A core functional unit that generates electrical stimulation waveforms with specified parameters such as amplitude, frequency, pulse width, and duration. The pulse generator converts digital or analog instructions into current or voltage pulses delivered to the nerve via electrodes. In various embodiments, each satellite neuromodulation device 100B comprises a local pulse generator configured to receive stimulation commands from the principal neuromodulation device and generate corresponding electrical stimulation waveforms for delivery to a target peripheral nerve.
- Stimulation Circuitry: Includes the necessary analog drivers, charge-balancing circuits, isolation switches, and safety monitors required to deliver safe and effective stimulation. The circuitry ensures precise timing and amplitude control, minimizes leakage current, and maintains compliance with bioelectrical safety standards.
- Electrode Interface: A conductive interface coupled to the nerve tissue, such as a bipolar or monopolar electrode array integrated into a flexible cuff, clip, or injectable lead. This interface transmits stimulation pulses from the circuitry to the target nerve and, in some cases, receives bioelectrical signals when used for sensing.
- Communication Interface: A wireless module comprising a radio frequency (RF) transceiver, antenna or coil, and communication protocol controller 400 (e.g., BLE, NFC, custom telemetry). This interface supports two-way communication between the principal and satellite devices, and optionally with external systems such as clinician consoles or mobile apps.
- Power Receiving Circuitry: An inductive receiver coil or capacitive coupling interface that allows the device to harvest energy from an external or implanted source. Includes rectifiers, voltage regulators, and protection circuitry to ensure stable power delivery under varying load conditions.
- Energy Storage Module: May include a rechargeable battery, supercapacitor, or charge reservoir to buffer harvested energy for delivery during active stimulation periods, ensuring smooth operation even under intermittent or variable wireless power availability.
- Biocompatible Packaging: A hermetically sealed housing made of ceramic, titanium, silicone, or polymer encapsulant that protects internal electronics from body fluids and mechanical stress while ensuring safe chronic implantation.

In addition to the components above, the principal neuromodulation device 100A includes several advanced modules that support system-wide control, coordination, and decision-making:

- Processor/controller 400: A microcontroller, application-specific integrated circuit (ASIC), or system-on-chip (SoC) that executes control algorithms, closed-loop logic, and stimulation coordination routines. It processes incoming biosignals, computes adaptive parameter updates, and issues commands to the satellite devices.
- Non-Volatile Memory: Stores firmware, stimulation presets, biosignal history, calibration data, session logs, and patient-specific therapy settings. May include flash memory or magnetoresistive RAM (MRAM) for long-term retention.

Wireless Power Transmission Module: Comprising one or more transmission coils, such as three orthogonally arranged coils or a double-D coil configuration, this module enables efficient omnidirectional inductive power delivery to satellite devices implanted at different orientations or anatomical positions.

Sensor Aggregation Hub: Interfaces with one or more implanted or external sensors, including EMG, ENG, strain, pressure, accelerometers, and electrochemical sensors. Collects and digitizes biosignals for processing by the controller 400.

Telemetry Link to External Systems: Enables secure communication with an external controller, which may be a handheld programmer, clinician tablet, or patient mobile phone. Supports over-the-air firmware updates, therapy adjustments, and data export.

Time Synchronization Logic: Maintains synchronized clocks and stimulation timing coordination across multiple satellite devices, allowing for temporally controlled stimulation routines (e.g., alternating pulses, burst sequences, or phased contraction strategies).

The satellite neuromodulation devices 100B are miniaturized, peripheral implants responsible for localized stimulation and, in some embodiments, sensing. In addition to shared components, each satellite 100B may include:

Miniaturized Local controller 400: A reduced-size controller 400 (e.g., ASIC or minimal microcontroller) capable of interpreting incoming commands from the principal device and executing the corresponding stimulation waveforms locally.

Minimal Memory: May include volatile or non-volatile memory sufficient to store current session parameters, identifiers, or temporary biosignal flags.

Local Sensing Module: Some satellites may include an embedded EMG electrode, ENG pickup, impedance sensor, or tissue strain sensor. These signals may be transmitted upstream to the principal device or used to adjust stimulation locally.

Current Steering or Multi-Contact Control Circuitry: If equipped with multiple electrode contacts, the satellite may include switching logic or analog multiplexers to direct stimulation current to specific fascicles or contact zones.

Voltage and Current Regulators: Ensure consistent stimulation amplitude regardless of supply fluctuations due to variable wireless power coupling. May also enforce safety thresholds such as maximum charge per phase or duty cycle limits.

Internal Safety Watchdog: A circuit that disables stimulation if abnormal conditions are detected (e.g., temperature rise, excess current, or device malfunction).

Collectively, this distributed architecture enables fine-grained stimulation control across multiple pelvic nerves, real-time adaptation to biosignals, and modular expansion for additional conditions. The system's ability to balance control complexity in the principal device with localized pulse execution in the satellites allows for an optimized tradeoff between functionality, power efficiency, and miniaturization of the distal implants.

In various embodiments, one or more of the functional modules described herein, such as the Signal Acquisition Module, Feature Extraction Module, Nerve Repair Estimation Module, Titration Engine, Closed-Loop Controller, or Communication Interface, may be implemented wholly or partially on external systems, including a clinician-facing external computing device 304 or a patient mobile device 302. These external devices may serve as control hubs for therapy planning, remote monitoring, or longitudinal data analysis, and may operate in tandem with implanted components to facilitate adaptive and personalized therapy. Additionally, or alternatively, one or more of the modules may be distributed to or duplicated within satellite neuromodulation devices 100B. For example, a satellite device may locally process sensor data, execute simplified closed-loop routines, or implement fallback control algorithms when communication with the primary device 100A is temporarily lost. This flexible distribution of control logic allows the system to maintain functionality across a range of deployment scenarios, from fully centralized to distributed architectures.

In various embodiments, the satellite neuromodulation device 100B may lack certain higher-level functional modules present in the primary neuromodulation device 100A. For example, satellite devices 100B may omit the Nerve Repair Estimation Module, Titration Engine, and Database, instead relying on the primary device 100A or an external system (e.g., computing device 304 or mobile device 302) to perform those advanced analytics and long-term therapy adaptations. Satellite devices may also forgo a Comprehensive Communication Interface, limiting their interactions to local, device-to-device communication with the primary device 100A. Additionally, satellite devices 100B may not include full Closed-Loop Control Logic, instead executing basic instructions from the primary device without independently analyzing sensor data or determining stimulation adjustments. In some embodiments, satellite devices may also omit a dedicated power source such as a battery and instead operate using wireless power received from the primary neuromodulation device 100A. By simplifying onboard functionality, satellite devices 100B can be made smaller, more power-efficient, and better suited for distal nerve targets, while still participating in a coordinated and adaptive therapy regimen governed by the primary controller (e.g., in the primary device 100A or external computing device 304). This enables satellite devices 100B to be implanted in anatomical locations where larger or more complex neuromodulation systems may not be feasible or safe. This size advantage allows for precise targeting of distal or otherwise difficult-to-access nerves, particularly within the pelvic region or other confined spaces.

The data storage can include one or more of non-transitory computer readable media, such as flash memory, solid state memory, magnetic memory, optical memory, cache memory, combinations thereof, and others. The data storage can be configured to store executable instructions and data used for operation of the controller 400. In certain implementations, the data storage can include executable instructions that, when executed, are configured to cause the processor to perform one or more functions.

In some examples, the wireless communication interface can facilitate the communication of information between the controller 400 and one or more other devices or entities over a communications network. For example, where the controller 400 is included in the primary neuromodulation device 100 100, the network interface can be configured to communicate with a remote neuromodulation device 100 such as a satellite neuromodulation device 100 or other computing device. The wireless communication interface can include communications circuitry for transmitting data in accordance with a Bluetooth® wireless standard for exchanging such data over short distances to an intermediary device(s) (e.g., other neuromodulation devices). The intermediary device(s) may in turn communicate the data to a remote server over a broadband cellular network communications link. The communications link may implement broadband cellular technology (e.g., 2.5G, 2.75G, 3G, 4G, 5G cellular standards) and/or Long-Term Evolution (LTE) technology or GSM/EDGE and UMTS/HSPA technologies for high-speed wireless communication. In some implementations, the intermediary device(s) may communicate with a remote server over a Wi-Fi™ communications link based on the IEEE 802.11 standard.

In various embodiments, the implantable device employs load shift keying (LSK) telemetry for wireless communication with an external controller. LSK telemetry operates by modulating the impedance of the implant's resonant coupling circuit to encode data onto an inductive link used for power and communication. By selectively switching a resistive or reactive element within the implant, the effective load presented to the external drive coil is varied in a controlled manner, producing corresponding amplitude or phase perturbations in the external coil current that are detected and demodulated to recover transmitted data. The telemetry system may operate at various carrier frequencies suitable for inductive coupling through biological tissue, including those allocated within the industrial, scientific, and medical (ISM) frequency bands, such as 6.78 MHz or 13.56 MHz, among others. Operation near 6.87 MHz provides an example of an ISM-compatible frequency offering favorable trade-offs between tissue penetration, coupling efficiency, and regulatory compliance.

In certain implementations, the user interface 419 can include one or more physical interface devices such as input devices, output devices, and combination input/output devices (e.g., 302 and 304) and a software stack configured to drive operation of the devices. The user interface 419 may render visual, audio, and/or tactile content. Thus, the user interface 419 may receive input or provide output, thereby enabling a user to interact with the controller 400 (e.g., via a smartphone application).

In various embodiments, the user interface 419 can include one or more physical interface devices such as input devices, output devices, and combination input/output devices, along with a software stack configured to drive operation of these devices. These user interface elements may render visual, audio, and/or tactile content to facilitate interaction. Thus, the user interface may receive input or provide output, enabling a user to interact with the controller (e.g., via a smartphone application or dedicated console).

In some embodiments, the user interface allows the patient or clinician to adjust stimulation parameters within predefined safe ranges, such as amplitude, frequency, or duty cycle, based on comfort or therapeutic goals. For example, the user may reduce amplitude if stimulation causes muscle fatigue or discomfort, or increase amplitude slightly to maintain efficacy as nerve conduction improves. The interface may also provide real-time feedback mechanisms, enabling users to report sensations, pain, or exhaustion during therapy sessions. These inputs can be processed by the controller to dynamically modify stimulation settings while ensuring compliance with the disclosed ranges.

Additionally, the user interface may display session progress, threshold confirmation, and physiological markers, such as muscle contraction or organ function indicators, allowing clinicians to monitor therapy effectiveness. In various embodiments, the interface includes preset therapy modes for different nerve types (motor, sensory, autonomic) and offers manual override options for fine-tuning. By integrating patient feedback and clinician control into the system, illustrative embodiments enhance safety, comfort, and adaptability while maintaining the regenerative and reparative benefits of the disclosed method.

The controller 400 can also include at least one battery configured to provide power to one or more components integrated in the controller 400. The battery can include a rechargeable multi-cell battery pack. In one example implementation, the battery can include lithium ion cells that provide electrical power to the other device 100 components within the controller 400. The device 100 may include a wireless power transmitted and/or a wireless power receiver for charging the battery of the device, and/or wirelessly charging the battery of an associated device.

The sensor 192 interface may communicate with one or more sensors 192 (e.g., EMG, ENG, NCV, pressure sensors, etc.) configured to monitor, quantify, and/or detect one or more parameters of the patient 105 condition and/or neuromuscular response. As shown, the sensors 192 may be coupled to the controller 400 via a wired or wireless connection.

The sensor 192 interface can be coupled to any one or combination of sensors 192 to receive other patient 105 data indicative of patient 105 neuromuscular parameters. After data from the sensors 192 has been received by the sensor 192 interface, the data can be directed by the processor to an appropriate component within the controller 400. For example, the sensor 192 interface can transmit the data to the processor which, in turn, relays the data to a feedback analyzer. The data can also be stored on the data storage.

In various embodiments, the principal neuromodulation device 100A includes a processor or controller 400 configured to manage and coordinate all aspects of therapy delivery, sensor integration, communication, and closed-loop feedback. The controller 400 may be implemented as a microcontroller (MCU), a system-on-chip (SoC), a digital signal processor (DSP), or an application-specific integrated circuit (ASIC), depending on the complexity of the implementation and the desired balance of power efficiency, processing speed, and integration density.

The controller 400 may include or interface with a variety of functional modules and logic engines to support adaptive, closed-loop therapy in real-time and over extended periods. These functional components may include, but are not limited to the following components.

The therapy delivery engine 402 manages generation and timing of therapeutic stimulation delivered through one or more direct-contact electrodes. The engine is configured to (i) initiate and terminate stimulation sessions according to a schedule, (ii) select a target nerve and/or electrode contact for delivery, and (iii) synthesize a current-controlled, charge-balanced biphasic waveform with programmable pulse amplitude, pulse width, frequency, inter-pulse delay, burst duration, burst quantity, and inter-burst rest duration. In various embodiments, the engine constrains all programmable fields to amplitude 0.1-10 mA, pulse width 150-500 μs (per phase), frequency 20-100 Hz with inter-pulse delay 25-100 μs, burst duration 3-60 s, rest duration 0.5-5 min, and burst quantity of one or more, and it computes and exposes derived values including burst-to-rest ratio and session duration.

The engine 402 implements a burst-rest state logic that guarantees timing accuracy for each burst and pause, enforces daily and weekly quotas (e.g., 1-10 sessions/day on 1-7 days/week), and inhibits initiation if safety interlocks are asserted. A waveform synthesizer within the engine produces biphasic pulses with microsecond-resolution phase timing and active or passive recharge to ensure zero net DC. An electrode contact router selects among electrode contacts or nerve sites, and may execute alternating, interleaved, phased, or staggered delivery patterns across multiple sites, while keeping the per-site parameters within the foregoing ranges.

The engine 402 interfaces to a local pulse generator and, in various embodiments, to remote or satellite neuromodulation devices, providing clock and parameter updates such that multi-device patterns remain synchronized. The engine can operate in open-loop mode using a preprogrammed schedule, and in closed-loop mode in which sensor-derived feedback (e.g., impedance, ENG/EMG, temperature, motion) adapts amplitude, pulse width, and/or frequency only within the allowed parameter bounds and subject to rate-limiters and charge-balance constraints. Throughout delivery the engine tracks compliance voltage and delivered charge, and cooperates with a safety module to gracefully derate or suspend output upon out-of-range conditions (e.g., contact loss, over-temperature, or compliance exceedance). The engine logs per-burst summaries and session adherence for clinical records.

A Neural Response Processing Engine 404 receives input from one or more implanted or external sensors, including but not limited to:

- Electromyographic (EMG) sensors, to assess muscle activation strength and timing
- Electroneurographic (ENG) sensors, to detect neural conduction or latency
- Strain sensors, to measure tissue displacement or structural engagement
- Bladder or rectal pressure sensors, for bladder or rectal pressure
- Electrochemical sensors, for metabolic or ionic changes The Neural Response Processing engine 404 digitizes and filters the raw data (e.g., bandpass filtering of EMG in the 50-500 Hz range), then extracts key features such as peak amplitude, onset latency, contraction duration, or signal variance. These features are passed to the Adaptive Therapy Control Logic 406 for further interpretation.

An Adaptive Therapy Control Logic 406 performs real-time or session-based adjustments to stimulation parameters based on sensor feedback. Closed-loop actions may include:

- Automatically reducing stimulation amplitude if muscle fatigue is detected (e.g., >20% EMG drop),
- Increasing frequency or train count in response to improved responsiveness or strength,
- Shifting stimulation focus from one nerve to another if asymmetrical recovery is detected.

The closed-loop logic may operate on a per-train, per-session, or longitudinal basis, and can be configured to maintain therapeutic effectiveness while minimizing the risk of overstimulation or patient discomfort. The Adaptive Therapy Control Logic 406 may escalate therapy routines as muscle strength improves. Furthermore, it may compensate for asymmetrical recovery across multiple nerves.

Some embodiments include a multi-modal response fusion engine 408 to achieve a more comprehensive understanding of physiological states. For example:

- EMG spikes may be correlated with strain displacement to confirm muscle engagement,
- Bladder pressure may be analyzed alongside ENG activity to assess sphincteric coordination.

The response fusion engine 408 may apply weighting schemes, temporal alignment algorithms, or heuristic models to interpret sensor data across different modalities and guide more precise therapy adjustments.

Communication Interface 450 and handles all data exchange between the principal device, satellite devices, and external systems. This includes:

- Transmission of stimulation commands and parameter updates to satellite neuromodulation devices 100B,
- Reception of sensor data or acknowledgments from satellites,
- Secure wireless communication with external controller devices, such as a clinician programmer 304, mobile phone 302, or cloud-connected hub.
- Implanted Communications: Sends commands to and receives acknowledgments or sensor data from satellite devices using RF or near-field telemetry
- External communication: Exchanges session data, logs, and therapy parameters with external devices (e.g., mobile app 302, clinician computing device 304, base station)

Supported communication protocols may include Bluetooth Low Energy (BLE), near-field communication (NFC), or custom RF telemetry. The Communications Interface may also Encrypt and authenticates data as needed The controller 400 may include a timing and synchronization module 418 to coordinate pulse delivery across multiple sites. This may involve:

- Maintaining a master clock or timestamp system,
- Scheduling stimulation trains with defined interleaving or phasing,
- Ensuring Synchronized pulses (e.g., bilateral contraction) or alternating activation between different pelvic muscle groups.

The Timing and Synchronization Module 418 maintains a master clock and schedules pulse-accurate burst and rest intervals with microsecond-level jitter control. For multi-site or bilateral delivery, it provides defined interleaving, phasing, and synchronized pulses; for distributed systems, it synchronizes satellite stimulators using time beacons or acknowledgments via the communications interface.

A Database 424 may store longitudinal data for the controller 400 to analyze. The Database 424 stores session-level parameters, delivered charge and usage statistics, biosignal features and trends, personalized baselines, adaptation histories, and patient-reported outcomes. These data support long-term optimization (e.g., progressive parameter adjustments within bounds), adherence reporting, regulatory traceability, and clinician review/export. The data may represent:

- Session-level stimulation parameters,
- Biosignal trends over time,
- Longitudinal adaptation (e.g., progressive increase of stimulation intensity as performance improves)
- Personalized baselining
- Session-to-session optimization routines
- Data export for clinician review
- Patient-reported outcomes or subjective feedback.

This information may be used to support long-term adaptation of therapy regimens, such as gradually increasing intensity as muscle strength improves or modifying the stimulation strategy in response to slow or asymmetrical recovery.

In various embodiments, the neuromodulation system includes a Titration Engine 420 a Threshold Adaptation Module 422, which work in conjunction to adjust stimulation parameters based on the evolving physiological state of the patient. The Threshold Adaptation Module 422 is configured to monitor and record stimulation-response characteristics over time, including motor thresholds, nerve conduction latency, and amplitude of evoked responses. Using data collected during therapy sessions or through periodic probe stimulations, the module tracks whether a given stimulation intensity continues to evoke the desired physiological response. If a nerve or muscle becomes more or less responsive (e.g., due to recovery, fatigue, or degradation), the module dynamically recalibrates threshold values accordingly. This adaptive threshold data is passed to the Titration Engine 420, which adjusts one or more stimulation parameters, such as amplitude, frequency, duty cycle, train duration, or pulse width, to optimize therapy delivery. For example, The Titration Engine 420 adjusts one or more stimulation parameters, such as amplitude, pulse width, frequency, burst duration, burst count, or rest duration, within the specified ranges to maintain a target response while minimizing energy and discomfort. In response to Threshold Adaptation 422 and State Estimation 412, the engine may, for example, reduce amplitude when fatigue is detected or incrementally adjust frequency or burst count when responsiveness improves, subject to safety interlocks and clinician-defined limits. This combined functionality ensures that therapy is not only safe and personalized, but also responsive to patient progress, thereby maximizing long-term therapeutic efficacy while minimizing side effects or energy waste.

Configuration and Safety Module 414 monitors system integrity and enforces safety constraints, such as:

- Maximum allowable stimulation amplitude, frequency, or duty cycle,
- Detection of abnormal tissue impedance, temperature, or signal noise,
- Watchdog timers for device responsiveness and error recovery,
- Failsafe shutdown protocols in the event of error or emergency conditions.

The module may also provide fallback routines or "safe mode" stimulation settings that allow continued operation if sensor data becomes unreliable or unavailable.

Power Management Logic 416 Especially in fully implanted systems, power management is essential. This module may control:

- Sleep and wake cycles based on stimulation demand or sensor activity,
- Power budgeting across sensors, stimulators, and telemetry modules,
- Monitoring of energy reserves in capacitors or rechargeable batteries,
- Coordination of wireless energy harvesting windows with external or internal sources.

In some embodiments, the controller 400 includes a Feature extraction module 410 configured to compute signal metrics from biosignal inputs, including but not limited to peak amplitude, time-to-peak, waveform variance, signal envelope, and latency. These features are provided to a Threshold Adaptation Module 422, which tracks changes in response thresholds over time and adjusts therapy delivery in accordance with strengthening or fatigue. These components work in conjunction with the Adaptive Therapy Control Logic 406 and Response fusion engine 408 to provide precise, state-aware modulation of therapy parameters. In various embodiments, elements of this control logic may be hierarchically distributed between the principal and satellite neuromodulation devices or integrated into an external computing platform.

In various embodiments, the neuromodulation system includes a Nerve Repair Estimation Module 412, which is a functional component of the controller or processor configured to evaluate the condition of a target nerve, neuromuscular junction, or muscle based on one or more biosignals. This module receives processed input from upstream signal acquisition and feature extraction modules, including electromyographic (EMG), electroneurographic (ENG), strain, or pressure sensors, and applies diagnostic logic to determine the current physiological state of the tissue. The module classifies the state into categories such as fatigued, weak, overstimulated, underactive, or strengthening. These classifications may be derived from absolute values, deviations from baseline, or signal trends observed across time. For example, the module may identify muscle fatigue based on a sustained decrease in EMG amplitude over repeated stimulation trains, or diagnose strengthening based on an increasing EMG response to consistent stimulation. Similarly, delayed ENG conduction latency may indicate nerve desensitization or under-recruitment. The outputs of this module inform the closed-loop control system and Titration Engine 420, enabling the system to personalize therapy delivery by adapting stimulation parameters in real time or over multiple sessions. In some embodiments, the module also integrates multiple signal modalities to refine diagnostic accuracy using response fusion logic.

These logic modules may be partially or wholly embedded within the principal device, and in some cases, simplified control routines may also reside within satellite devices to support limited autonomy. In some configurations, high-level coordination or parameter adjustment may be delegated to an external controller 400 (e.g., clinician programmer or patient mobile device), which operates in conjunction with the internal processor.

In some embodiments, a subset of this logic may also reside in satellite neuromodulation devices, enabling limited autonomous behavior (e.g., timing-based local stimulation) or local fallback behavior if communication with the principal controller 400 is temporarily lost. In other embodiments, high-level control may be distributed to an external device, such as a mobile phone, or clinician console, particularly for session planning, longitudinal trend analysis, or secure firmware updates.

In some implementations, the processor includes one or more processors (or one or more processor cores) that each are configured to perform a series of instructions that result in manipulated data and/or control the operation of the other components of the controller 400 and its various components. In some implementations, when executing a specific process (e.g., sending a signal to stimulate the patient), the processor can be configured to make specific logic-based determinations based on input data received, and be further configured to provide one or more outputs that can be used to control or otherwise inform subsequent processing to be carried out by the processor and/or other processors or circuitry with which the processor is communicatively coupled. Thus, the processor reacts to specific input stimulus in a specific way and generates a corresponding output based on that input stimulus. In some example cases, the processor can proceed through a sequence of logical transitions in which various internal register states and/or other bit cell states internal or external to the processor may be set to logic high or logic low.

As referred to herein, the processor can be configured to execute a function where software is stored in a data store coupled to the processor, the software being configured to cause the processor to proceed through a sequence of various logic decisions that result in the function being executed. The various components that are described herein as being executable by the processor can be implemented in various forms of specialized hardware, software, or a combination thereof. For example, the processor can be a digital signal processor (DSP) such as a 24-bit DSP processor. The processor can be a multi-core processor, e.g., having two or more processing cores. The processor can be an Advanced RISC Machine (ARM) processor such as a 32-bit ARM processor. The processor can execute an embedded operating system, and include services provided by the operating system that can be used for file system manipulation, display & audio generation, basic networking, firewalling, data encryption and communications.

Although the subject matter contained herein has been described in detail for the purpose of illustration, it is to be understood that such detail is solely for that purpose and that the present disclosure is not limited to the disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

The stimulator can include, or be operably connected to, circuitry components that are configured to generate electrical signals through the electrode that may cause the stimulation to be transmitted to the patient 105 through the electrode. The circuitry components can include, for example, resistors, capacitors, relays and/or switches, electrical bridges such as an h-bridge (e.g., including a plurality of insulated gate bipolar transistors or IGBTs), voltage and/or current measuring components, and other similar circuitry components arranged and connected such that the circuitry components work in concert with the stimulator and under control of one or more processors to provide, for example, stimulation at a desired frequency, amplitude and/or pattern.

In some implementations, the processor includes one or more processors (or one or more processor cores) that each are configured to perform a series of instructions that result in manipulated data and/or control the operation of the other components of the controller 400 and the device 100. In some implementations, when executing a specific process (e.g., EMG detection, controlling the stimulator), the processor can be configured to make specific logic-based determinations based on input data received, and be further configured to provide one or more outputs that can be used to control or otherwise inform subsequent processing to be carried out by the processor and/or other processors or circuitry with which processor is communicatively coupled. Thus, the processor reacts to specific input stimulus in a specific way and generates a corresponding output based on that input stimulus. In some example cases, the processor can proceed through a sequence of logical transitions in which various internal register states and/or other bit cell states internal or external to the processor may be set to logic high or logic low.

As referred to herein, the processor can be configured to execute a function where software is stored in a data store coupled to the processor, the software being configured to cause the processor to proceed through a sequence of various logic decisions that result in the function being executed. The various components that are described herein as being executable by the processor can be implemented in various forms of specialized hardware, software, or a combination thereof. For example, the processor can be a digital signal processor (DSP) such as a 24-bit DSP processor. The processor can be a multi-core processor, e.g., having two or more processing cores. The processor can be an Advanced RISC Machine (ARM) processor such as a 32-bit ARM processor. The processor can execute an embedded operating system, and include services provided by the operating system that can be used for file system manipulation, display & audio generation, basic networking, firewalling, data encryption and communications.

The most common control scheme is a PID (proportional, integral, differential) controller 400. The PID controller 400 may anticipate a single input and provide a single output. In embodiments having multiple satellite neuromodulation devices, the system may have multiple sensors 192 and therefore multiple inputs. These can be configured into a MISO PID controller 400—multiple inputs, single output. Illustrative embodiments may be configured to MISO PID controller 400 in multiple. As one example, each input may be in its own PID loop with a single output. As another example, the single outputs can have a weighted combination to determine the single output for the entire MISO PID control loop (as utilized with machine learning and AI techniques). It should be understood that within the treatment therapy, the inputs of the controller 400 may include the sensed data, and the output may include an adjustment in the course of therapy.

In illustrative embodiments, examples of outputs include stimulation current, stimulation voltage, stimulation frequency, stimulation pulse duration, latent time between stimulation pulses, number of stimulation pulses in a row and periodic clock time of stimulation. A key to getting such a control system to work optimally is to collect enough data to determine the weights to assign to each of the inputs in order to create the optimal outputs (i.e. train the model).

Although one type of control system was disclosed above, it should be understood that there are multiple control schemes that can be employed, including:

Linear Quadratic Regulator—minimizes an optimization function

Adaptive Control

Robust Control

Fuzzy Logic Control

And various nonlinear control schemes. Many of the implementable nonlinear control schemes are just linear control schemes used in a small window of operation where the nonlinear can be approximated by the linear.

A number of feedback control schemes may use machine learning or AI. Examples of other control schemes of various embodiments may include:

Reinforcement Learning (RL): Reinforcement learning is a machine learning technique where an agent learns to make decisions by interacting with an environment to maximize a cumulative reward signal. In the context of control, RL algorithms learn optimal control policies by trial and error, adjusting their actions based on feedback from the environment. Stimulation parameters in an RL control system can be constrained individually or in combination (e.g. the product of amplitude*time shall not exceed X) to ensure that outputs remain safe as the model learns.

Deep Reinforcement Learning (DRL): Deep reinforcement learning extends RL by using deep neural networks to approximate complex control policies. DRL algorithms, such as Deep Q-Networks (DQN), Deep Deterministic Policy Gradient (DDPG), and Proximal Policy Optimization (PPO).

Neuroevolution: Neuroevolution is a technique that uses evolutionary algorithms, such as genetic algorithms or genetic programming, to evolve neural network controllers 400*s* for control tasks. By evolving the structure and parameters of neural networks over generations, neuroevolution can find effective control policies for complex systems.

Fuzzy Logic Control with Machine Learning: Fuzzy logic control (FLC) is a rule-based control method that uses linguistic variables and fuzzy rules to represent control policies. Machine learning techniques, such as genetic algorithms or neural networks, can be used to automatically optimize the fuzzy rule sets or tune the membership functions based on training data, improving the controller's 400 performance.

Model Predictive Control (MPC) with Machine Learning: Model predictive control (MPC) is a control technique that solves an optimization problem at each time step to generate control actions based on a dynamic model of the system. Machine learning techniques can be used to learn or approximate the system dynamics, making MPC more robust to model uncertainties and disturbances.

Meta-Learning for Control: Meta-learning algorithms learn from previous experience and adapt quickly to new tasks or environments. In the context of control, meta-learning can be used to train controllers that can generalize across different systems or adapt to changes in the system dynamics.

The principal neuromodulation device 100 and the satellite neuromodulation devices may communicate with wires or wirelessly. Additionally, the satellite neuromodulation devices may communicate with one another with wires or wirelessly. The communication protocols may include, among other things, microwave, RF, magnetic induction, ultrasound, Bluetooth (e.g., communicate over microwaves (2.5 Ghz), and/or communication through signal generation and impedance detection (e.g., it is possible to communicate through relative signal transmission and measurement of impedance signals).

Figure 5:
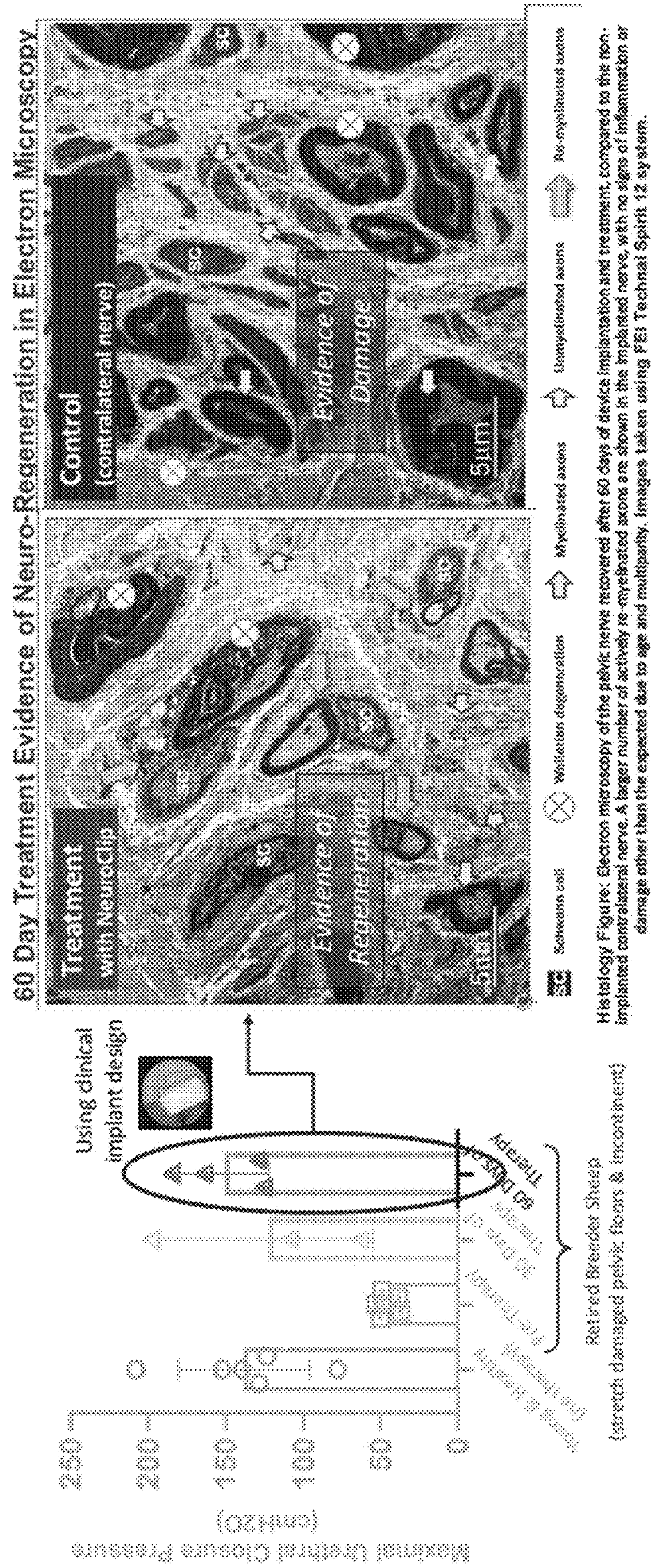
FIG. 5 shows an electron microscopy image demonstrating structural indications of regeneration and repair in a pelvic nerve following 60 days of therapeutic stimulation using the device in accordance with illustrative embodiments

FIG. 5 shows an electron microscopy image demonstrating structural indications of regeneration and repair in a pelvic nerve in sheep model following 60 days of therapeutic stimulation using the device in accordance with illustrative embodiments. In the treated nerve, numerous intact and re-myelinated axons are visible, with minimal evidence of Wallerian degeneration and preserved Schwann cell architecture, indicating active nerve repair processes.

In contrast, the contralateral untreated control nerve shows a higher prevalence of degenerating or unmyelinated axons and disrupted morphology consistent with ongoing damage. The treated nerve demonstrates increased preservation and re-myelination of axons relative to an untreated contralateral control nerve. Functional measurements from the same study population show corresponding increases in maximal urethral closure pressure after the treatment period, supporting restoration of reflexive closure mechanisms.

Figure 6:
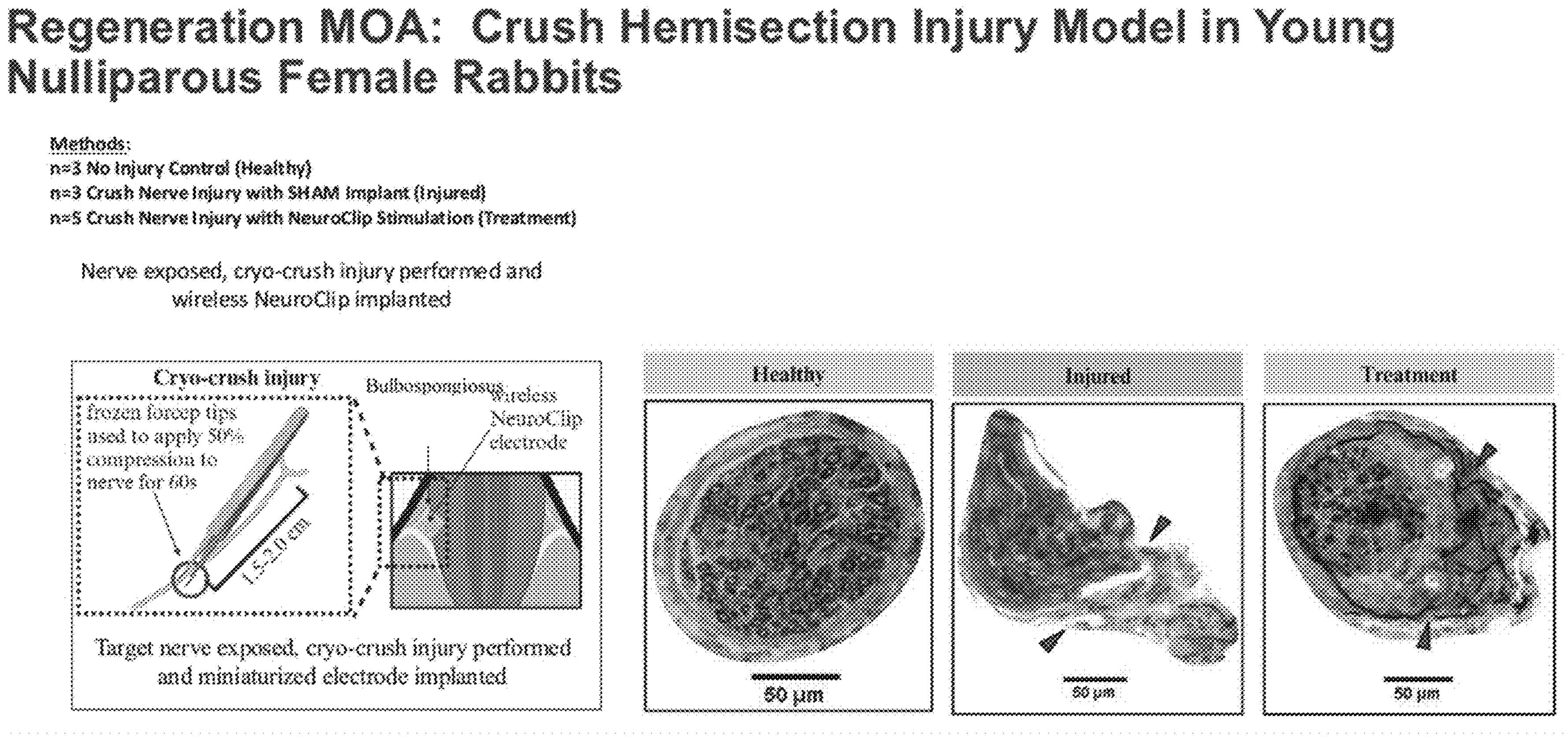
FIG. 6 illustrates a crush-hemisection nerve injury model in young nulliparous female rabbits and compares histological cross-sections of the target nerve under three conditions: healthy control, injury with sham implantation, and injury followed by chronic contact stimulation in accordance with illustrative embodiments.

FIG. 6 illustrates a crush-hemisection nerve injury model in young nulliparous female rabbits and compares histological cross-sections of the target nerve under three conditions: healthy control, injury with sham implantation, and injury followed by chronic contact stimulation. The cryo-crush injury is produced by applying approximately 50% compression to the nerve for 60 seconds using frozen forceps, after which a miniaturized wireless stimulation device is implanted in accordance with illustrative embodiments.

In the healthy nerve cross-section, organized fascicular structure and densely packed, uniformly myelinated axons are visible. In the injured-only condition, the nerve exhibits disrupted architecture, cellular disorganization, and reduced myelinated axon density. In contrast, the treatment group displays a more restored morphology, with improved fascicular organization and increased presence of myelinated axons relative to the injured control, consistent with structural indicators of regenerative activity following stimulation.

FIG. 7 shows quantitative histological analyses demonstrating cellular and axonal changes in nerves subjected to chronic stimulation following a crush injury in accordance with illustrative embodiments. The data shown in FIG. 7 provide quantitative evidence that regenerative mechanisms are present in the stimulated nerves relative to both injured and uninjured control groups. As illustrated in the upper left panel, the treatment group exhibits a measurable increase in Schwann cell density, a cellular change commonly associated with structural support for axonal repair. In the lower left panel, the distribution of g-ratios demonstrates that a higher proportion of myelinated axons in the treatment group fall within the normal physiological range when compared to the injured controls. In the lower right panel, the diameter distribution of unmyelinated axons likewise shows a greater percentage of axons within the normal size range in the treated nerves relative to the injured condition. Collectively, these analyses provide measurable histological indicators consistent with the presence of regenerative processes in nerves exposed to chronic stimulation. in accordance with illustrative embodiments.

The neuromodulation devices 100 described herein may include some or all of the features of the neuromodulation device 100 describes in in U.S. patent application Ser. Nos. 16/185,285, 16/414,169, 18/225, and/or 18/225,130. Each of these patent applications is incorporated herein by reference in its entirety. Furthermore, any of the features discussed herein may be integrated with any of the aforementioned neuromodulation devices 100. A brief description of the neuromodulation device 100 in accordance with illustrative embodiments is described in the appendix submitted herewith.

Over 90 million women in the US have pelvic floor disorders. Illustrative embodiments provide optimal treatment a much higher quality of life. A patient 105 utilizing similar embodiments has a better experience because the therapy may be: a) the first and final solution (which appeals to younger patients); b) a single procedure to treat any combination of pelvic floor disorders (OAB, SUL, Mixed Urinary Incontinence, POP, etc.); c) effective quickly; d) low to no pain; and e not contraindicated for women seeking to become pregnant. Clinicians may offer their patients the ability to treat multiple pelvic floor disorders in a single, easy-to-perform "cut down" surgical procedure that accesses peripheral nerves just under the dermis. Patient 105 progress may be monitored by an external patient 105 monitor that relays sensing and stimulation data back to the clinician.

Other examples are within the scope and spirit of the description and claims. Additionally, certain functions described above can be implemented using software, hardware, firmware, hardwiring, or combinations of any of these. Features implementing functions can also be physically located at various positions, including being distributed such that portions of functions are implemented at different physical locations.

Various embodiments of the invention may be implemented at least in part in any conventional computer programming language. For example, some embodiments may be implemented in a procedural programming language (e.g., "C"), or in an object oriented programming language (e.g., "C++"). Other embodiments of the invention may be implemented as preprogrammed hardware elements (e.g., application specific integrated circuits, FPGAs, programmable analog circuitry, and digital signal processors), or other related components.

In an alternative embodiment, the disclosed apparatus and methods (e.g., see the various flow charts described above) may be implemented as a computer program product for use with a computer system. Such implementation may include a series of computer instructions fixed either on a tangible, non-transitory medium, such as a computer readable medium (e.g., a diskette, CD-ROM, ROM, or fixed disk). The series of computer instructions can embody all or part of the functionality previously described herein with respect to the system.

Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies.

Among other ways, such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). In fact, some embodiments may be implemented in a software-as-a-service model ("SAAS") or cloud computing model. Of course, some embodiments of the invention may be implemented as a combination of both software (e.g., a computer program product) and hardware. Still other embodiments of the invention are implemented as entirely hardware, or entirely software.

In some implementations, the processor 400 includes one or more processors (or one or more processor cores) that each are configured to perform a series of instructions that result in manipulated data and/or control the operation of the other components of the controller 400. In some implementations, when executing a specific process (e.g., nerve stimulation), the processor 400 can be configured to make specific logic-based determinations based on input data received, and be further configured to provide one or more outputs that can be used to control or otherwise inform subsequent processing to be carried out by the processor 400 and/or other processors or circuitry with which processor 400 is communicatively coupled. Thus, the processor 400 reacts to specific input stimulus in a specific way and generates a corresponding output based on that input stimulus. In some example cases, the processor 400 can proceed through a sequence of logical transitions in which various internal register states and/or other bit cell states internal or external to the processor 400 may be set to logic high or logic low. As referred to herein, the processor 400 can be configured to execute a function where software is stored in a data store coupled to the processor 400, the software being configured to cause the processor 400 to proceed through a sequence of various logic decisions that result in the function being executed. The various components that are described herein as being executable by the processor 400 can be implemented in various forms of specialized hardware, software, or a combination thereof. For example, the processor can be a digital signal processor (DSP) such as a 24-bit DSP processor. The processor can be a multi-core processor, e.g., having two or more processing cores. The processor can be an Advanced RISC Machine (ARM) processor such as a 32-bit ARM processor. The processor can execute an embedded operating system, and include services provided by the operating system that can be used for file system manipulation, display & audio generation, basic networking, firewalling, data encryption and communications.

As used in this specification and the claims, the singular forms "a," "an," and "the" refer to plural referents unless the context clearly dictates otherwise. Thus, in various embodiments, any reference to the singular includes a plurality, and any reference to more than one component can include the singular. For example, reference to "the neuromodulation device" in the singular includes a plurality of neuromodulation devices, and reference to "the sensor" in the singular includes one or more sensors and equivalents known to those skilled in the art. Thus, in various embodiments, any reference to the singular includes a plurality, and any reference to more than one component can include the singular.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein.

It is, therefore, to be understood that the foregoing embodiments are presented by way of example only and that, within the scope of the appended claims and equivalents thereto, inventive embodiments may be practiced otherwise than as specifically described and claimed. Illustrative embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure. Disclosed embodiments, or portions thereof, may be combined in ways not listed above and/or not explicitly claimed. Thus, one or more features from variously disclosed examples and embodiments may be combined in various ways. For example, it is to be understood that the present disclosure contemplates that, to the extent possible, one or more features of any embodiment can be combined with one or more features of any other embodiment.

Various inventive concepts may be embodied as one or more methods, of which examples have been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Although the subject matter contained herein has been described in detail for the purpose of illustration, it is to be understood that such detail is solely for that purpose and that the present disclosure is not limited to the disclosed embodiments, but, on the contrary, is intended to cover modifications and other arrangements that are within the spirit and scope of the appended claims. For example, it is to be understood that the present disclosure contemplates that, to the extent possible, one or more features of any embodiment can be combined with one or more features of any other embodiment.

What is claimed is:

1. A method of promoting axonal regeneration and remyelination repair of a peripheral nerve, the method comprising:

stimulating a target peripheral nerve or target distal branch thereof with a direct-contact electrode, the direct-contact electrode configured to couple to a nerve having a diameter of between 1 mm and 25 mm; and delivering one or more pulse trains to the target nerve, each pulse train comprising pulses having a frequency between about 20 Hz and 100 Hz and a pulse width between about 150 microseconds and 500 microseconds, the pulse trains having a train duration between about 3 seconds and 60 seconds and being separated by rest intervals between about 0.5 minute and 5 minutes, wherein stimulation amplitude is delivered relative to a threshold appropriate for the nerve type, comprising at or above contraction threshold for a motor nerve, at or below sensation threshold for a sensory nerve, or at/above a physiological threshold for an autonomic nerve, and wherein the pulse trains are delivered in 1 to 8 pulse trains per session, thereby initiating axonal regeneration and/or promoting remyelination repair in the target nerve.

2. The method of claim 1, wherein the target nerve is a motor nerve and the amplitude is set at or above contraction threshold, defined as the minimum intensity that produces a visible or palpable contraction of the muscle innervated by the target nerve.

3. The method of claim 1, wherein the target nerve is a sensory nerve and the amplitude is set at or above sensation threshold.

4. The method of claim 1, wherein the target nerve is an autonomic nerve and the amplitude is set at or above a physiological threshold defined by a minimal measurable change in an organ-specific marker selected from heart rate, blood pressure, regional blood flow, and respiratory rate.

5. The method of claim 1, wherein if contraction threshold cannot be determined, stimulation amplitude is set at or above an electromyographic (EMG) threshold defined as the minimum intensity that elicits a detectable EMG signal in the target muscle.

6. The method of claim 1, wherein the set stimulation amplitude is less than 10% above threshold.

7. The method of claim 1, further comprising a direct-contact electrode, wherein the direct-contact electrode is configured for coupling to a nerve having a diameter smaller than 1 mm.

8. The method of claim 1, wherein stimulation is delivered in structured sessions comprising no more than eight pulse trains per session, each train lasting between about 3 seconds and 60 seconds, and total session duration maintained below one hour.

9. The method of claim 1, wherein on-target activation is confirmed by a physiological marker selected from visible or palpable muscle contraction, electromyographic activity in the target muscle, or organ-specific functional response.

10. The method of claim 1, wherein off-target absence is verified by confirming no activation of adjacent nerves through absence of secondary muscle contractions or absence of physiological changes in non-target organs.

11. The method of claim 1, wherein the neuromodulation device is configured for long-term implantation to deliver chronic stimulation over months or years.

12. The method of claim 1, wherein stimulation is delivered to achieve selective activation of a single physiological target or a physiologically meaningful portion thereof, the physiological target comprising one muscle, one sensory dermatome, or one autonomic organ or sub-portion thereof.

13. The method of claim 1, wherein stimulation is delivered to achieve semi-selective activation of two or three physiological targets within a related anatomical region, the targets comprising muscles, dermatomes, or autonomic organs that share regional or functional linkage.

14. The method of claim 1, wherein stimulation amplitude is maintained within about 0.1 mA to 3 mA for selective stimulation using direct-contact electrodes.

15. The method of claim 1, wherein the total stimulation duration per session is between 15 seconds and 60 seconds.

16. The method of claim 1, wherein the method comprises 1 to 2 sessions per day.

17. The method of claim 1, wherein the method is performed on 5 to 7 days per week.

18. The method of claim 1, wherein the method is performed for at least 4 weeks and up to 12 weeks.

19. The method of claim 1, wherein the pulse waveform is biphasic and charge-balanced with a recovery ratio selected from 1:1 and 1:2.

20. A neurostimulation system configured to promote axonal regeneration and remyelination repair of a peripheral nerve, comprising:

(a) an electrode sized to couple to a peripheral nerve or distal branch that define a target nerve, the target nerve having a diameter of between about 1 mm and 25 mm, and having insulation configured to confine current to the target nerve; and (b) a controller programmed to deliver charge-balanced biphasic pulse trains having:

a frequency between about 20 Hz and 100 Hz, a pulse width between about 150 microseconds and 500 microseconds, an interphase interval between about 25 microseconds and 100 microseconds, a train duration between about 3 seconds and 60 seconds, and rest intervals between about 0.5 minutes and 5 minutes, in one or more pulse trains per session, at least one session per day, on 1 to 7 days per week, for at least 2 weeks up to 20 weeks, the controller being further configured to set amplitude relative to a threshold appropriate for the nerve type comprising at or above contraction threshold for a motor nerve, below or near sensation threshold for a sensory nerve, or at a physiological threshold for an autonomic nerve.

21. The system of claim 20, wherein the electrode is a clip or a cuff and includes a conformal insulating body that reduces volume conduction to off-target nerves.

22. The system of claim 20, wherein the nerve stimulation device comprises:

(a) a clip-like nerve-engagement structure sized to partially surround a peripheral nerve having an average diameter between 1.0 mm and 3.0 mm;

(b) first and second electrodes disposed on an inner surface of the structure and electrically isolated from one another by an insulating body, the electrodes being electrically coupled to a pulse generator through hermetic feedthroughs; and (c) an interelectrode distance between the first and second electrodes of 2.5 mm to 3.5 mm, wherein the device is configured for active-return biphasic stimulation in which current flows between the first and second electrodes through adjacent nerve tissue, and wherein a total device width measured laterally across the electrodes and outboard insulation is ≤6 mm.

23. The system of claim 20, wherein the controller is configured to:

deliver electrical stimulation in the form of pulse bursts, each burst having a duration of 3 to 60 seconds, each session having less than 8 pulse bursts, and a total stimulation time per session of less than one hour.

24. A neuromodulation system that has a neuromodulation device configured to mechanically couple in direct contact with a distal peripheral nerve branch having a diameter between 0.5 millimeters and 3 millimeters, the neuromodulation device including a first electrode and a second electrode arranged as an active-return pair with a spacing of less than 1.5 millimeters, the neuromodulation system further having a controller configured to deliver stimulation to the distal branch at an amplitude less than 3 milliamps and to apply a therapy session that includes:

pulse bursts each having a duration between 3 seconds and 45 seconds;

a pulse frequency between 20 Hz and 80 Hz;

a pulse width between 150 microseconds and 400 microseconds;

a pulse-burst quantity between 1 and 6; and an inter-burst rest interval between 1 minute and 4 minutes;

wherein the amplitude is selected based on a threshold of the distal branch, and wherein the stimulation produces selective activation of the distal branch while maintaining off-target activation below a contraction threshold, sensation threshold, or autonomic physiological threshold of adjacent nerves.

25. The neuromodulation system of claim 24, wherein the distal peripheral nerve branch has a diameter between 0.5 millimeters and 1.5 millimeters, and the stimulation amplitude is between 0.1 mA and 1.5 mA.

* * * * *